US012030897B2

(12) United States Patent
Chen et al.

(10) Patent No.: US 12,030,897 B2
(45) Date of Patent: Jul. 9, 2024

(54) PYRROLO[2,1-F][1,2,4]TRIAZINE DERIVATIVES SERVING AS SELECTIVE HER2 INHIBITORS AND APPLICATION THEREOF

(71) Applicant: MEDSHINE DISCOVERY INC., Jiangsu (CN)

(72) Inventors: Kevin X Chen, Shanghai (CN); Fen Jiang, Shanghai (CN); Xinde Chen, Shanghai (CN); Li Zhang, Shanghai (CN); Zhaoguo Chen, Shanghai (CN); Yanxin Yu, Shanghai (CN); Kai Zhou, Shanghai (CN); Boyu Hu, Shanghai (CN); Cheng Xie, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 841 days.

(21) Appl. No.: 17/053,076

(22) PCT Filed: May 8, 2019

(86) PCT No.: PCT/CN2019/086032
§ 371 (c)(1),
(2) Date: Nov. 5, 2020

(87) PCT Pub. No.: WO2019/214651
PCT Pub. Date: Nov. 14, 2019

(65) Prior Publication Data
US 2021/0323979 A1    Oct. 21, 2021

(30) Foreign Application Priority Data
May 8, 2018    (CN) .......................... 201810434197.8

(51) Int. Cl.
C07D 519/00    (2006.01)
A61P 35/00    (2006.01)

(52) U.S. Cl.
CPC ............ *C07D 519/00* (2013.01); *A61P 35/00* (2018.01)

(58) Field of Classification Search
CPC .................................................. C07D 519/00
See application file for complete search history.

(56) References Cited

U.S. PATENT DOCUMENTS

| | | | |
|---|---|---|---|
| 7,141,571 B2 | 11/2006 | Fink et al. | |
| 2009/0048244 A1 | 2/2009 | Fink et al. | |
| 2010/0004238 A1 | 1/2010 | Ishikawa et al. | |
| 2011/0034689 A1 | 2/2011 | Lyssikatos et al. | |

FOREIGN PATENT DOCUMENTS

| | | |
|---|---|---|
| CN | 1922182 A | 2/2007 |
| CN | 101356171 A | 1/2009 |
| CN | 101611041 A | 12/2009 |
| WO | 2005065266 A2 | 7/2005 |
| WO | 2005066176 A1 | 7/2005 |
| WO | 2007059257 A2 | 5/2007 |

OTHER PUBLICATIONS

Zhang "Approved Small-Molecule ATP-Competitive Kinases Drugs Containing Indole/Azaindole/Oxindole Scaffolds: R&D and Binding Patterns Profiling" Molecules 2023, 28, 943.*
Wang "Associations of HER2 Mutation With Immune-Related Features and Immunotherapy Outcomes in Solid Tumors." Front. Immunol. (2022) 13:799988.*
Oct. 8, 2021 EESR issued in European application No. 19799711.7.
Fink B E et al: "Novel pyrrolo[1,2,4] triazin-4-amines: Dual inhibitors of EGFR and HER2 protein tyrosine kinases", Bioorganic & Medicinal Chemistry Letters, Elsevier, Amsterdam, NL, vol. 21, No. 2, Jan. 15, 2011 (Jan. 15, 2011), pp. 781-785, XP027593558, ISSN: 0960-894X, DOI: 10.1016/J.BMCL.2010.11.100[retrieved on Jan. 7, 2011].
Zalloum Hiba et al: "Discovery of new human epidermal growth factor receptor-2(HER2) inhibitors for potential use as anticancer agents via ligand-based pharmacophore modeling", Journal of Molecular Graphics and Modelling, Elsevier Science, New York, NY, US, vol. 61, Jun. 27, 2015 (Jun. 27, 2015), pp. 61-84, XP029267756, ISSN: 1093-3263, DOI: 10.1016/J.JMGM.2015.06.008.
Mastalerz et al: "5-((4-Aminopiperidin-1-yl)methy1)pyrrolot riazine dual inhibitors of EGFR and HER2 protein tyrosine kinases", Bioorganic & Medicinal Chemistry Letters, Elsevier, Amsteroam, NL, vol. 17, No. 17, Aug. 4, 2007 (Aug. 4, 2007), pp. 4947-4954, XP022184942, ISSN: 0960-894X, DOI: 10.1016/J.BMCL.2007.06.019.
Aug. 5, 2019 International Search Report issued in International Patent Application No. PCT/CN2019/086032.
Aug. 5, 2019 Written Opinion of the International Searching Authority issued in International Patent Application No. PCT/CN2019/086032.

* cited by examiner

*Primary Examiner* — David K O'Dell
(74) *Attorney, Agent, or Firm* — Houston Beshining Law Office PLLC; Liangang Ye

(57) ABSTRACT

The present invention relates to a group of pyrrolo[2,1-f][1,2,4]triazine derivatives serving as selective HER2 inhibitors and an application thereof in the preparation of a drug that serves as an HER2 inhibitor. Specifically, the present invention relates to a compound represented by formula (I), an isomer thereof or a pharmaceutically acceptable salt thereof.

14 Claims, No Drawings

PYRROLO[2,1-F][1,2,4]TRIAZINE DERIVATIVES SERVING AS SELECTIVE HER2 INHIBITORS AND APPLICATION THEREOF

The present application is a National Stage of International Application No. PCT/CN2019/086032, filed on May 8, 2019, which claims priority of the Chinese Patent Application No. CN201810434197.8 filed on May 8, 2018, the contents of which are incorporated herein by reference in their entireties.

TECHNICAL FIELD

The present disclosure relates to a group of pyrrolo[2,1-f][1,2,4]triazine derivatives serving as selective HER2 inhibitors and an application thereof in the preparation of a drug that serves as an HER2 inhibitor. Specifically, the present disclosure relates to a compound represented by formula (I), an isomer thereof or a pharmaceutically acceptable salt thereof.

BACKGROUND

Human epidermal growth factor receptor (HER, EGFR) is a member of the protein tyrosine kinase family. It is widely distributed on the cell membrane of various tissues in the human body and can regulate cell proliferation, growth, metastasis and apoptosis. Its structure consists of three parts: the extracellular ligand binding domain, the transmembrane domain, and the intracellular tyrosine kinase domain. According to the structural differences of receptors, HER can be divided into four subtypes, namely HER1 (EGFR, ErbB-1), HER2 (ErbB-2), HER3 (ErbB-3) and HER4 (ErbB-4). Studies have proved that HER2 is overexpressed in a variety of cancers, and HER2 overexpression indicates that tumors are more aggressive and easier to relapse and metastasize early. In 1998, Herceptin (humanized anti-HER2 monoclonal antibody) was approved for breast cancer in the United States. Currently, HER2 has become a therapeutic target for breast cancer, gastric cancer, and esophageal cancer. The HER2 small-molecule kinase inhibitors currently on the market and under development usually also inhibit HER1 at the same time. Studies have proved that inhibiting HER1 will produce some target-related side effects, such as rash and diarrhea. Therefore, reducing the inhibitory activity of the compound on HER1 and increasing the selectivity of the compound on HER2 can effectively alleviate the aforementioned side effects. Currently, no selective HER2 tyrosine kinase inhibitor has been approved for marketing, and currently, there is a compound tucatinib, which is under clinical study II (WO 2007/059257 A2).

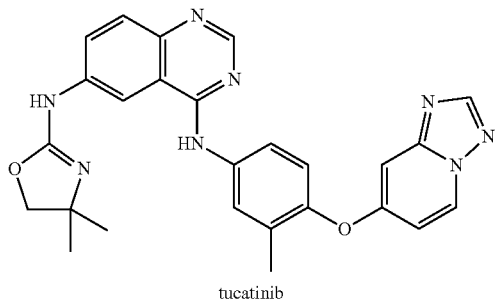 [SMILES: Cc1cc(Nc2ncnc3ccc(NC4=NC(C)(C)CO4)cc23)ccc1Oc1ccn2ncnc2c1]

tucatinib

Therefore, it is necessary to further develop selective HER2 tyrosine kinase inhibitors.

CONTENT OF THE PRESENT INVENTION

The present disclosure provides a compound represented by formula (I), an isomer thereof or a pharmaceutically acceptable salt thereof,

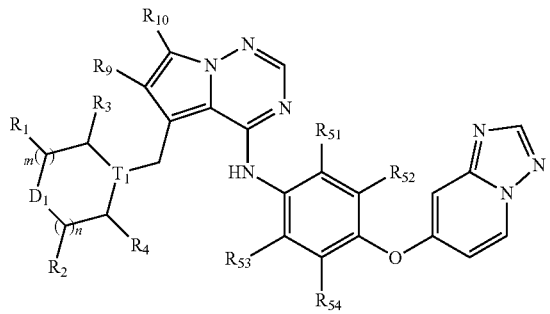

(I)

wherein
m is 0, 1 or 2;
n is 0, 1 or 2;
$T_1$ is selected from N and CH;
$D_1$ is selected from O, $N(R_6)$ and $C(R_7)(R_8)$;
$R_1$ is independently selected from H, F, Cl, Br, I, OH, $NH_2$, $C_{1-6}$ alkyl and $C_{1-6}$ alkoxy, wherein the $C_{1-6}$ alkyl and $C_{1-6}$ alkoxy are optionally substituted with 1, 2 or 3 $R_a$;
$R_2$ is each independently selected from H, F, Cl, Br, I, OH, $NH_2$ and $C_{1-6}$ alkyl, wherein the $C_{1-6}$ alkyl is optionally substituted with 1, 2 or 3 $R_b$;
or $R_1$ and $R_2$ are attached to each other to form $-(CH_2)_p-$, where both m and n are 1;
$R_3$ and $R_4$ are each independently selected from H, F, Cl, Br, I, OH, $NH_2$ and $C_{1-6}$ alkyl, wherein the $C_{1-6}$ alkyl is optionally substituted with 1, 2 or 3 $R_c$;
or $R_3$ and $R_4$ are attached to each other to form $-(CH_2)_q-$;
p is 1 or 2;
q is 1 or 2;
$R_{51}$, $R_{52}$, $R_{53}$ and $R_{54}$ are each independently selected from H, F, Cl, Br, I, OH, $NH_2$, $C_{1-6}$ alkyl and $C_{1-3}$ alkoxy, wherein the $C_{1-6}$ alkyl and $C_{1-3}$ alkoxy are optionally substituted with 1, 2 or 3 $R_d$;
$R_6$ is selected from H, F, Cl, Br, I, OH, $NH_2$, $C_{1-6}$ alkyl and $-C(=O)-C_{2-6}$ alkenyl, wherein the $C_{1-6}$ alkyl and $-C(=O)-C_{2-6}$ alkenyl are optionally substituted with 1, 2 or 3 $R_e$;
$R_7$ is selected from H, F, Cl, Br, I, OH, $NH_2$ and $C_{1-6}$ alkyl, wherein the $NH_2$ and $C_{1-6}$ alkyl are optionally substituted with 1, 2 or 3 $R_f$;
$R_8$ is selected from H, F, Cl, Br, I and $C_{1-6}$ alkyl, wherein the $C_{1-6}$ alkyl is optionally substituted with 1, 2 or 3 $R_g$;
$R_9$ and $R_{10}$ are each independently selected from H, F, Cl, Br, I, OH, $NH_2$, $C_{1-6}$ alkyl and $C_{1-3}$ alkoxy, wherein the $C_{1-6}$ alkyl and $C_{1-3}$ alkoxy are optionally substituted with 1, 2 or 3 $R_h$;
$R_a$, $R_b$ and $R_c$ are each independently selected from F, Cl, Br, I, OH and $NH_2$;
$R_d$ is each independently selected from F, Cl, Br, I, OH, $NH_2$ and $C_{1-3}$ alkyl, wherein the $C_{1-3}$ alkyl is optionally substituted with 1, 2 or 3 R;

$R_e$, $R_f$, $R_g$ and $R_h$ are each independently selected from F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted with 1, 2 or 3 R;

R is each independently selected from F, Cl, Br, I, OH, $NH_2$, $CH_3$, Et and —$OCH_3$.

In some embodiments of the present disclosure, the above-mentioned $R_d$ is each independently selected from F, Cl, Br, I, OH and $NH_2$, and other variables are as defined in the present disclosure.

In some embodiments of the present disclosure, the above-mentioned $R_e$, $R_f$, $R_g$ and $R_h$ are each independently selected from F, Cl, Br, I, OH, $NH_2$, $CH_3$, Et,

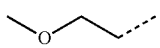

and —$OCH_3$, and other variables are as defined in the present disclosure.

In some embodiments of the present disclosure, the above-mentioned $R_1$ is each independently selected from H, F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted with 1, 2 or 3 $R_a$, and other variables are as defined in the present disclosure.

In some embodiments of the present disclosure, the above-mentioned $R_1$ is each independently selected from H, F, Cl, Br, I, OH, $NH_2$, $CH_3$, Et and —$OCH_3$, and other variables are as defined in the present disclosure.

In some embodiments of the present disclosure, the above-mentioned $R_2$ is each independently selected from H, F, Cl, Br, I, OH, $NH_2$ and $C_{1-3}$ alkyl, wherein the $C_{1-3}$ alkyl is optionally substituted with 1, 2 or 3 $R_b$, and other variables are as defined in the present disclosure.

In some embodiments of the present disclosure, the above-mentioned $R_2$ is each independently selected from H, F, Cl, Br, I, OH, $NH_2$, $CH_3$ and Et, and other variables are as defined in the present disclosure.

In some embodiments of the present disclosure, the above-mentioned $R_3$ and $R_4$ are each independently selected from H, F, Cl, Br, I, OH, $NH_2$ and $C_{1-3}$ alkyl, wherein the $C_{1-3}$ alkyl is optionally substituted with 1, 2 or 3 $R_c$, and other variables are as defined in the present disclosure.

In some embodiments of the present disclosure, the above-mentioned $R_3$ and $R_4$ are each independently selected from H, F, Cl, Br, I, OH, $NH_2$, $CH_3$ and Et, and other variables are as defined in the present disclosure.

In some embodiments of the present disclosure, the above-mentioned $R_{51}$, $R_{52}$, $R_{53}$ and $R_{54}$ are each independently selected from H, F, Cl, Br, I, OH, $NH_2$ and $C_{1-3}$ alkyl, wherein the $C_{1-3}$ alkyl is optionally substituted with 1, 2 or 3 $R_d$, and other variables are as defined in the present disclosure.

In some embodiments of the present disclosure, the above-mentioned $R_{51}$, $R_{52}$, $R_{53}$ and $R_{54}$ are each independently selected from H, F, Cl, Br, I, OH, $NH_2$, $CH_3$, Et and $CF_3$, and other variables are as defined in the present disclosure.

In some embodiments of the present disclosure, the above-mentioned $R_6$ is selected from H, F, Cl, Br, I, OH, $NH_2$, $C_{1-3}$ alkyl and —C(=O)—$C_{2-4}$ alkenyl, wherein the $C_{1-3}$ alkyl and —C(=O)—$C_{2-4}$ alkenyl, are optionally substituted with 1, 2 or 3 $R_e$, and other variables are as defined in the present disclosure.

In some embodiments of the present disclosure, the above-mentioned $R_6$ is selected from H, F, Cl, Br, I, OH, $NH_2$, $CH_3$, Et and —C(=O)—CH=$CH_2$, and other variables are as defined in the present disclosure.

In some embodiments of the present disclosure, the above-mentioned $R_7$ is selected from H, F, Cl, Br, I, OH, $NH_2$ and $C_{1-3}$ alkyl, wherein the $NH_2$ and $C_{1-3}$ alkyl are optionally substituted with 1, 2 or 3 $R_f$, and other variables are as defined in the present disclosure.

In some embodiments of the present disclosure, the above-mentioned $R_7$ is selected from H, F, Cl, Br, I, OH, $NH_2$, $CH_3$, Et,

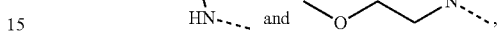

and other variables are as defined in the present disclosure.

In some embodiments of the present disclosure, the above-mentioned $R_8$ is selected from H, F, Cl, Br, I and $C_{1-3}$ alkyl, wherein the $C_{1-3}$ alkyl is optionally substituted with 1, 2 or 3 $R_g$, and other variables are as defined in the present disclosure.

In some embodiments of the present disclosure, the above-mentioned $R_8$ is selected from H, F, Cl, Br, I, $CH_3$, Et and

and other variables are as defined in the present disclosure.

In some embodiments of the present disclosure, the above-mentioned $R_9$ and $R_{10}$ are each independently selected from H, F, Cl, Br, I, OH, $NH_2$ and $C_{1-3}$ alkyl, wherein the $C_{1-3}$ alkyl is optionally substituted with 1, 2 or 3 $R_g$, and other variables are as defined in the present disclosure.

In some embodiments of the present disclosure, the above-mentioned $R_9$ and $R_{10}$ are each independently selected from H, F, Cl, Br, I, OH, $NH_2$, $CH_3$ and Et, and other variables are as defined in the present disclosure.

In some embodiments of the present disclosure, the above-mentioned structural unit

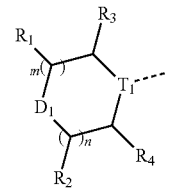

is selected from

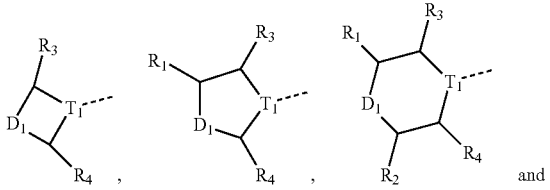

-continued

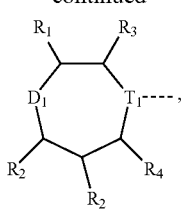

and other variables are as defined in the present disclosure.

In some embodiments of the present disclosure, the above-mentioned structural unit

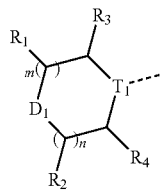

is selected from

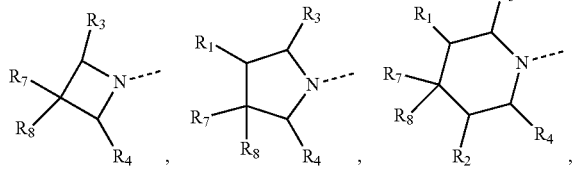

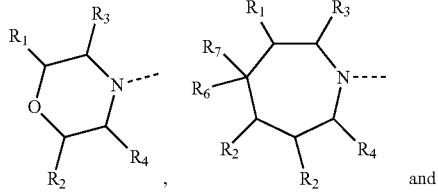

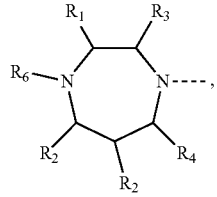

and and other variables are as defined in the present disclosure.

In some embodiments of the present disclosure, the above-mentioned structural unit

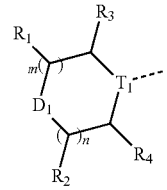

is selected from

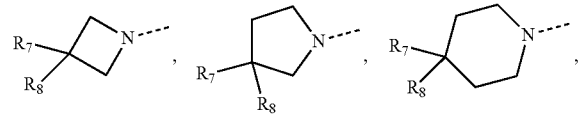
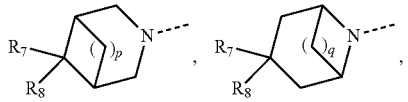

and other variables are as defined in the present disclosure.

In some embodiments of the present disclosure, the above-mentioned structural unit

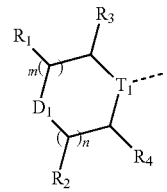

is selected from

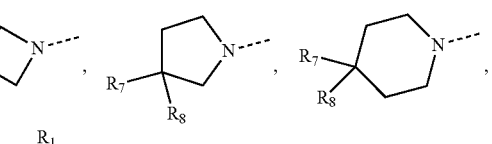

-continued

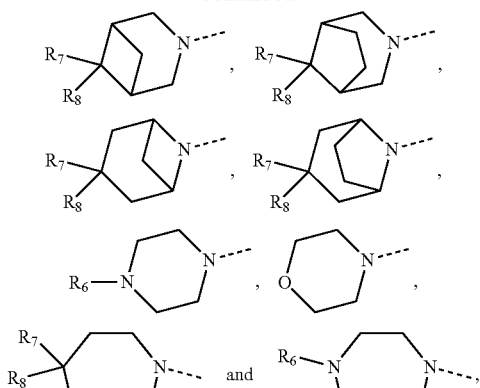

and other variables are as defined in the present disclosure.

In some embodiments of the present disclosure, the above-mentioned structural unit

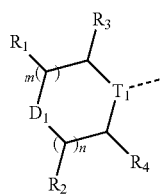

is selected from

-continued

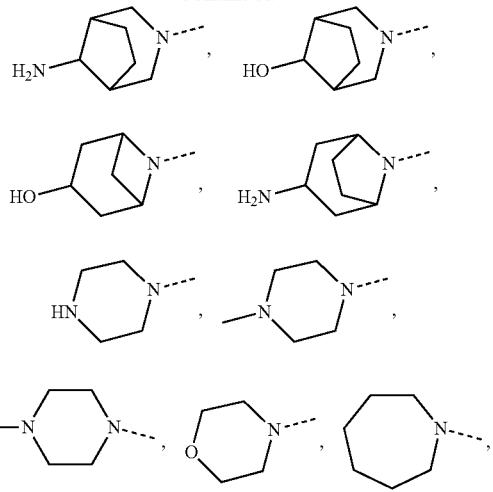

and other variables are as defined in the present disclosure.

There are still some embodiments of the present disclosure derived from any combination of the above-mentioned variables.

In some embodiments of the present disclosure, the above-mentioned compound, an isomer thereof or a pharmaceutically acceptable salt thereof is selected from

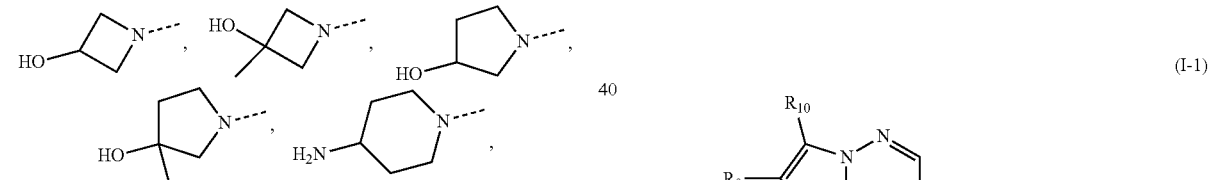

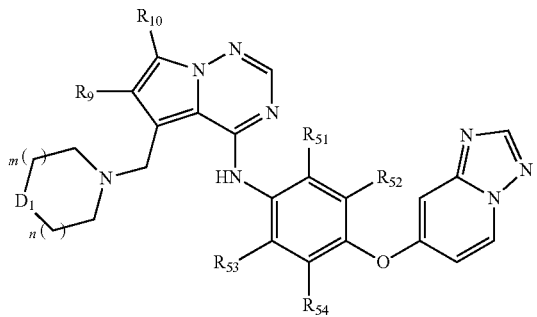

(I-1)

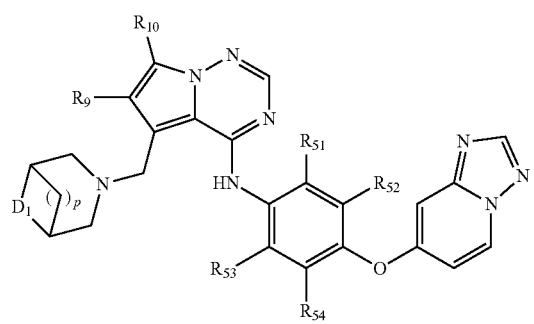

(I-2)

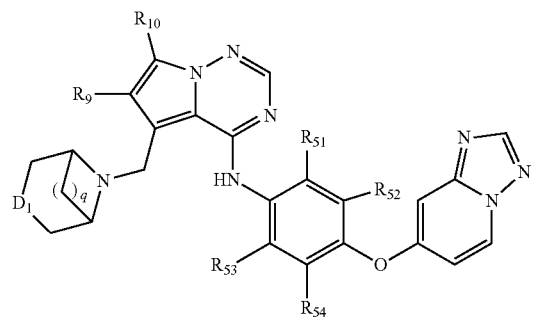
(I-3)
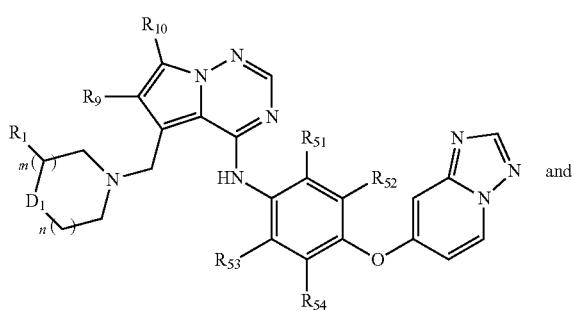
(II-1)
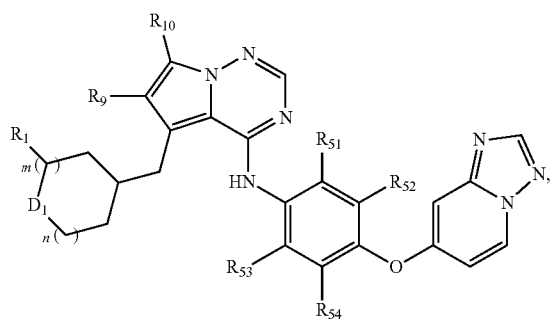
(II-2)
wherein
m, n, p, q, $D_1$, $R_1$, $R_{51}$, $R_{52}$, $R_{53}$, $R_{54}$, $R_9$ and $R_{10}$ are as defined in the present disclosure.
In some embodiments of the present disclosure, the above-mentioned compound, an isomer thereof or a pharmaceutically acceptable salt thereof is selected from
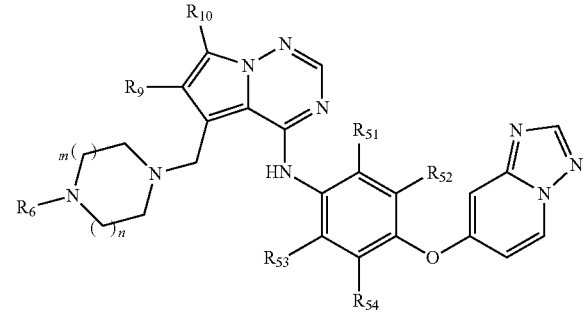
(I-1B)
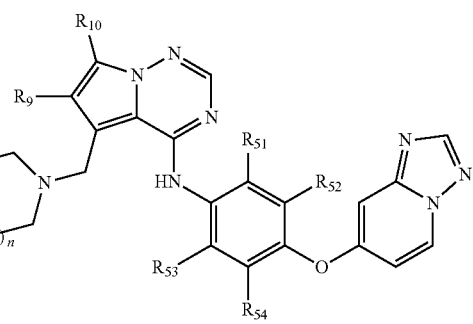
(I-1C)
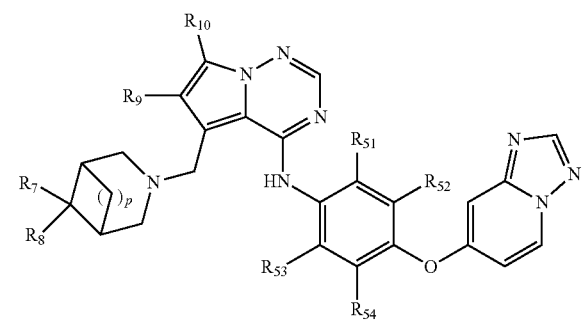
(I-2A)
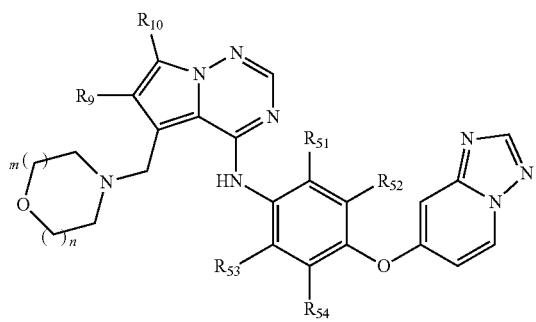
(I-1A)
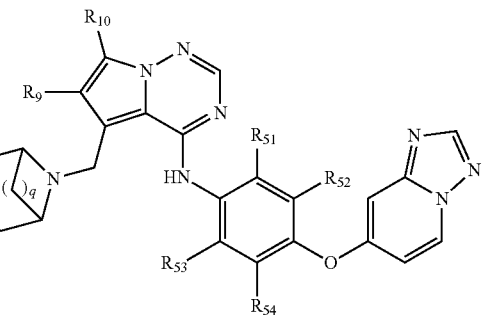
(I-3A)

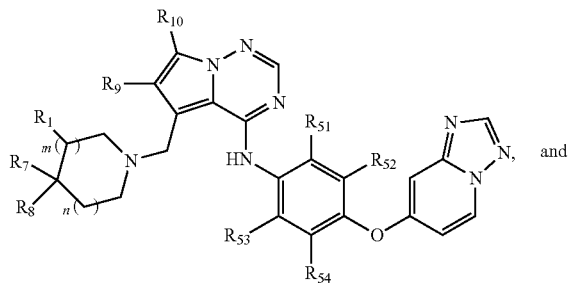
(II-1A)
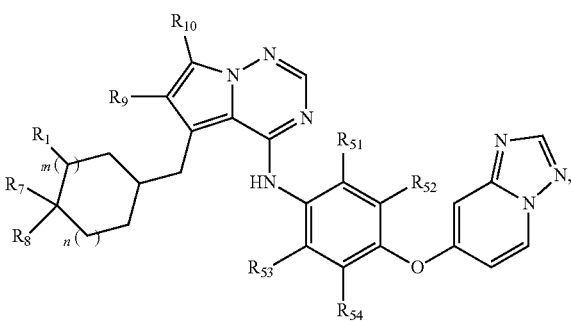
(II-1B)
wherein
wherein m, n, p, q, $R_1$, $R_{51}$, $R_{52}$, $R_{53}$, $R_{54}$, $R_6$, $R_7$, $R_8$, $R_9$ and $R_{10}$ are as defined in the present disclosure.
In some embodiments of the present disclosure, the above-mentioned compound, an isomer thereof or a pharmaceutically acceptable salt thereof is selected from
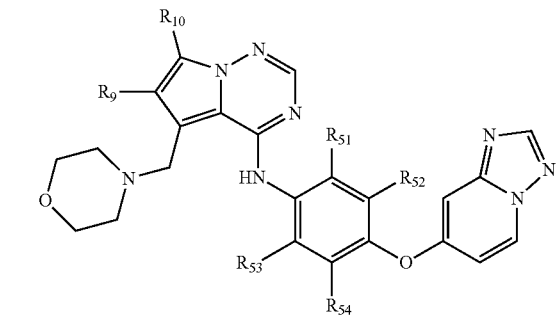
(I-1A1)
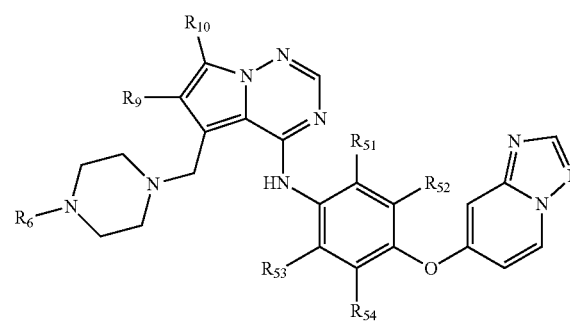
(I-1B1)
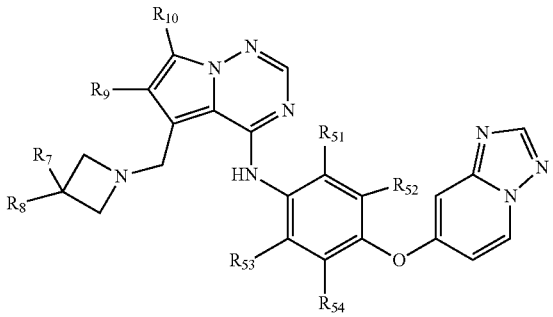
(I-1C1)
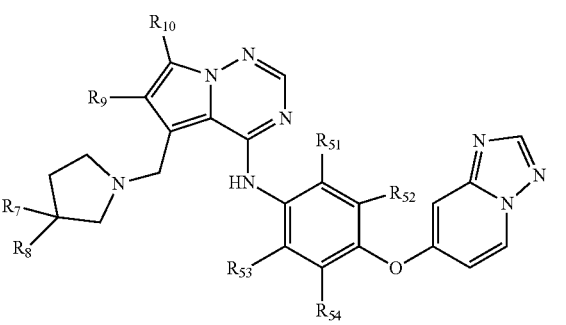
(I-1C2)
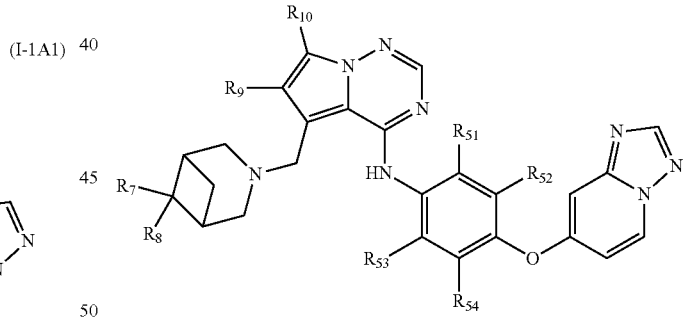
(I-2A1)
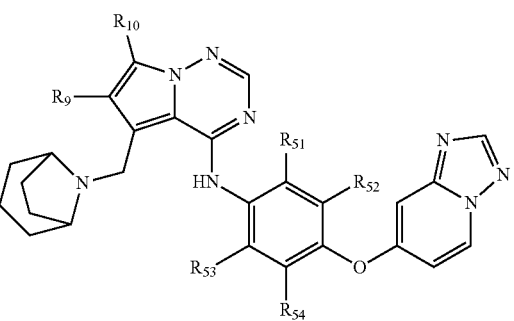
(I-3A1)

-continued

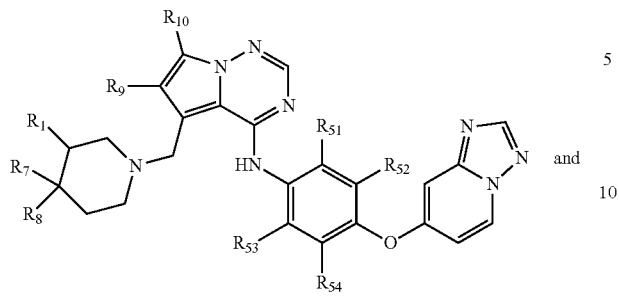

(II-1A1)

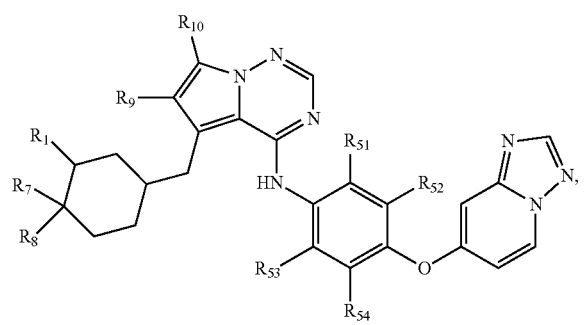

(II-1B1)

wherein
$R_1$, $R_{51}$, $R_{52}$, $R_{53}$, $R_{54}$, $R_6$, $R_7$, $R_8$, $R_9$ and $R_{10}$ are as defined in the present disclosure.

The present disclosure also provides a compound represented by formula (I), an isomer thereof or a pharmaceutically acceptable salt thereof,

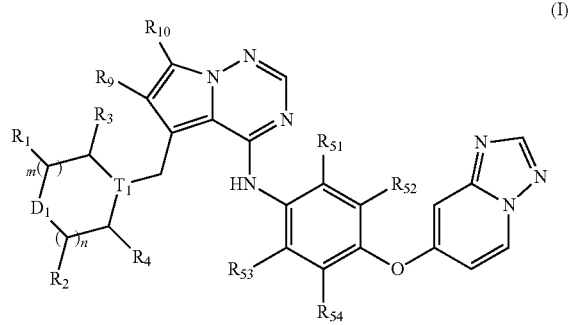

(I)

wherein
m is 0, 1 or 2;
n is 0, 1 or 2;
$T_1$ is selected from N and CH;
$D_1$ is selected from O, $N(R_6)$ and $C(R_7)(R_8)$;
$R_1$ is each independently selected from H, F, Cl, Br, I, OH, $NH_2$ and $C_{1-6}$ alkyl, wherein the $C_{1-6}$ alkyl is optionally substituted with 1, 2 or 3 $R_a$;
$R_2$ is each independently selected from H, F, Cl, Br, I, OH, $NH_2$ and $C_{1-6}$ alkyl, wherein the $C_{1-6}$ alkyl is optionally substituted with 1, 2 or 3 $R_b$;
or $R_1$ and $R_2$ are attached to each other to form —$(CH_2)_p$—, where both m and n are 1;
$R_3$ and $R_4$ are each independently selected from H, F, Cl, Br, I, OH, $NH_2$ and $C_{1-6}$ alkyl, wherein the $C_{1-6}$ alkyl is optionally substituted with 1, 2 or 3 $R_c$;

or $R_3$ and $R_4$ are attached to each other to form —$(CH_2)_q$—;
p is 1 or 2;
q is 1 or 2;
$R_{51}$, $R_{52}$, $R_{53}$ and $R_{54}$ are each independently selected from H, F, Cl, Br, I, OH, $NH_2$, $C_{1-6}$ alkyl and $C_{1-3}$ alkoxy, wherein the $C_{1-6}$ alkyl and $C_{1-3}$ alkoxy are optionally substituted with 1, 2 or 3 $R_d$;
$R_6$ is selected from H, F, Cl, Br, I, OH, $NH_2$, $C_{1-6}$ alkyl and —C(=O)—$C_{2-6}$ alkenyl, wherein the $C_{1-6}$ alkyl and —C(=O)—$C_{2-6}$ alkenyl are optionally substituted with 1, 2 or 3 $R_e$;
$R_7$ is selected from H, F, Cl, Br, I, OH, $NH_2$ and $C_{1-6}$ alkyl, wherein the $NH_2$ and $C_{1-6}$ alkyl are optionally substituted with 1, 2 or 3 $R_f$;
$R_8$ is selected from H, F, Cl, Br, I and $C_{1-6}$ alkyl, wherein the $C_{1-6}$ alkyl is optionally substituted with 1, 2 or 3 $R_g$;
$R_9$ and $R_{10}$ are each independently selected from H, F, Cl, Br, I, OH, $NH_2$, $C_{1-6}$ alkyl and $C_{1-3}$ alkoxy, wherein the $C_{1-6}$ alkyl and $C_{1-3}$ alkoxy are optionally substituted with 1, 2 or 3 $R_h$;
$R_a$, $R_b$ and $R_c$ are each independently selected from F, Cl, Br, I, OH and $NH_2$;
$R_d$ is each independently selected from F, Cl, Br, I, OH, $NH_2$ and $C_{1-3}$ alkyl, wherein the $C_{1-3}$ alkyl is optionally substituted with 1, 2 or 3 R;
$R_e$, $R_f$, $R_g$ and $R_h$ are each independently selected from F, Cl, Br, I, OH, $NH_2$ and $C_{1-3}$ alkyl, wherein the $C_{1-3}$ alkyl is optionally substituted with 1, 2 or 3 R;
R is each independently selected from F, Cl, Br, I, OH and $NH_2$.

In some embodiments of the present disclosure, the above-mentioned $R_d$ is each independently selected from F, Cl, Br, I, OH and $NH_2$, and other variables are as defined in the present disclosure.

In some embodiments of the present disclosure, the above-mentioned $R_e$, $R_f$, $R_g$ and $R_h$ are each independently selected from F, Cl, Br, I, OH and $NH_2$, and other variables are as defined in the present disclosure.

In some embodiments of the present disclosure, the above-mentioned $R_1$ is each independently selected from H, F, Cl, Br, I, OH, $NH_2$ and $C_{1-3}$ alkyl, wherein the $C_{1-3}$ alkyl is optionally substituted with 1, 2 or 3 $R_a$, and other variables are as defined in the present disclosure.

In some embodiments of the present disclosure, the above-mentioned $R_1$ is each independently selected from H, F, Cl, Br, I, OH, $NH_2$, $CH_3$ and Et, and other variables are as defined in the present disclosure.

In some embodiments of the present disclosure, the above-mentioned $R_2$ is each independently selected from H, F, Cl, Br, I, OH, $NH_2$ and $C_{1-3}$ alkyl, wherein the $C_{1-3}$ alkyl is optionally substituted with 1, 2 or 3 $R_b$, and other variables are as defined in the present disclosure.

In some embodiments of the present disclosure, the above-mentioned $R_2$ is each independently selected from H, F, Cl, Br, I, OH, $NH_2$, $CH_3$ and Et, and other variables are as defined in the present disclosure.

In some embodiments of the present disclosure, the above-mentioned $R_3$ and $R_4$ are each independently selected from H, F, Cl, Br, I, OH, $NH_2$ and $C_{1-3}$ alkyl, wherein the $C_{1-3}$ alkyl is optionally substituted with 1, 2 or 3 $R_c$, and other variables are as defined in the present disclosure.

In some embodiments of the present disclosure, the above-mentioned $R_3$ and $R_4$ are each independently selected from H, F, Cl, Br, I, OH, $NH_2$, $CH_3$ and Et, and other variables are as defined in the present disclosure.

In some embodiments of the present disclosure, the above-mentioned $R_{51}$, $R_{52}$, $R_{53}$ and $R_{54}$ are each independently selected from H, F, Cl, Br, I, OH, $NH_2$ and $C_{1-3}$ alkyl, wherein the $C_{1-3}$ alkyl is optionally substituted with 1, 2 or 3 $R_d$, and other variables are as defined in the present disclosure.

In some embodiments of the present disclosure, the above-mentioned $R_{51}$, $R_{52}$, $R_{53}$ and $R_{54}$ are each independently selected from H, F, Cl, Br, I, OH, $NH_2$, $CH_3$ and Et, and other variables are as defined in the present disclosure.

In some embodiments of the present disclosure, the above-mentioned $R_6$ is selected from H, F, Cl, Br, I, OH, $NH_2$, $C_{1-3}$ alkyl and —C(=O)—$C_{2-4}$ alkenyl, wherein the $C_{1-3}$ alkyl and —C(=O)—$C_{2-4}$ alkenyl, are optionally substituted with 1, 2 or 3 $R_e$, and other variables are as defined in the present disclosure.

In some embodiments of the present disclosure, the above-mentioned $R_6$ is selected from H, F, Cl, Br, I, OH, $NH_2$, $CH_3$, Et and —C(=O)—CH=$CH_2$, and other variables are as defined in the present disclosure.

In some embodiments of the present disclosure, the above-mentioned $R_7$ is selected from H, F, Cl, Br, I, OH, $NH_2$ and $C_{1-3}$ alkyl, wherein the $NH_2$ and $C_{1-3}$ alkyl are optionally substituted with 1, 2 or 3 $R_f$, and other variables are as defined in the present disclosure.

In some embodiments of the present disclosure, the above-mentioned $R_7$ is selected from H, F, Cl, Br, I, OH, $NH_2$, $CH_3$ and Et, and other variables are as defined in the present disclosure.

In some embodiments of the present disclosure, the above-mentioned $R_8$ is selected from H, F, Cl, Br, I and $C_{1-3}$ alkyl, wherein the $C_{1-3}$ alkyl is optionally substituted with 1, 2 or 3 $R_g$, and other variables are as defined in the present disclosure.

In some embodiments of the present disclosure, the above-mentioned $R_8$ is selected from H, F, Cl, Br, I, $CH_3$ and Et, and other variables are as defined in the present disclosure.

In some embodiments of the present disclosure, the above-mentioned $R_9$ and $R_{10}$ are each independently selected from H, F, Cl, Br, I, OH, $NH_2$ and $C_{1-3}$ alkyl, wherein the $C_{1-3}$ alkyl is optionally substituted with 1, 2 or 3 $R_g$, and other variables are as defined in the present disclosure.

In some embodiments of the present disclosure, the above-mentioned $R_9$ and $R_{10}$ are each independently selected from H, F, Cl, Br, I, OH, $NH_2$, $CH_3$ and Et, and other variables are as defined in the present disclosure.

In some embodiments of the present disclosure, the above-mentioned structural unit

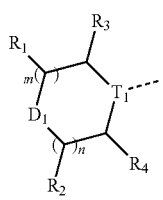

is selected from

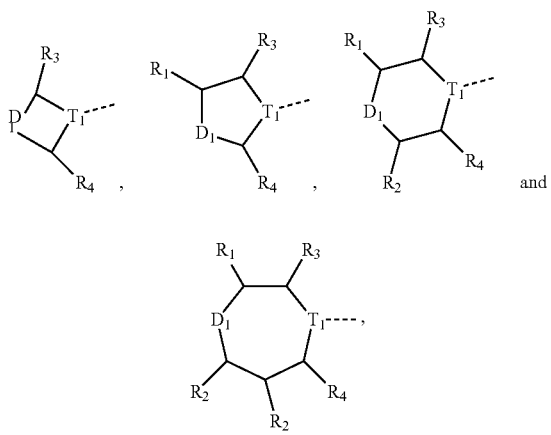

and other variables are as defined in the present disclosure.

In some embodiments of the present disclosure, the above-mentioned structural unit

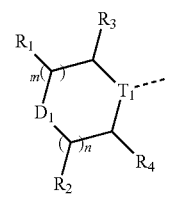

is selected from

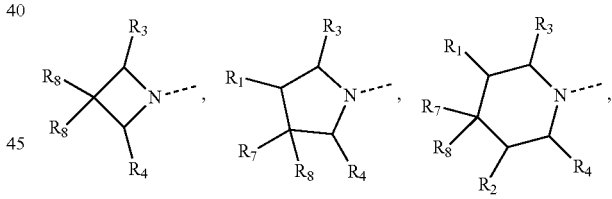

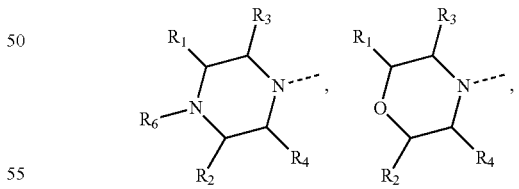

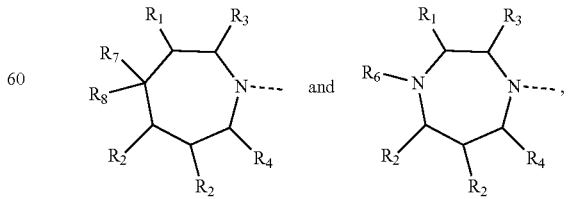

and other variables are as defined in the present disclosure.

In some embodiments of the present disclosure, the above-mentioned structural unit

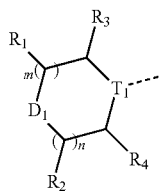

is selected from

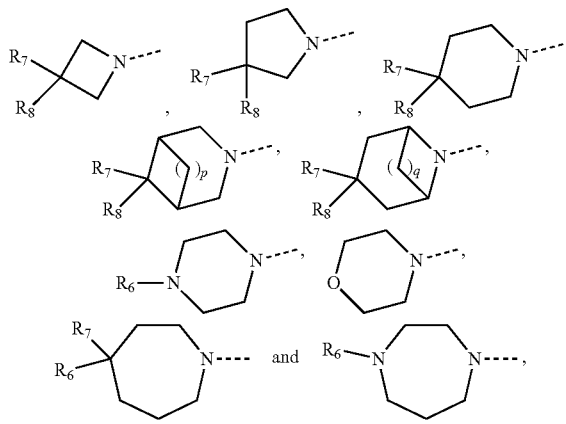

and other variables are as defined in the present disclosure.

In some embodiments of the present disclosure, the above-mentioned structural unit

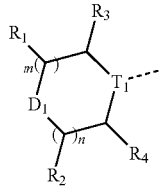

is selected from

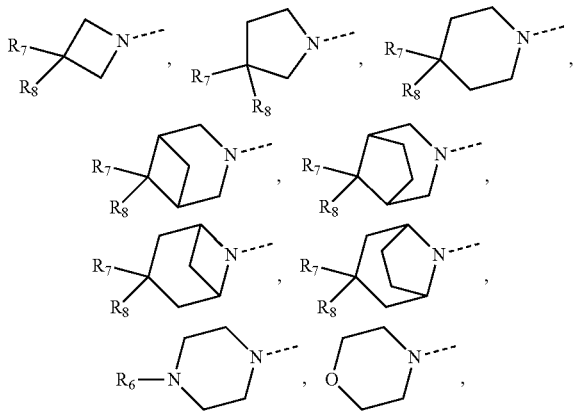

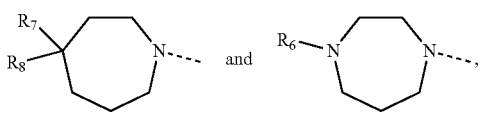

and other variables are as defined in the present disclosure.

In some embodiments of the present disclosure, the above-mentioned structural unit

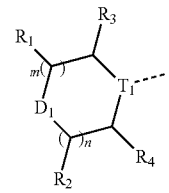

is selected from

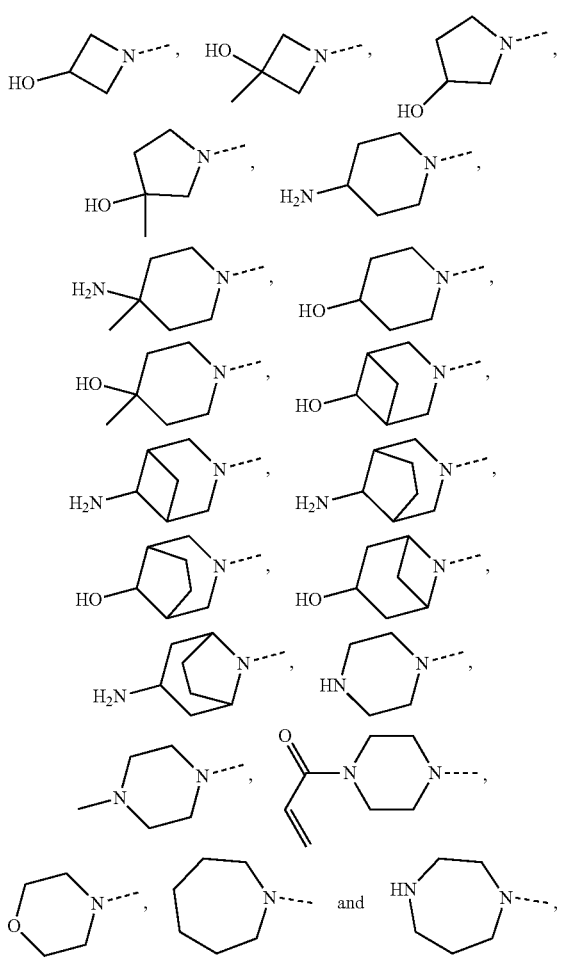

and other variables are as defined in the present disclosure.

In some embodiments of the present disclosure, the above-mentioned compound, an isomer thereof or a pharmaceutically acceptable salt thereof is selected from (I-1)

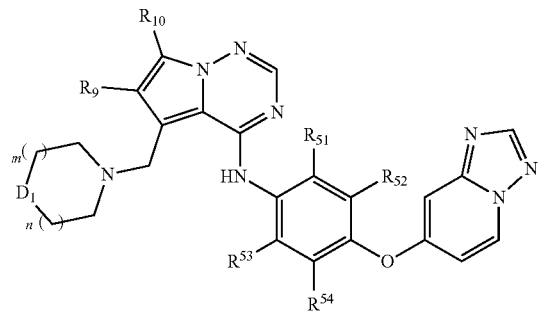

(I-1B)

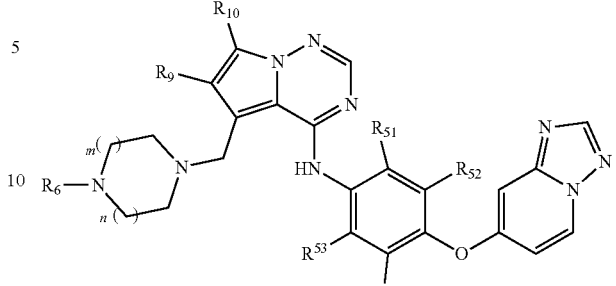

(I-2)

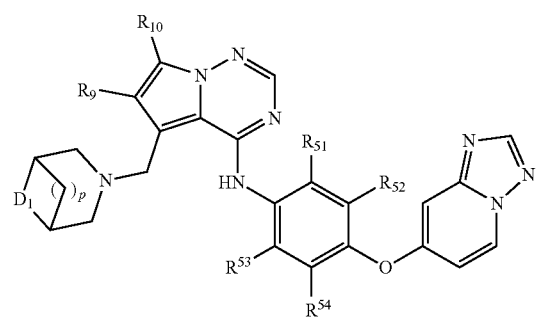

(I-1C)

(I-3)

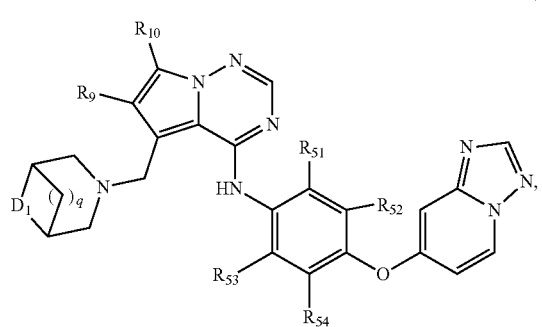

(I-2A)

wherein m, n, p, q, $D_1$, $R_{51}$, $R_{52}$, $R_{53}$, $R_{54}$, $R_9$ and $R_{10}$ are as defined in the present disclosure.

In some embodiments of the present disclosure, the above-mentioned compound, an isomer thereof or a pharmaceutically acceptable salt thereof is selected from (I-1A)

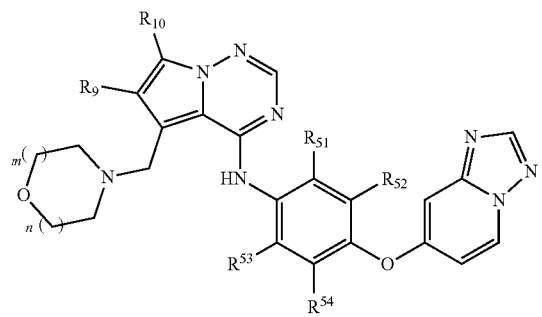

(I-3A)

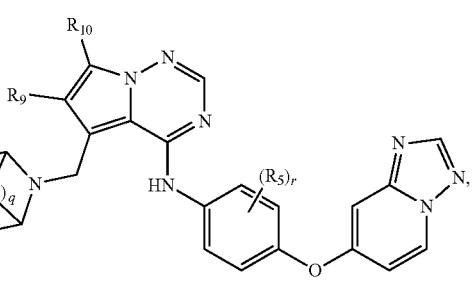

wherein m, n, p, q, $R_{51}$, $R_{52}$, $R_{53}$, $R_{54}$, $R_6$, $R_7$, $R_8$, $R_9$ and $R_{10}$ are as defined in the present disclosure.

The present disclosure also provides a compound represented by the following formula, an isomer thereof or a pharmaceutically acceptable salt thereof, which is selected from 21
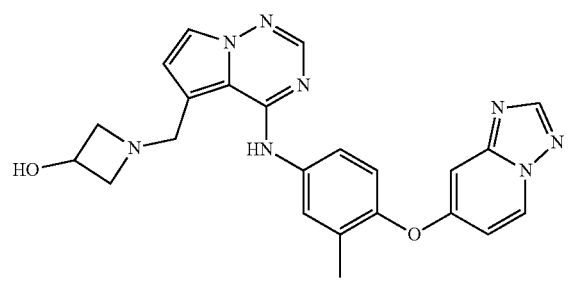
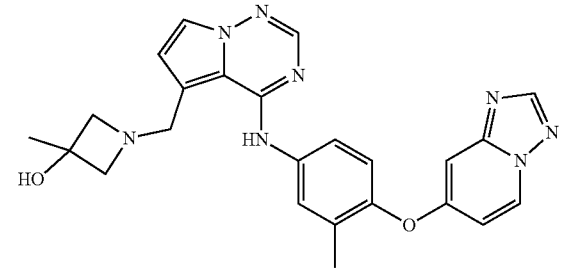
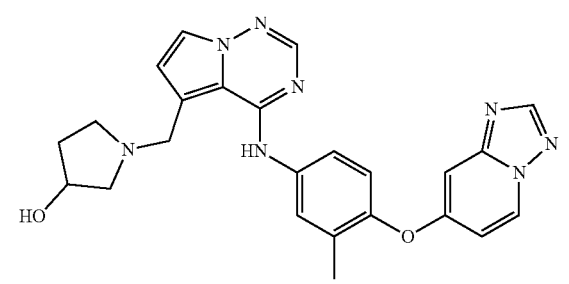
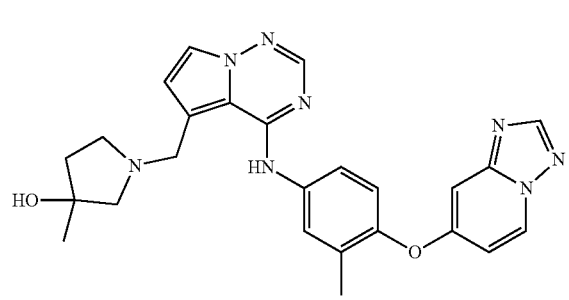
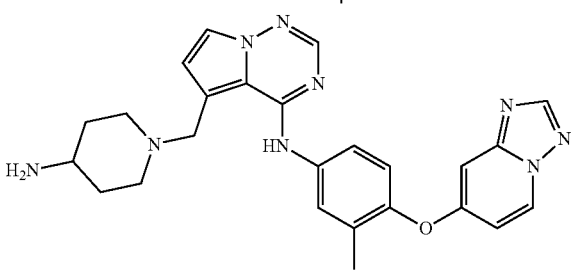
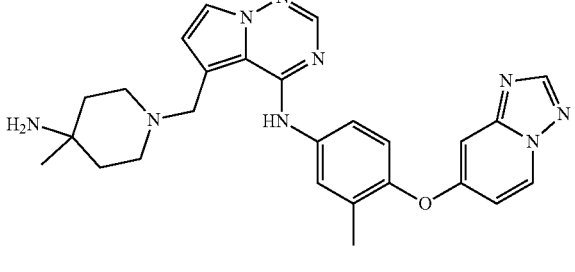
22
-continued
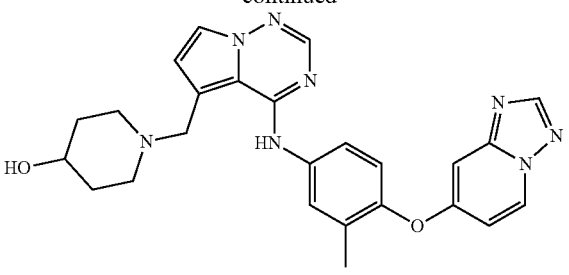
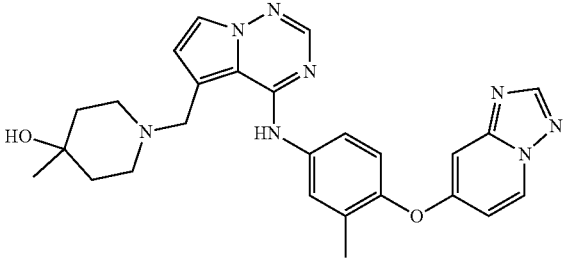
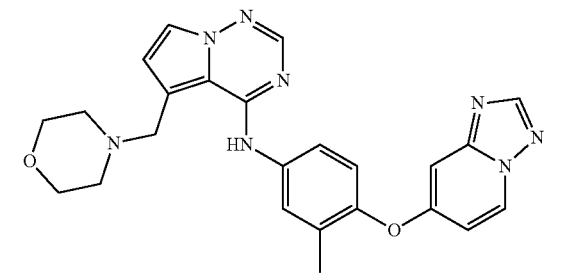
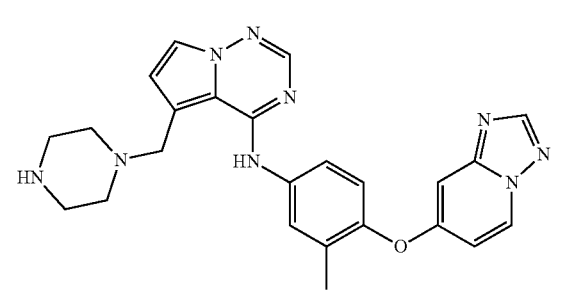
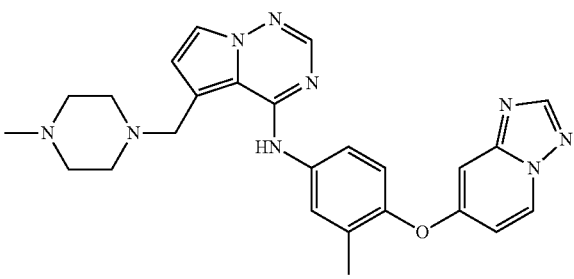
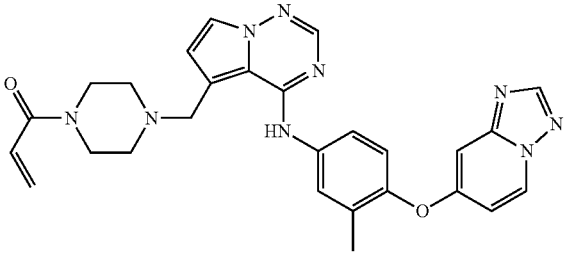

-continued
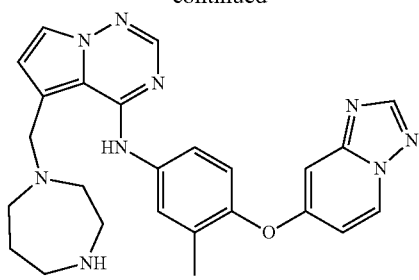
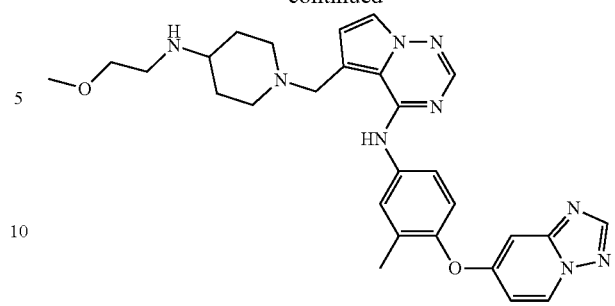
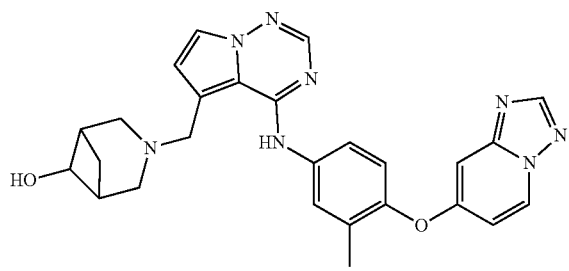
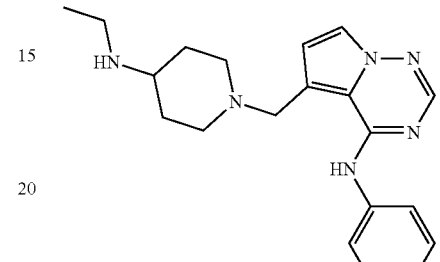
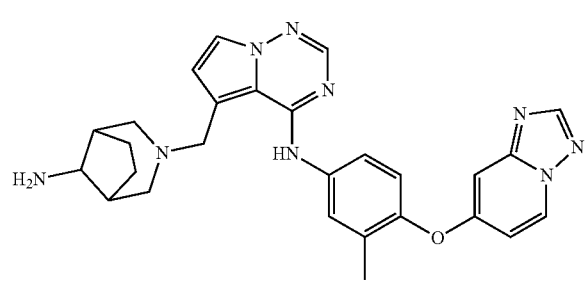
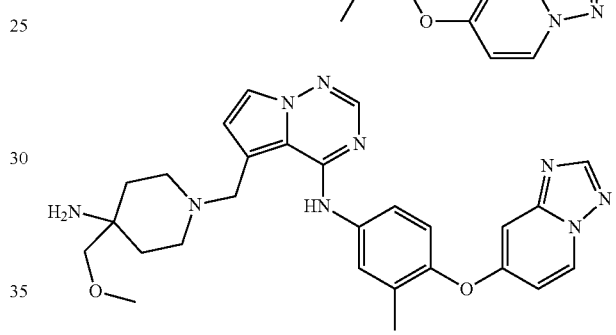
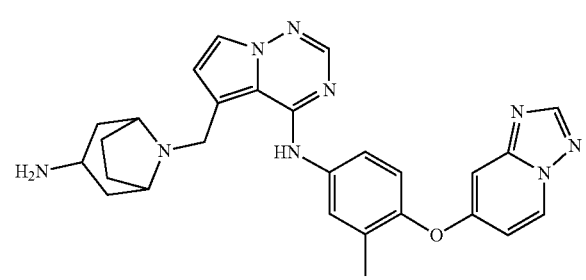
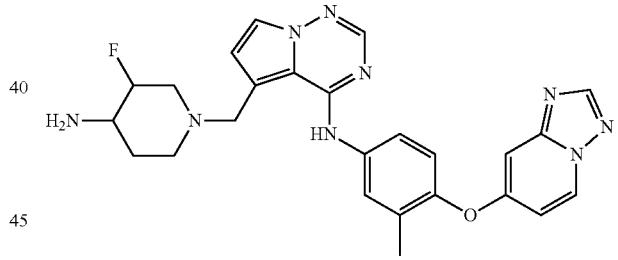
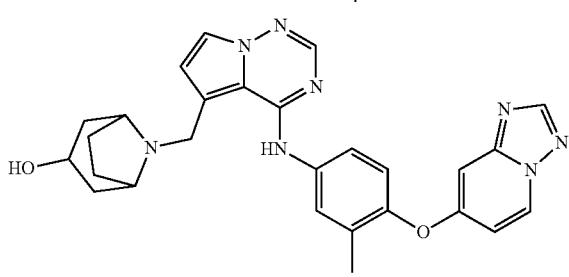
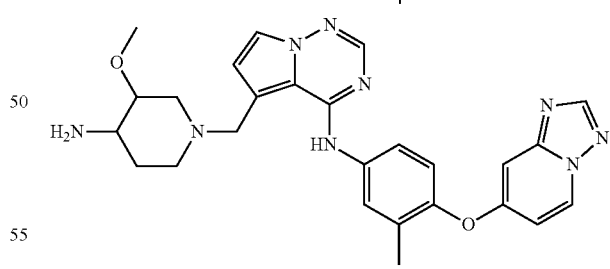
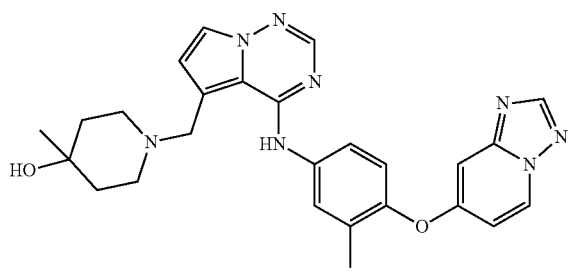
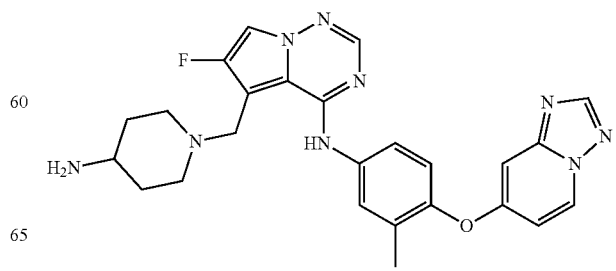

-continued
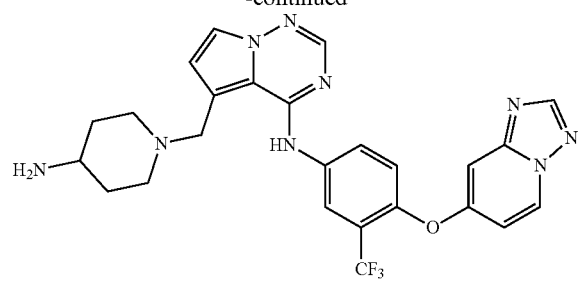
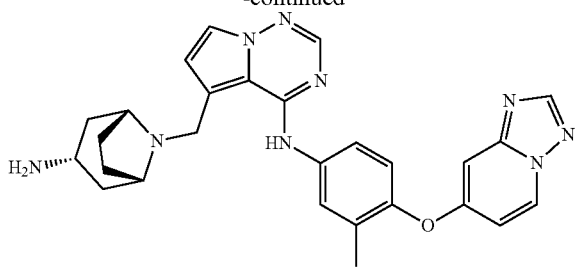
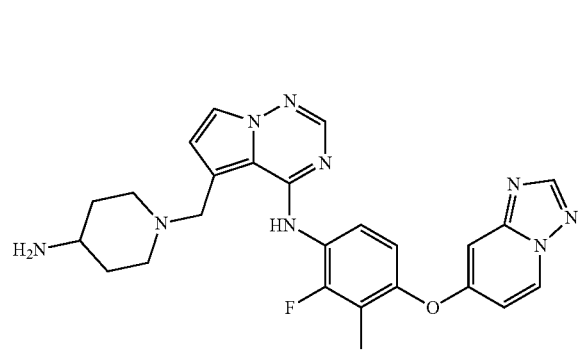
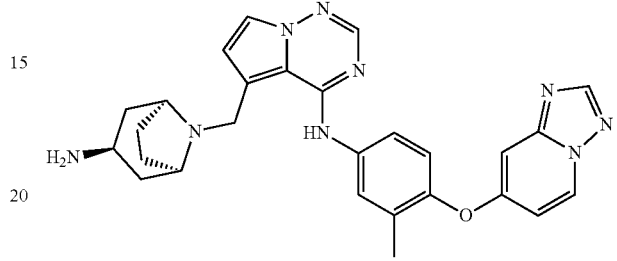
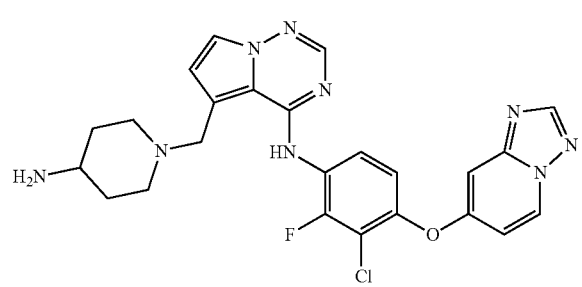
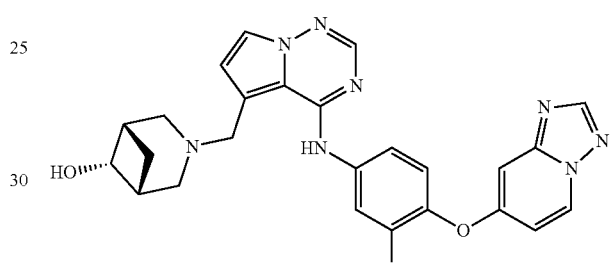
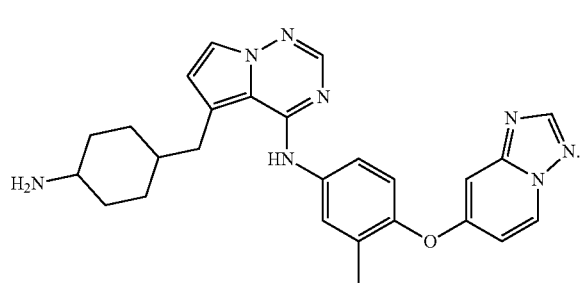 [SMILES: Cc1cc(Nc2ncnn3ccc(CC4CCC(N)CC4)c23)ccc1Oc1ccn2ncnc2c1]
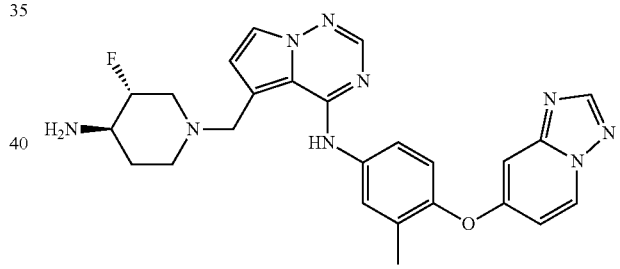
In some embodiments of the present disclosure, the above-mentioned compound, an isomer thereof or a pharmaceutically acceptable salt thereof is selected from
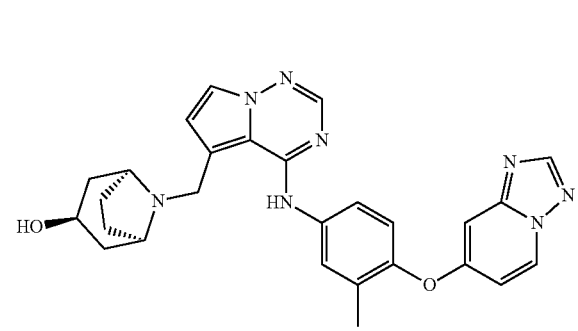
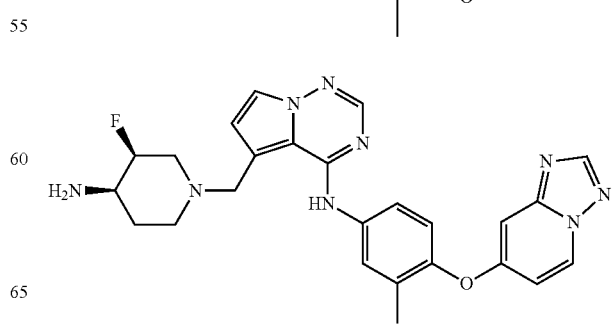

-continued

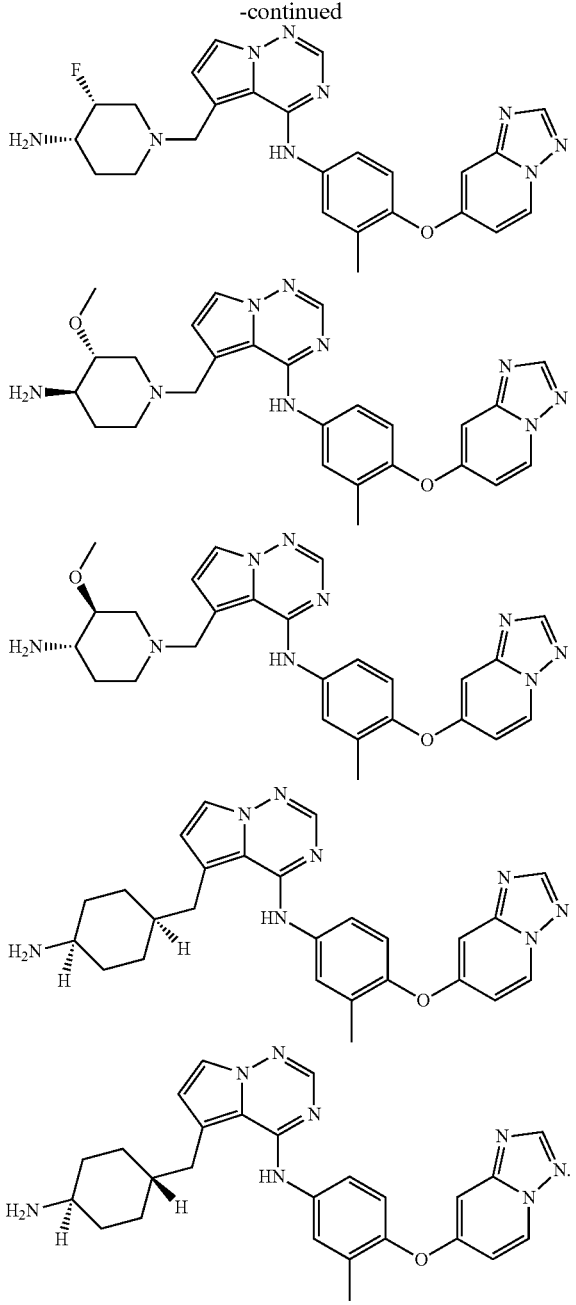

The present disclosure also provides a use of the compound or a pharmaceutically acceptable salt thereof in the manufacture of a medicament for treating diseases related to HER2.

In some embodiments of the present disclosure, the medicament is a medicament for treating breast cancer, gastric cancer, colorectal cancer, esophageal cancer, and lung cancer.

Technical Effects

As a new type of HER2 inhibitor, the compound of the present disclosure can selectively inhibit HER2, and has obvious inhibitory activity on the proliferation of NCI-N87 cells and BT-474 cells; and has an excellent effect of inhibiting tumor growth.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present disclosure. Additional asymmetric carbon atoms may be present in a substituent such as an alkyl group. All these isomers and mixtures thereof are included in the scope of the present disclosure.

Unless otherwise stated, the term "enantiomer" or "optical isomers" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomers" refers to stereoisomers in which molecules have two or more chiral centers and are not mirror images of each other.

Unless otherwise stated, "(D)" or "(+)" means dextrorotatory, "(L)" or means levorotatory, and "(DL)" or "(±)" means racemic.

Unless otherwise stated, the wedge-shaped solid bond (◢) and the wedge-shaped dotted bond (⋯) represent the absolute configuration of a stereoscopic center; the straight solid bond (◢) and straight dotted bond (⋯) represent the relative configuration of a stereoscopic center; the wavy line (∼) represents the wedge-shaped solid bond (◢) or the wedge-shaped dotted bond (⋯); or the wavy line (∼) represents the straight solid bond (◢) and the straight dotted bond (⋯).

Unless otherwise stated, when there is a double bond structure in the compound, such as a carbon-carbon double bond, a carbon-nitrogen double bond, and a nitrogen-nitrogen double bond, and each atom on the double bond is connected to two different substituents (in a double bond containing a nitrogen atom, a lone pair of electrons on the nitrogen atom is regarded as a substituent connected to it), if the atom on the double bond in the compound and its substituent are connected by the wavy line (∼), it represents the (Z) isomer, (E) isomer or a mixture of two isomers of the compound. For example, the following formula (A) indicates that the compound is in the form of a single isomer of formula (A-1) or formula (A-2) or a mixture of two isomers of formula (A-1) and formula (A-2); the following formula (B) indicates that the compound is in the form of a single isomer of formula (B-1) or formula (B-2) or a mixture of two isomers of formula (B-1) and formula (B-2). The following formula (C) indicates that the compound is in the form of a single isomer of formula (C-1) or formula (C-2) or a mixture of two isomers of formula (C-1) and formula (C-2).

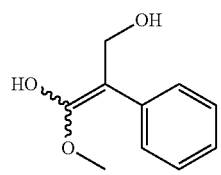

(A)

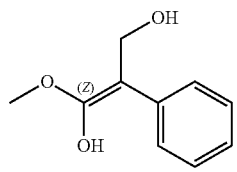

(A-1)

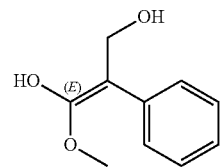

(A-2)

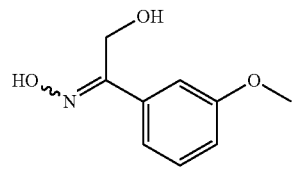

(B)

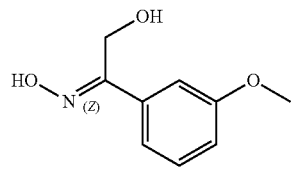

(B-1)

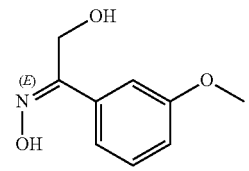

(B-2)

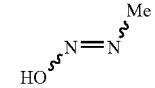

(C)

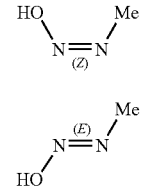

(C-1)

(C-2)

The compounds of the present disclosure may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of bond-forming electrons. A specific example of keto-enol tautomerization is the interconversion between two tautomers, pentane-2,4-dione and 4-hydroxypent-3-en-2-one.

Unless otherwise stated, the terms "rich in one isomer", "isomer enriched", "rich in one enantiomer" or "enantiomerically enriched" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines). The compounds of the present disclosure may contain unnatural proportions of atomic isotopes at one or more of the atoms constituting the compound. For example, the compounds may be radiolabeled with radioactive isotopes, such as tritium ($^3$H), iodine-125 ($^{125}$I) or C-14 ($^{14}$C). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure.

"Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom is substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When one of the variables is selected from a single bond, it means that the two groups to which it is connected are directly connected. For example, when L represents a single bond in A-L-Z, it means that the structure is actually A-Z.

When a substituent is vacant, it means that the substituent does not exist. For example, when X is vacant in A-X, it means that the structure is actually A.

When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

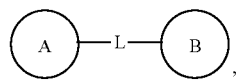

at this situation, -M-W— can connect ring A and ring B in the same direction as the reading order from left to right to form

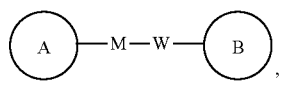

and can also connect ring A and ring B in the opposite direction as the reading order from left to right to form

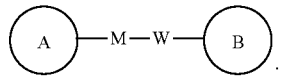

Combinations of the linking groups, substituents, and/or variants thereof are permissible only if such combinations result in stable compounds.

Unless otherwise specified, the term "alkyl" is used to represent a linear or branched saturated hydrocarbon group. In some embodiments, the alkyl is $C_{1-12}$ alkyl; In other embodiments, the alkyl is $C_{1-6}$ alkyl; In other embodiments, the alkyl is $C_{1-3}$ alkyl. It can be monovalent (such as methyl), divalent (such as methyl) or multivalent (such as methine). Examples of alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, etc.

Unless otherwise specified, "alkenyl" is used to represent a linear or branched hydrocarbon group containing one or more carbon-carbon double bonds, which may be located at any position of the group. In some embodiments, the alkenyl is $C_{2-8}$ alkenyl; in other embodiments, the alkenyl is $C_{2-6}$ alkenyl; in other embodiments, the alkenyl is $C_{2-4}$ alkenyl. It can be monovalent, bivalent or multivalent. Examples of alkenyl include, but are not limited to, vinyl, propenyl, butenyl, pentenyl, hexenyl, butadienyl, piperylene, hexadienyl, etc.

Unless otherwise specified, the term "alkoxy" refers to those alkyl groups attached to the rest of the molecule through an oxygen atom. Unless otherwise specified, $C_{1-6}$ alkoxy includes $C_1$, $C_2$, $C_3$, $C_4$, $C_5$ and $C_6$ alkoxy. In some embodiments, the alkoxy is $C_{1-3}$ alkoxy. Examples of alkoxy include, but are not limited to: methoxy, ethoxy, n-propoxy, isopropoxy, n-butoxy, sec-butoxy, tert-butoxy, n-pentoxy and S-pentoxy. Examples of alkoxy include, but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_{33}$, etc.

Unless otherwise specified, the term "—C(=O)—C$_{2-6}$ alkenyl" refers to a connection to C$_{2-6}$ alkenyl through —C(=O)—. Unless otherwise specified, C$_{2-6}$ alkenyl includes —C(=O)—C$_2$ alkenyl, —C(=O)—C$_3$ alkenyl, —C(=O)—C$_4$ alkenyl, —C(=O)—C$_5$ alkenyl and —C(=O)—C$_4$ alkenyl. Examples of C$_{2-6}$ alkenyl include, but are not limited to, —C(=O)—CH=CH$_2$, —C(=O)—CH=CHCH$_3$, —C(=O)—CH$_2$CH=CH$_2$, —C(=O)—(CH$_2$)$_2$CH=CH$_2$, —C(=O)—(CH$_2$)$_3$CH=CH$_2$, —C(=O)—(CH$_2$)$_4$CH=CH$_2$, —C(=O)—CH$_2$CH=C(CH$_3$)$_2$, —C(=O)—CH=C(CH$_3$)$_2$, etc.

Unless otherwise specified, the term "—C(=O)—C$_{2-4}$ alkenyl" refers to a connection to C$_{2-4}$ alkenyl through —C(=O)—. Unless otherwise specified, C$_{2-4}$ alkenyl includes —C(=O)—C$_2$ alkenyl, —C(=O)—C$_3$ alkenyl, —C(=O)—C$_4$ alkenyl, etc. Examples of C$_{2-4}$ alkenyl include, but are not limited to, —C(=O)—CH=CH$_2$, —C(=O)—CH=CHCH$_3$, —C(=O)—CH$_2$CH=CH$_2$, —C(=O)—CH=CHCH$_2$CH$_3$, —C(=O)—CH$_2$CH=CHCH$_3$, —C(=O)—(CH$_2$)$_2$CH=CH$_2$, —C(=O)—CH=C(CH$_3$)$_2$, etc.

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The solvents used in the present disclosure are commercially available. The present disclosure uses the following abbreviations: Pd(dppf)Cl$_2$ represents [1,1'-bis(diphenylphosphino)ferrocene]palladium dichloride; DIBAL-H represents diisobutylaluminum hydride; DIPEA represents N-diisopropylethylamine; Et represents ethyl; DMF-DMA represents N,N-dimethylformamide dimethyl acetal; NMP represents N-methylpyrrolidone; DMF represents N,N-dimethylformamide.

Compounds are named according to conventional naming principles in the field or using ChemDraw® software, and commercially available compounds are named using supplier catalog names.

DETAILED DESCRIPTION OF EMBODIMENTS

The present disclosure will be described in detail with the following examples, but not imply any adverse limitation to the present disclosure. The present disclosure has been described in detail herein, and the specific embodiments thereof are also disclosed therein. For a person skilled in the art, without departing from the spirit and scope of the present disclosure, all the variations and improvements made to the specific embodiments of the present disclosure would have been obvious.

Intermediate 1

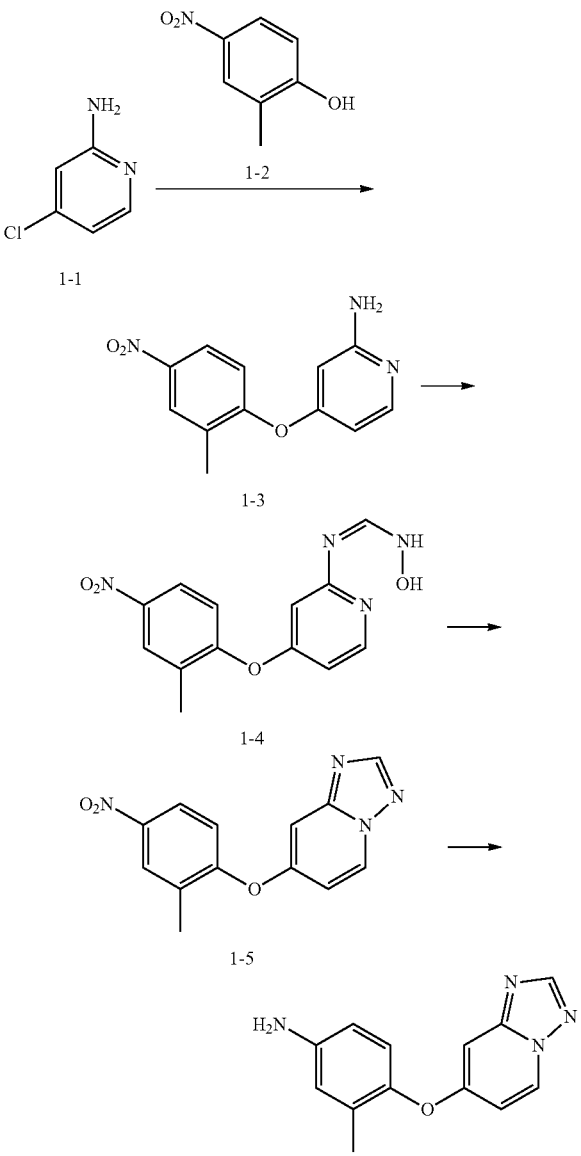

Intermediate 1

Step 1

Compound 1-1 (100.00 g, 653.02 mmol, 1.50 eq) and compound 1-2 (56.00 g, 435.59 mmol, 1.00 eq) were dissolved in chlorobenzene (400 mL), and pyridine (6.89 g, 87.07 mmol, 7.00 mL, 0.20 eq) is added. The reaction mixture was stirred at 135° C. for 72 hours under nitrogen protection. TLC (petroleum ether:ethyl acetate=1:1) detected that the reaction was completed. After the reaction mixture was cooled to room temperature, a solid was precipitated. The mixture was filtered, and the filter cake was washed with ethyl acetate (50 mL*5). The resulting solid was concentrated under reduced pressure and evaporated to dryness to obtain compound 1-3. $^1$H NMR (400 MHz, DMSO-d$_6$) δ 8.39 (d, J=2.8 Hz, 1H), 8.23 (dd, J=2.4, 8.4 Hz, 1H), 8.02 (d, J=7.2 Hz, 1H), 8.00-7.89 (m, 2H), 7.52 (d, J=8.8 Hz, 1H), 6.67 (dd, J=2.0, 6.8 Hz, 1H), 6.16 (s, 1H), 2.28 (s, 3H).

Step 2

Compound 1-3 (70.00 g, 285.44 mmol, 1.00 eq) was dissolved in isopropanol (400 mL), and DMF-DMA (68.03 g, 570.88 mmol, 76.00 mL, 2.00 eq) was added. The reaction mixture was reacted at 90° C. for 4 hours and then cooled to 50° C. Hydroxylamine hydrochloride (29.75 g, 428.16 mmol, 1.50 eq) was added, and the reaction mixture was reacted at 50° C. for 16 hours. LCMS detected the reaction, and the reaction was completed, and a solid was precipitated. The reaction mixture was filtered, and the filter cake was washed with water (100 mL*3), concentrated and evaporated to dryness to obtain compound 1-4. $^1$H NMR (400 MHz, DMSO-$d_6$) δ 10.07 (s, 1H), 9.36 (d, J=9.6 Hz, 1H), 8.33 (d, J=2.8 Hz, 1H), 8.16 (dd, J=2.8, 8.8 Hz, 1H), 8.10 (d, J=5.6 Hz, 1H), 7.83 (d, J=10.0 Hz, 1H), 7.31 (d, J=9.2 Hz, 1H), 6.61 (d, J=2.0 Hz, 1H), 6.55 (dd, J=2.4, 5.6 Hz, 1H), 2.28 (s, 3H). MS: m/z 289.1 [M+H]$^+$.

Step 3

Compound 1-4 (40.00 g, 138.76 mmol, 1.00 eq) was dissolved in tetrahydrofuran (120 mL). The reaction mixture was heated to 50° C., and then trifluoroacetic anhydride (32.06 g, 152.64 mmol, 21.23 mL, 1.10 eq) diluted with tetrahydrofuran (60 mL) was slowly added dropwise. After the dropwise addition, LCMS and TLC (dichloromethane:methanol=30:1) detected the reaction, and the reaction was completed. The reaction mixture was concentrated to remove most of the solvent, and then slowly poured into an ice-cold 1 M sodium hydroxide aqueous solution (1000 mL), and a solid was precipitated. The reaction mixture was filtered, and the filter cake was washed with water (100 mL*2) and ethyl acetate (100 mL*2) and concentrated to obtain compound 1-5. $^1$H NMR (400 MHz, DMSO-$d_6$) δ 9.02 (d, J=7.6 Hz, 1H), 8.47 (s, 1H), 8.33 (s, 1H), 8.16-8.11 (m, 1H), 7.37-7.25 (m, 2H), 7.11 (dd, J=2.0, 7.6 Hz, 1H), 2.36 (s, 3H). MS: m/z 270.9 [M+H]$^+$.

Step 4

Compound 1-5 (33.00 g, 122.11 mmol, 1.00 eq) was dissolved in a mixed solution of tetrahydrofuran (120 mL) and methanol (300 mL), and wet Pd/C (5.00 g, 10% purity) was added. The reaction mixture was degassed under vacuum and purged with H$_2$ several times and hydrogenated at 25° C., 20 psi for 16 hours. LCMS detected the reaction, and the reaction was completed. The reaction mixture was directly filtered (diatomite filter aid), and the filtrate was concentrated to obtain intermediate 1. $^1$H NMR (400 MHz, DMSO-$d_6$) δ 8.87 (d, J=7.6 Hz, 1H), 8.34 (s, 1H), 6.95 (dd, J=2.8, 7.6 Hz, 1H), 6.82 (d, J=8.4 Hz, 1H), 6.62 (d, J=2.4 Hz, 1H), 6.54 (d, J=2.4 Hz, 1H), 6.49 (dd, J=2.4, 8.4 Hz, 1H), 5.12 (s, 2H), 1.99 (s, 3H). MS: m/z 241.0 [M+H]$^+$.

Intermediate 2

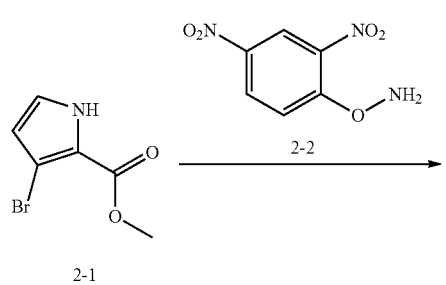

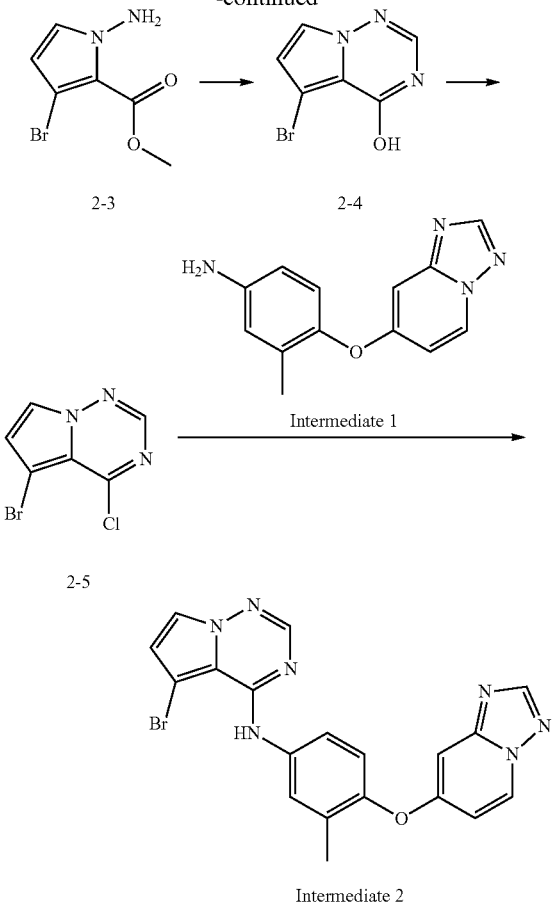

Step 1

Sodium hydrogen (1.27 g, 31.86 mmol, 60% purity, 1.30 eq) was added to a mixed solvent of N,N-dimethylformamide (90 mL) and tetrahydrofuran (450 mL) in batches at 0° C. Compound 2-1 (5.00 g, 24.51 mmol, 1.00 eq) was added in batches at 0° C. and stirred at 15° C. for 1 hour. Then compound 2-2 (5.86 g, 29.41 mmol, 1.20 eq) was added in batches at 0° C. and stirred at 15° C. for 16 hours. TLC (petroleum ether:ethyl acetate=5:1) and LCMS detected that the reaction was completed. The reaction mixture was cooled to 0° C., quenched with a saturated aqueous ammonium chloride solution (50 mL), then diluted with water (1 L) and extracted with ethyl acetate (200 mL*2). The organic phase was washed with saturated brine (200 mL*2), dried with anhydrous sodium sulfate and filtered. The filtrate was concentrated under reduced pressure to obtain compound 2-3. $^1$H NMR (400 MHz, DMSO-$d_6$) δ 7.06 (d, J=3.2 Hz, 1H), 6.30 (s, 2H), 6.18 (d, J=3.2 Hz, 1H), 3.79 (s, 3H).

Step 2

Compound 2-3 (42 g, 191.75 mmol, 1.00 eq) was dissolved in isopropanol (420 mL), and then formamidine acetate (39.93 g, 383.50 mmol, 2.00 eq) was added. The reaction mixture was reacted at 80° C. for 16 hours. TLC (petroleum ether:ethyl acetate=1:1) detected that the reaction was almost completed. The reaction mixture was cooled to room temperature, diluted with water (420 mL) and filtered. The filter cake was washed with water, washed with petroleum ether, concentrated under reduced pressure and evaporated to dryness to obtain compound 2-4. $^1$H NMR (400 MHz, DMSO-$d_6$) δ 11.68 (br s, 1H), 7.83 (s, 1H), 7.60 (d, J=3.2 Hz, 1H), 6.65 (d, J=3.2 Hz, 1H).

Step 3

Compound 2-4 (25.00 g, 116.81 mmol, 1.00 eq) was dissolved in 1,4-dioxane (500 mL), and phosphorus oxychloride (179.11 g, 1.17 mol, 108.55 mL, 10.00 eq) was added, The resulting mixture was heated to 110° C. and reacted for 4 hours. TLC (petroleum ether:ethyl acetate=1:1) and LCMS detected that the reaction was completed. The reaction mixture was cooled to room temperature and concentrated under reduced pressure to remove most of the solvent. The residue was poured into an ice-cold saturated sodium bicarbonate aqueous solution (500 mL) and extracted with ethyl acetate (200 mL*2). The organic phase was washed with saturated sodium bicarbonate aqueous solution (200 mL) and saturated brine (200 mL*2) successively, dried over anhydrous sodium sulfate and filtered. The filtrate was concentrated under reduced pressure to obtain compound 2-5. $^1$H NMR (400 MHz, CHCl$_3$-d) δ 8.19 (s, 1H), 7.82 (d, J=2.8 Hz, 1H), 7.03 (d, J=2.8 Hz, 1H).

Step 4

Compound 2-5 (13.00 g, 55.92 mmol, 1.00 eq) and intermediate 1 (8.06 g, 33.55 mmol, 0.60 eq) were dissolved in isopropanol (100 mL), and the reaction mixture was reacted at 80° C. for 12 hours. TLC (petroleum ether:ethyl acetate=1:1) and LCMS detected that the reaction was completed. The reaction mixture was cooled to room temperature, and filtered. The filter cake was washed with a small amount of ethyl acetate, washed with petroleum ether, concentrated under reduced pressure and dried to obtain intermediate 2. $^1$H NMR (400 MHz, DMSO-d$_6$) δ 9.00 (d, J=7.6 Hz, 1H), 8.52 (s, 1H), 8.06 (s, 1H), 7.89 (d, J=2.8 Hz, 1H), 7.81-7.70 (m, 2H), 7.25 (d, J=9.6 Hz, 1H), 7.10 (dd, J=2.8, 7.6 Hz, 1H), 6.96 (d, J=2.8 Hz, 1H), 6.86 (d, J=2.8 Hz, 1H), 2.19 (s, 3H)

Intermediate 3

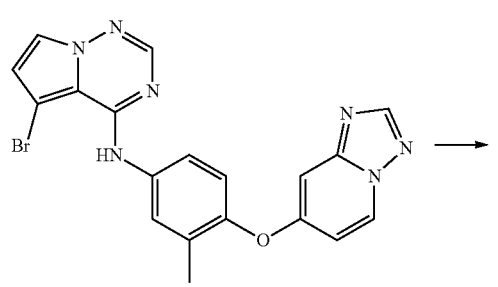

Intermediate 2

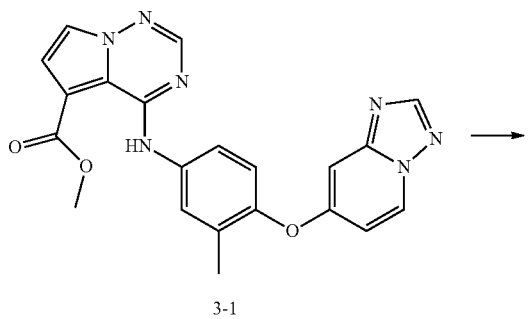

3-1

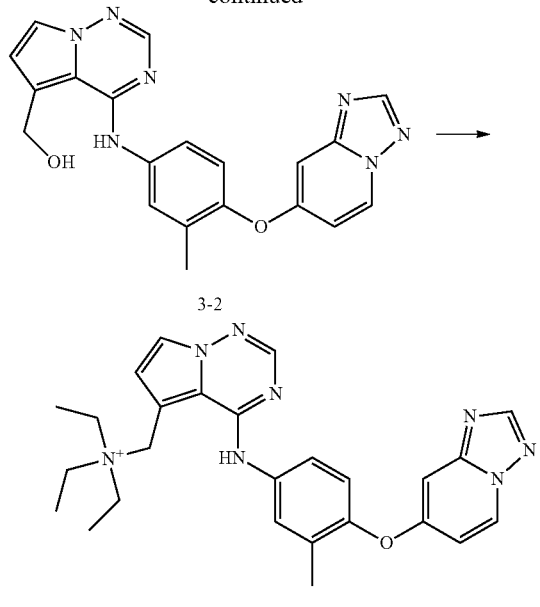

Intermediate 3

Step 1

Intermediate 2 (1.00 g, 2.29 mmol, 1.00 eq) was dissolved in a mixed solvent of N,N-dimethylformamide (10 mL) and methanol (20 mL), and then Pd(dppf)Cl$_2$ (335 mg, 458.44 μmol, 0.20 eq) and triethylamine (696, 6.88 mmol, 957 μL, 3.00 eq) were added under nitrogen protection. The reaction mixture was subjected to a carbonyl insertion reaction at 80° C., 50 psi under carbon monoxide atmosphere for 48 hours. TLC (petroleum ether:ethyl acetate=1:1) and LCMS detected that the reaction was completed. The reaction mixture was cooled to room temperature, diluted with water (100 mL) and extracted with ethyl acetate (50 mL*2). The organic phase was washed with saturated brine (40 mL*2), dried over anhydrous sodium sulfate, filtered and concentrated. The concentrate was slurried with a mixed solvent of petroleum ether and ethyl acetate (10 mL: 10 mL) and filtered. The filter cake was subjected to column chromatography (12 g silica gel column, mobile phase: ethyl acetate/petroleum ether with polarity of 0 to 60%, flow rate: 30 mL/min), the eluent was concentrated and then slurried with a mixed solvent of petroleum ether and ethyl acetate (10 mL: 10 mL), filtered and dried under vacuum to obtain intermediate 3-1. $^1$H NMR (400 MHz, DMSO-d$_6$) δ 12.03 (s, 1H), 8.93 (d, J=7.6 Hz, 1H), 8.39 (s, 1H), 8.27 (s, 1H), 7.90-7.81 (m, 3H), 7.30-7.22 (m, 2H), 7.03 (d, J=5.6 Hz, 1H), 6.85-6.79 (m, 1H), 3.96 (s, 3H), 2.21 (s, 3H)

Step 2

Compound 3-1 (200.0 mg, 481.46 μmol, 1.00 eq) was dissolved in dichloromethane (4 mL), and DIBAL-H (1 M, 963 μL, 2.00 eq) was added at minus 78° C. under nitrogen protection. The reaction mixture was naturally heated to 0° C. and reacted at 0° C. for 2 hours and then reacted at 25° C. for 16 hours under nitrogen protection. TLC (petroleum ether:ethyl acetate=1:1) detected the reaction, and the reaction conversion was not completed with nearly a half was converted to the product. The reaction mixture was cooled to 0° C., quenched with sodium sulfate decahydrate (0.5 g), and filtered. The filter cake was washed with ethyl acetate, and the filtrate was concentrated under reduced pressure and subjected to column chromatography (12 g silica gel column, mobile phase: ethyl acetate/petroleum ether with polarity of 0 to 85%, flow rate: 35 mL/min) to obtain intermediate 3-2. $^1$H NMR (400 MHz, DMSO-d$_6$) δ 11.04 (s, 1H), 8.93 (d, J=7.6 Hz, 1H), 8.38 (s, 1H), 8.02 (s, 1H), 7.85-7.76 (m, 2H), 7.69 (d, J=2.4 Hz, 1H), 7.23 (d, J=8.4 Hz, 1H), 7.02 (dd, J=2.4, 7.6 Hz, 1H), 6.95 (br s, 1H), 6.80 (d, J=2.4 Hz, 1H), 6.67 (d, J=2.4 Hz, 1H), 4.90 (d, J=2.8 Hz, 2H), 2.22 (s, 3H). MS: m/z 388.1 [M+H]$^+$.

Step 3

Compound 3-2 (250 mg, 645.34 μmol, 1.00 eq) was dissolved in dichloromethane (10 mL), and then thionyl chloride (86.19 g, 452.08 mmol, 1.10 eq) was added dropwise at 0° C. The reaction mixture was stirred at 20° C. for 0.5 hour, and then triethylamine (588 mg, 5.81 mmol, 808 μL, 9.00 eq) was added at 0° C. The reaction mixture was stirred at 20° C. for 16 hours. LCMS showed that the reaction was completed. The reaction mixture was directly concentrated under reduced pressure and evaporated to dryness to obtain compound intermediate 3. MS: m/z [M+H]$^+$.

Intermediate 4

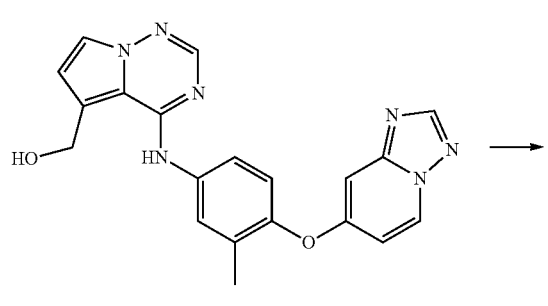

3-2

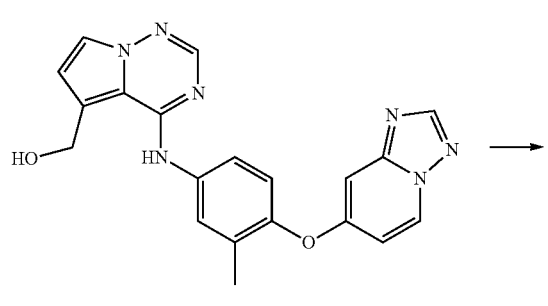

Intermediate 4

Compound 3-2 (500 mg, 1.29 mmol, 1.00 eq) was dissolved in dichloromethane (10 mL), and thionyl chloride (492.0 mg, 4.14 mmol, 300.00 μL, 3.20 eq) was added at 0° C. The reaction mixture was stirred at 0° C. for 2 hours. After the reaction was completed, the reaction mixture was directly concentrated to dryness to obtain intermediate 4.

Intermediate 5

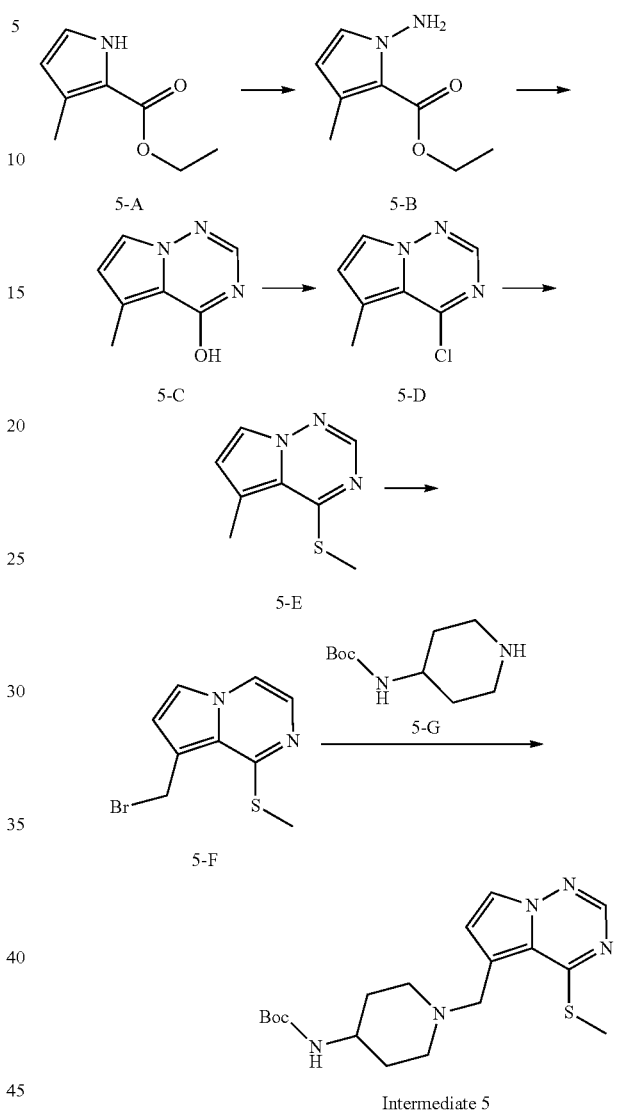

Step 1

Sodium hydrogen (6.74 g, 168.40 mmol, 60% purity, 1.53 eq) was added to anhydrous DMF (170 mL) at 0° C., and then compound 5-A (16.84 g, 109.94 mmol, 1.00 eq) was added in batches. The reaction mixture was reacted at 20° C. for 1 hour. Then 2,4-dinitrophenylhydroxylamine (26.27 g, 131.92 mmol, 1.20 eq) was added slowly to the above-mentioned reaction mixture at 0° C. and stirred at 20° C. for 22 hours. LCMS detected that the reaction was completed. The reaction was quenched by adding saturated aqueous ammonium chloride solution (50 mL) at 0° C. The reaction mixture was filtered, and the filtrate was concentrated under reduced pressure to remove DMF, diluted with water (200 mL) and extracted with ethyl acetate (300 mL*3). The combined organic phase was washed with water (100 mL) and saturated brine (100 mL), dried over anhydrous sodium sulfate and filtered. The filtrate was concentrated under reduced pressure and evaporated to dryness to obtain a crude product of compound 5-B. MS: m/z 168.8 [M+H]$^+$.

Step 2

Formamidine acetate (18.94 g, 181.93 mmol, 1.7 eq) was added to a solution of compound 5-B (18 g, 107.02 mmol, 1.00 eq) in isopropanol (100 mL), and the reaction mixture was reacted at 90° C. for 20 hours. After LCMS detected that the reaction was completed, the reaction mixture was cooled to room temperature, concentrated under reduced pressure and evaporated to dryness to obtain a crude product. The crude product was purified by column chromatography (ISCO®; 180 g SepaFlash® fast silica gel column, mobile phase: 0 to 100% ethyl acetate/petroleum ether, flow rate: 85 mL/min) to obtain compound 5-C. $^1$H NMR (DMSO-d$_6$) δ 11.35 (s, 1H), 7.69 (d, J=4.0 Hz, 1H), 7.42 (d, J=2.4 Hz, 1H), 6.34 (d, J=2.5 Hz, 1H), 2.41 (s, 3H). MS: m/z 149.8 [M+H]$^+$.

Step 3

Compound 5-C (6.00 g, 40.23 mmol, 1.00 eq) was added to anhydrous toluene (60 mL), and phosphorus oxychloride (8.02 g, 52.30 mmol, 4.86 mL, 1.30 eq) and N,N-diisopropylethylamine (4.16 g, 32.18 mmol, 5.61 mL, 0.80 eq) were sequentially added slowly at room temperature. The reaction mixture was heated to 110° C. and stirred for 16 hours under nitrogen protection. LCMS and TLC detected that the reaction was completed. The reaction mixture was cooled to room temperature, poured into an ice-cold saturated sodium bicarbonate aqueous solution (100 mL), and extracted with ethyl acetate (50 mL*2). The organic phase was washed with saturated sodium bicarbonate aqueous solution (50 mL) and saturated brine (50 mL*2), dried over anhydrous sodium sulfate and filtered. The filtrate was concentrated under reduced pressure to obtain compound 5-D. MS: m/z 167.8 [M+H]$^+$.

Step 4

Compound 5-D (8.00 g, 47.73 mmol, 1.00 eq) was dissolved in dry tetrahydrofuran (65 mL), and an aqueous solution of sodium thiomethoxide (26.77 g, 76.37 mmol, 24.33 mL, 20% purity, 1.60 eq) was added at 0° C. The reaction mixture was then stirred at 25° C. for 1 hour. LCMS showed that the reaction was completed. The reaction mixture was diluted with water (200 mL), and extracted with ethyl acetate (100 mL*2). The organic phase was washed with saturated brine (50 mL*2), dried over anhydrous sodium sulfate and filtered. The filtrate was directly concentrated under reduced pressure to obtain a crude product. The crude product was separated by column chromatography (ISCO®; 40 g SepaFlash® fast silica gel column, mobile phase: 0 to 6.8% ethyl acetate/petroleum ether, flow rate: 40 mL/min) to obtain compound 5-E. $^1$H NMR (400 MHz, CDCl$_3$-d) δ 7.95 (s, 1H), 7.46 (d, J=2.4 Hz, 1H), 6.48 (d, J=2.4 Hz, 1H), 2.56 (s, 3H), 2.52 (s, 3H).

Step 5

Compound 5-E (2.00 g, 11.16 mmol, 1.00 eq), N-bromosuccinimide (2.18 g, 12.27 mmol, 1.10 eq) and azobisisobutyronitrile (183 mg, 1.12 mmol, 0.10 eq) were put into a dry and clean 100 mL reaction flask together and purged with nitrogen three times. Then carbon tetrachloride (40 mL) was added quickly. The resulting reaction mixture was directly put into 100° C. oil bath under nitrogen protection without pre-stirring and stirred for 1.5 hours. LCMS showed that the reaction was completed. The reaction mixture was cooled to room temperature and filtered. The filtrate was directly concentrated to dryness under reduced pressure to obtain compound 5-F.

Step 6

Compound 5-F (4.50 g, 17.43 mmol, 1.00 eq) was dissolved in 1,2-dichloroethane (45 mL), and compound 5-G (3.67 g, 18.30 mmol, 1.05 eq) was added at 0° C. Then the reaction mixture was stirred at 25° C. for 1 hour. LCMS showed that the reaction was completed. The reaction mixture was filtered, and the filtrate was directly concentrated under reduced pressure to obtain a crude product. The crude product was separated by column chromatography separated (ISCO®; 40 g SepaFlash® fast silica gel column, mobile phase: 0 to 100% ethyl acetate/petroleum ether, flow rate: 40 mL/min) to obtain intermediate 5. $^1$H NMR (400 MHz, CDCl$_3$-d) δ 8.02 (s, 1H), 7.52 (d, J=2.8 Hz, 1H), 6.66 (d, J=2.4 Hz, 1H), 4.34 (br s, 1H), 3.76 (s, 2H), 3.42 (br s, 1H), 2.83 (br d, J=11.6 Hz, 2H), 2.56 (s, 3H), 2.11 (br t, J=10.8 Hz, 2H), 1.85 (br d, J=11.6 Hz, 2H), 1.37 (s, 9H), 1.36-1.29 (m, 2H).

Intermediate 6

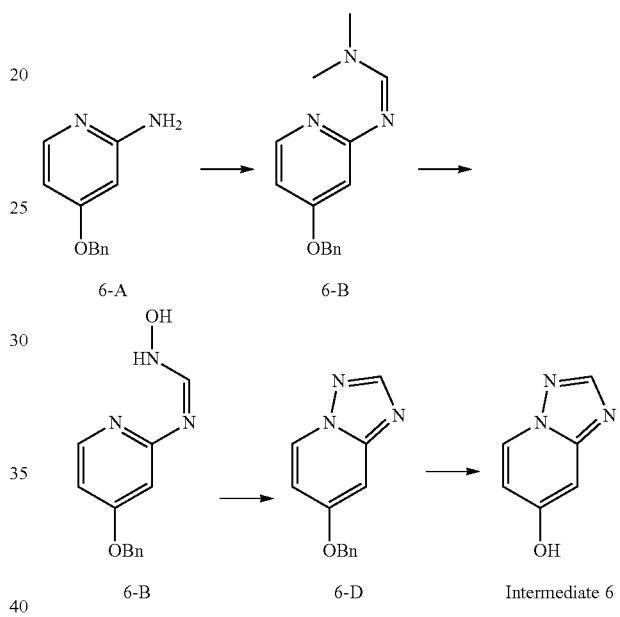

Step 1

Compound 6-A (25.00 g, 124.85 mmol, 1.00 eq) and DMF-DMA (22.43 g, 188.19 mmol, 1.51 eq) were dissolved in ethanol (300 mL), and trifluoroacetic acid (1.54 g, 13.51 mmol, 0.11 eq) was added. Then the reaction mixture was stirred at 50° C. for 16 hours. LCMS showed that the reaction was completed. The reaction mixture was evaporated to dryness under reduced pressure to obtain compound 6-B. MS: m/z 255.7 [M+H]$^+$.

Step 2

Compound 6-B (31.80 g, 124.55 mmol, 1.00 eq) and hydroxylamine hydrochloride (10.40 g, 149.66 mmol, 1.2 eq) were dissolved in a mixed solvent of isopropanol (100 ml) and tetrahydrofuran (25 ml), and then the reaction mixture was stirred at 50° C. for 8 hours. LCMS showed that the reaction was completed. The reaction mixture was subjected to rotary evaporation to dryness directly, and the resulting solid was slurried with a mixed solvent of tetrahydrofuran (300 ml) and ethyl acetate (100 ml). The mixture was filtered under suction, and the resulting filtrate was concentrated under reduced pressure to obtain compound 6-C. MS: m/z 244.1 [M+H]$^+$.

Step 3

Compound 6-C (31.00 g, 127.44 mmol, 1.00 eq) was dissolved in tetrahydrofuran (500 ml), and trifluoroacetic anhydride (29.44 g, 140.18 mmol, 19.50 mL, 1.1 eq) was added dropwise slowly at 0° C. Then the reaction mixture was stirred and reacted at 25° C. for 16 hours. The reaction mixture was concentrated to 100 ml in vacuum, and the concentrated solution was poured into 1.5 L of 1M/L ice NaOH solution, and stirred for 2 hours. The resulting mixture was extracted with ethyl acetate (800 ml*3), and the organic layers were combined and washed with saturated brine (1000 ml), dried over anhydrous sodium sulfate and filtered. The filtrate was concentrated under reduced pressure to obtain a crude product of compound 6-D. MS: m/z 225.8 $[M+H]^+$.

Step 4

Compound 6-D (15.00 g, 66.59 mmol, 1.00 eq) was dissolved in a mixed solvent of tetrahydrofuran (100 mL) and methanol (200 mL), and Pd/C (1.00 g, 10% purity) was added under nitrogen protection. Then the reaction mixture was degassed under vacuum and purged with $H_2$ for three times and stirred at 25° C. for 16 hours (15 psi). TLC detected that the reaction was completed. The reaction mixture was filtered (diatomite filter aid), and the filtrate was concentrated and separated by column chromatography (ISCO®; 80 g SepaFlash® fast silica gel column, mobile phase: 0 to 10% methanol/dichloromethane, flow rate: 60 mL/min) to obtain intermediate 6. $^1$H NMR (400 MHz, DMSO-$d_6$) δ 10.86 (brs, 1H), 8.71 (d, J=7.2 Hz, 1H), 8.24 (s, 1H), 6.90 (d, J=2.4 Hz, 1H), 6.74 (dd, J=2.4, 7.2 Hz, 1H).

Intermediate 7 ether:ethyl acetate=1:1) detected that the reaction was completed. The reaction mixture was diluted with water (500 mL), and then extracted with ethyl acetate (100 mL*3). The organic phases were combined, washed with saturated brine (100 mL), dried over anhydrous sodium sulfate and concentrated to obtain a crude product. The crude product was separated by column chromatography (ISCO®; 80 g SepaFlash® fast silica gel column, mobile phase: 0 to 40% ethyl acetate/petroleum ether, flow rate: 60 mL/min) to obtain compound 7-B. MS: m/z 289.1 $[M+H]^+$.

Step 2

Compound 7-B (0.84 g, 2.91 mmol, 1.00 eq) was dissolved in methanol (10 mL) and water (5 mL), and iron powder (813.7 mg, 14.57 mmol, 5.00 eq) and ammonium chloride (779.5 mg, 14.57 mmol, 5.00 eq) were added. The reaction mixture was stirred at 65° C. for 10 hours. LCMS detected that the reaction was completed, and the reaction mixture was filtered and concentrated to remove methanol. The resulting mixture was adjusted to neutral with saturated sodium bicarbonate (100 mL), and then extracted with ethyl acetate (100 mL*3). The organic phases were combined, washed with saturated brine (50 mL), dried over anhydrous sodium sulfate and concentrated to obtain intermediate 7. MS: m/z 259.1 $[M+H]^+$.

Intermediate 8

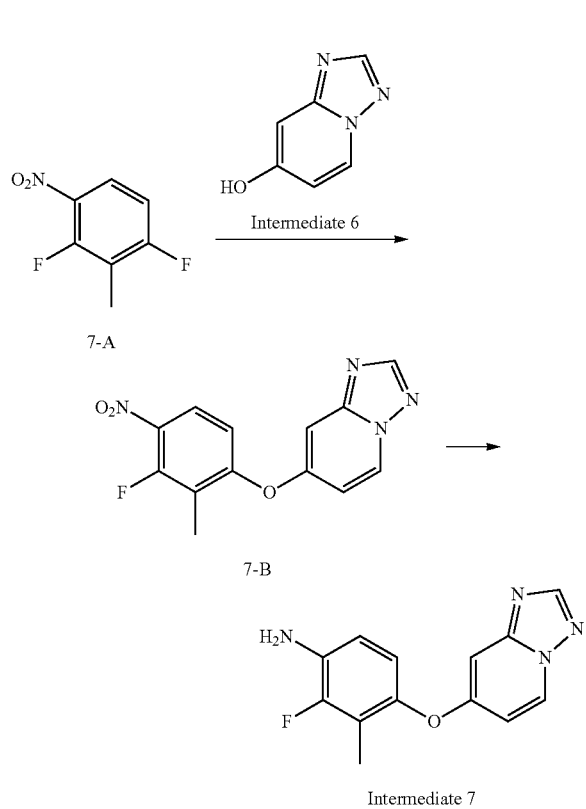

Intermediate 7

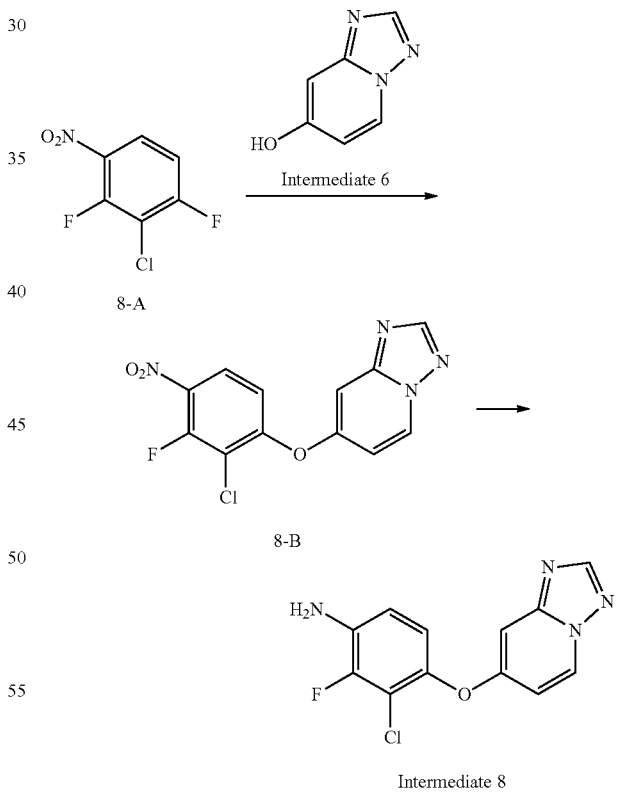

Intermediate 8

Step 1

Compound 7-A (4.36 g, 25.16 mmol, 1.00 eq) and intermediate 6 (3.40 g, 25.16 mmol, 1.00 eq) were dissolved in N,N-dimethylformamide (40 mL), and potassium carbonate (10.43 g, 75.49 mmol, 3.00 eq) was added. The reaction mixture was stirred at 100° C. for 2 hours. TLC (petroleum Step 1

Compound 8-A (1.00 g, 7.40 mmol, 1.00 eq) and intermediate 6 (1.43 g, 7.40 mmol, 1.00 eq) were dissolved in N,N-dimethylformamide (10 mL), and potassium carbonate (3.07 g, 22.20 mmol, 3.00 eq) was added. The reaction mixture was stirred at 25° C. for 3 hours. TLC detected that the reaction was completed. The reaction mixture was diluted with water (200 mL), and then extracted with ethyl acetate (100 mL*3). The organic phases were combined, washed with saturated brine (50 mL), dried over anhydrous sodium sulfate, and concentrated to obtain a yellow oily product. The product was further separated and purified by column chromatography (ISCO®; 24 g SepaFlash® fast silica gel column, mobile phase: 0 to 50% ethyl acetate/petroleum ether, flow rate: 20 mL/min) to obtain compound 8-B. $^1$H NMR (400 MHz, DMSO-d$_6$) δ 9.08 (d, J=7.6 Hz, 1H), 8.51 (s, 1H), 8.22 (dd, J=8.4, 9.2 Hz, 1H), 7.57 (d, J=2.0 Hz, 1H), 7.34 (dd, J=2.0, 9.4 Hz, 1H), 7.22 (dd, J=2.4, 7.6 Hz, 1H).

Step 2

Compound 8-B (0.35 g, 1.13 mmol, 1.00 eq) was dissolved in a mixed solvent of ethanol (10 mL) and water (5 mL), and iron powder (316.63 mg, 5.67 mmol, 5.00 eq) and ammonium chloride (303.28 mg, 5.67 mmol, 5.00 eq) were added. The reaction mixture was stirred at 75° C. for 3 hours. LCMS showed that the reaction was completed. The reaction mixture was filtered (diatomite filter aid), and the filtrate was concentrated to remove ethanol, diluted with water (100 mL), and then extracted with ethyl acetate (100 mL*3). The organic phases were combined, washed with saturated brine (50 mL), dried over anhydrous sodium sulfate and concentrated to obtain intermediate 8. MS: m/z 278.8 [M+H]$^+$.

Example 1

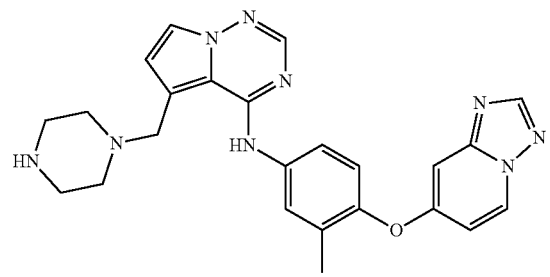 [SMILES: Cc1cc(Nc2ncnn3ccc(CN4CCNCC4)c23)ccc1Oc1ccn2ncnc2c1]

Example 1

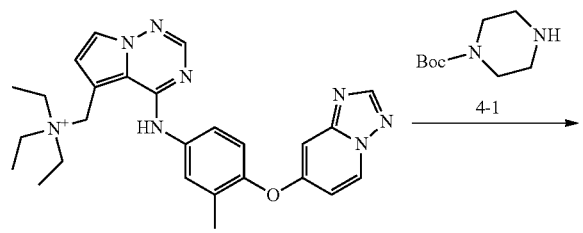

Intermediate 3

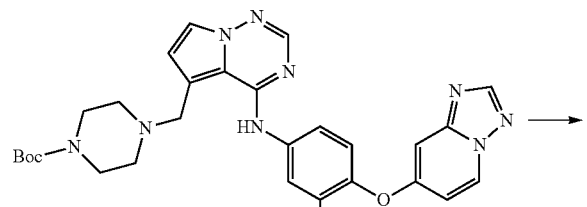

4-2

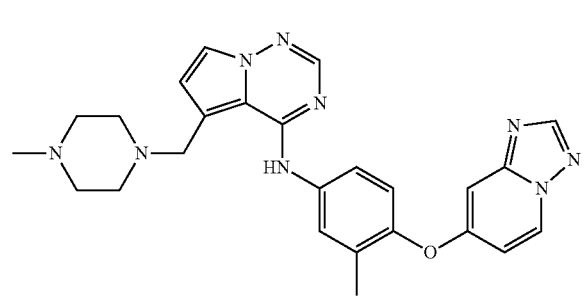 [SMILES: Cc1cc(Nc2ncnn3ccc(CN4CCN(C)CC4)c23)ccc1Oc1ccn2ncnc2c1]

Example 1

Step 1

Intermediate 3 (400 mg, 848.22 μmol, 1.00 eq), compound 4-1 (79 mg, 424.11 μmol, 35 μL, 0.50 eq) and DIPEA (55 mg, 424.11 μmol, 74 μL, 0.50 eq) were added to acetonitrile (4 mL) and stirred at 70° C. for 2 hours. LCMS and TLC (petroleum ether:ethyl acetate=1:1) detected that the reaction was completed. The reaction mixture was cooled to room temperature, diluted with water (50 mL), and extracted with ethyl acetate (20 mL*3). The organic phases were combined, washed with saturated brine (20 mL*2) and dried over anhydrous sodium sulfate. The filtrate was concentrated under reduced pressure and separated by preparative thin layer chromatography (petroleum ether:ethyl acetate=1:1) to obtain 4-2. MS: m/z 556.1 [M+H]$^+$.

Step 2

4-2 (35 mg, 62.99 μmol, 1.00 eq) was dissolved in dichloromethane (5 mL), and then trifluoroacetic acid (1.54 g, 13.51 mmol, 1 mL, 214.41 eq) was added. The reaction mixture was stirred at 20° C. for 4 hours. LCMS showed that the reaction was completed. The reaction mixture was directly concentrated under reduced pressure and evaporated to dryness to obtain a crude product. The crude product was diluted with methanol (3 mL), and separated by preparative HPLC (formic acid conditions) to obtain Example 1. $^1$H NMR (400 MHz, DMSO-d$_6$) δ 11.95 (s, 1H), 8.95 (d, J=7.2 Hz, 1H), 8.39 (s, 1H), 8.25 (br s, 1H), 7.98 (s, 1H), 7.79 (s, 2H), 7.68 (s, 1H), 7.24 (d, J=9.2 Hz, 1H), 7.04 (d, J=6.8 Hz, 1H), 6.80 (s, 1H), 6.69 (s, 1H), 3.83 (s, 2H), 2.89 (s, 4H), 2.69-2.56 (m, 4H), 2.24-2.16 (m, 3H). MS: m/z 456.2 [M+H]$^+$.

Example 2

Example 2

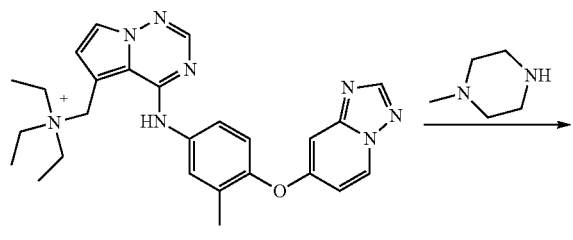

Intermediate 3

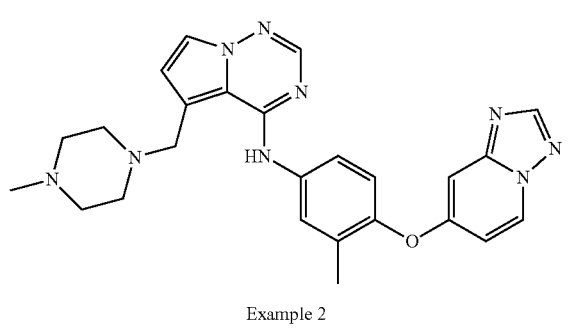

Example 2

Intermediate 3 (0.20 g, 169.64 µmol, 1.00 eq) and methylpiperazine (20 mg, 199.68 µmol, 22 µL, 1.18 eq) were dissolved in acetonitrile (5 mL), and DIPEA (66 mg, 508.93 µmol, 89 µL, 3.00 eq) was added. The reaction mixture was stirred at 70° C. for 1.5 hours. LCMS showed that the reaction was completed. The reaction mixture was concentrated, and separated and purified by preparative HPLC (formic acid condition) to obtain Example 2. $^1$H NMR (400 MHz, MeOH-d$_4$) δ 8.76 (d, J=7.5 Hz, 1H), 8.30 (s, 2H), 7.88 (s, 1H), 7.82 (d, J=2.3 Hz, 1H), 7.68 (dd, J=2.6, 8.7 Hz, 1H), 7.57 (d, J=2.5 Hz, 1H), 7.22 (d, J=8.8 Hz, 1H), 7.10 (dd, J=2.5, 7.5 Hz, 1H), 6.82 (d, J=2.3 Hz, 1H), 6.69 (d, J=2.8 Hz, 1H), 3.96 (s, 2H), 2.91 (s, 8H), 2.57 (s, 3H), 2.27 (s, 3H). MS: m/z 470.1 [M+H].

Example 3

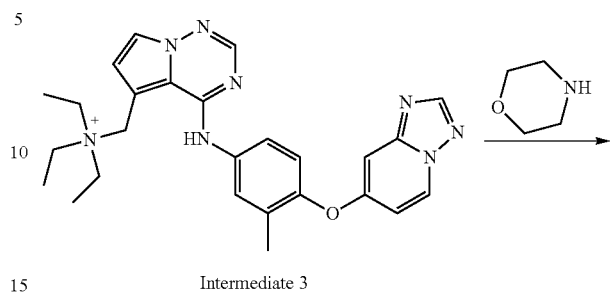

Intermediate 3

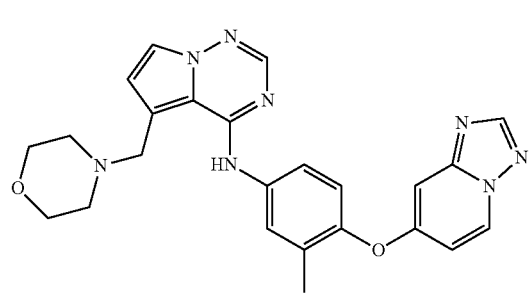

Example 3

Intermediate 3 (300 mg, 636.16 µmol, 1.00 eq), morpholine (28 mg, 318.08 mol, 28 µL, 0.50 eq) and DIPEA (41 mg, 318.08 µmol, 55 µL, 0.50 eq) were added to acetonitrile (2 mL) and stirred at 70° C. for 2 hours. LCMS showed that the reaction was completed. The reaction mixture was cooled to room temperature and filtered. The filtrate was separated by preparative HPLC (formic acid conditions) to obtain Example 3. $^1$H NMR (400 MHz, DMSO-d$_6$) δ 11.91 (s, 1H), 8.93 (d, J=7.6 Hz, 1H), 8.37 (s, 1H), 7.96 (s, 1H), 7.79-7.76 (m, 2H), 7.67 (d, J=2.4 Hz, 1H), 7.23 (d, J=8.4 Hz, 1H), 7.02 (dd, J=2.4, 7.6 Hz, 1H), 6.79 (d, J=2.4 Hz, 1H), 6.67 (d, J=2.4 Hz, 1H), 3.84 (s, 2H), 3.67 (br s, 4H), 2.60 (br s, 4H), 2.19 (s, 3H). MS: m/z 457.1 [M+H]$^+$.

Example 3

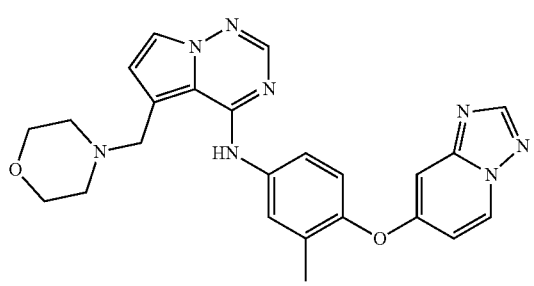 [SMILES: Cc1cc(Nc2ncnn3ccc(CN4CCOCC4)c23)ccc1Oc1ccn2ncnc2c1]

Example 4

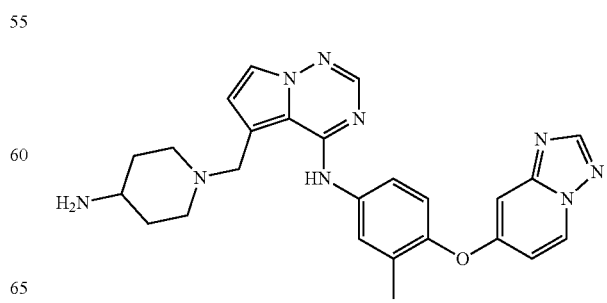

Example 4

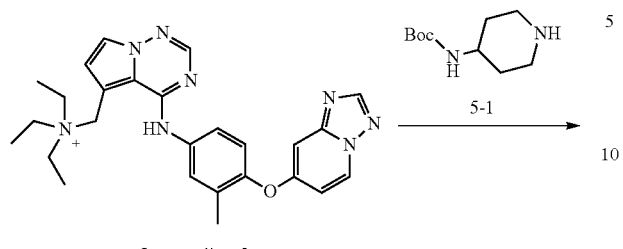

Intermediate 3

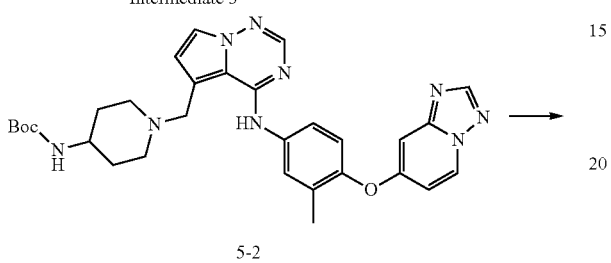

5-2

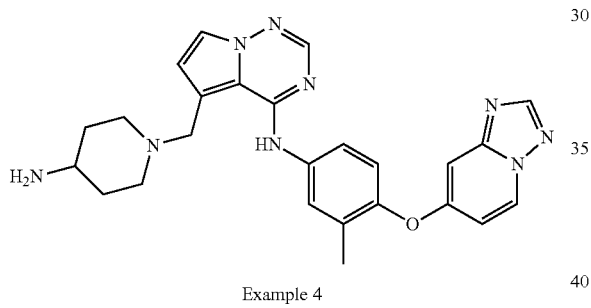

Example 4

Step 1

Intermediate 3 (0.35 g, 148.44 μmol, 1.00 eq) and 5-1 (15 mg, 74.22 μmol, 0.50 eq) were dissolved in acetonitrile (1 mL), and DIPEA (100 mg, 742.2 μmol, 130 μL, 5.00 eq) was added. The reaction mixture was stirred at 70° C. for 1.5 hours. LCMS showed that the reaction was completed. The reaction mixture was concentrated and separated by preparative thin layer chromatography to obtain compound 5-2. MS: m/z 570.2 [M+H]$^+$.

Step 2

Compound 5-2 (18 mg, 31.60 μmol, 1.00 eq) was dissolved in dichloromethane (1 mL), and trifluoroacetic acid (154 mg, 1.35 mmol, 0.1 mL, 42.74 eq) was added. The reaction mixture was stirred at 15° C. for 3 hours. LCMS showed that the reaction was completed. The reaction mixture was concentrated and separated by preparative HPLC (under the condition of formic acid) to obtain Example 4. $^1$H NMR (400 MHz, CDCl$_3$-d) δ 11.41 (s, 1H), 8.40 (d, J=7.6 Hz, 1H), 8.07 (br s, 2H), 7.87 (s, 1H), 7.67 (d, J=1.6 Hz, 1H), 7.42-7.35 (m, 2H), 6.99-6.93 (m, 1H), 6.85-6.77 (m, 2H), 6.42 (d, J=2.4 Hz, 1H), 3.69 (s, 2H), 3.04-3.01 (m, 3H), 2.19-2.04 (m, 5H), 1.99-1.88 (m, 2H), 1.63-1.60 (m, 2H). MS: m/z 470.1 [M+H]$^+$.

Example 5

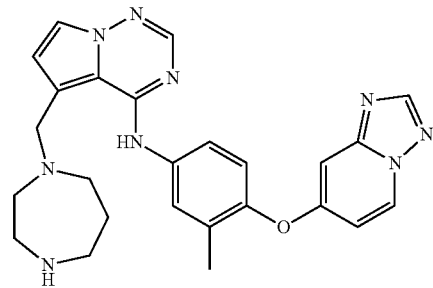 [SMILES: Cc1cc(Nc2ncnn3ccc(CN4CCCNCC4)c23)ccc1Oc1ccn2ncnc2c1]

Example 5

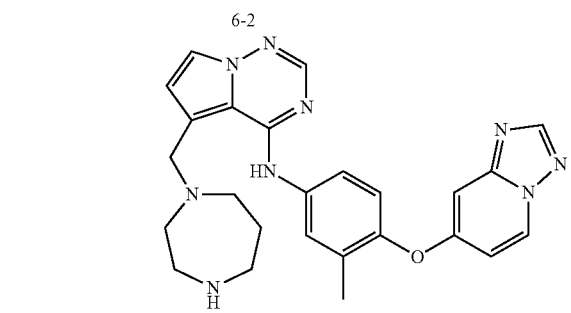

Intermediate 3

6-2

Step 1

Intermediate 3 (0.35 g, 742.19 μmol, 1.00 eq) and 6-1 (75 mg, 371.10 μmol, 73 μL, 0.50 eq) were dissolved in acetonitrile (1 mL), and DIPEA (480 mg, 3711.0 mol, 650 μL, 5.00 eq) was added. The reaction mixture was stirred at 70° C. for 1.5 hours. LCMS showed that the reaction was completed. The reaction mixture was concentrated and separated by preparative thin layer chromatography to obtain compound 6-2. MS: m/z 570.2 [M+H]$^+$.

Step 2

Compound 6-2 (0.03 g, 52.66 μmol, 1.00 eq) was dissolved in dichloromethane (1 mL), and trifluoroacetic acid (60 mg, 526.6 μmol, 39 μL, 10.00 eq) was added. The reaction mixture was stirred at 15° C. for 3 hours. LCMS showed that the reaction was completed. The reaction mixture was concentrated and separated by preparative HPLC (under the condition of formic acid) to obtain Example 5. $^1$H NMR (400 MHz, CDCl$_3$-d) δ 11.24 (s, 1H), 8.42 (d, J=7.6 Hz, 2H), 8.14 (s, 1H), 7.89 (s, 1H), 7.60 (s, 1H), 7.51-7.38 (m, 2H), 7.02 (d, J=8.4 Hz, 1H), 6.87-6.74 (m, 2H), 6.47 (s, 1H), 3.90 (s, 4H), 3.18 (s, 3H), 3.05-2.92 (m, 3H), 2.16 (s, 3H), 2.07-1.96 (m, 2H). MS: m/z 470.2 [M+H]$^+$.

Example 6

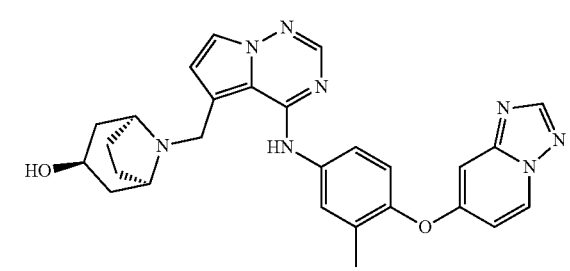 [SMILES: Cc1cc(Nc2ncnn3ccc(CN4[C@@H]5CC[C@H]4C[C@H](O)C5)c23)ccc1Oc1ccn2ncnc2c1]

Example 6

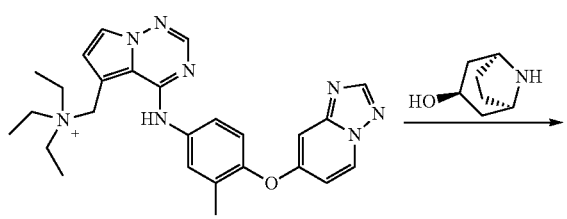

Intermediate 3

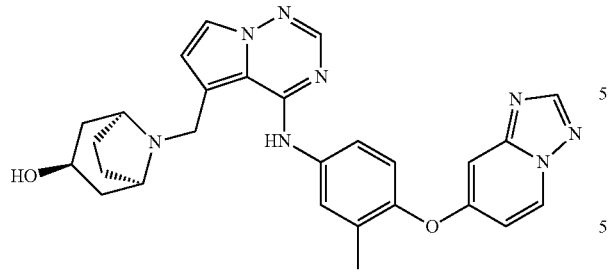

Example 6

The preparation of Example 6 referred to the synthesis method of Example 2. $^1$H NMR (400 MHz, DMSO-d$_6$) δ 12.61 (s, 1H), 8.94 (d, J=7.6 Hz, 1H), 8.39 (s, 1H), 7.93 (s, 1H), 7.69-7.52 (m, 3H), 7.22 (d, J=8.4 Hz, 1H), 7.03 (dd, J=2.4, 7.6 Hz, 1H), 6.79 (d, J=2.4 Hz, 1H), 6.68 (s, 1H), 4.50 (s, 1H), 3.97-3.65 (m, 2H), 3.26 (s, 4H), 2.17 (s, 3H), 1.97 (s, 4H), 1.75 (s, 1H). MS: m/z 497.1 [M+H]$^+$.

Example 7

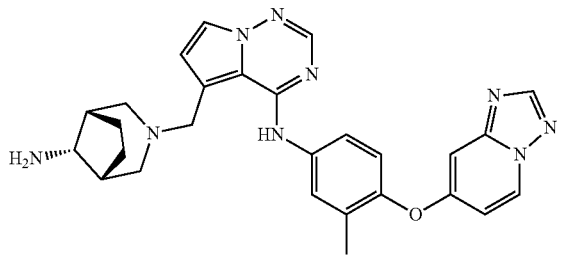 [SMILES: Cc1cc(Nc2ncnn3ccc(CN4C[C@H]5CC[C@@H](C4)[C@H]5N)c23)ccc1Oc1ccn2ncnc2c1]

Example 7

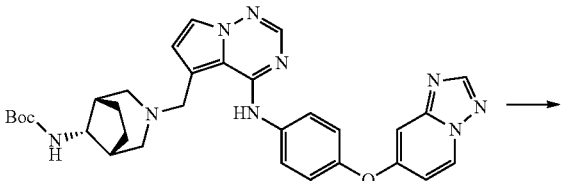

Intermediate 3

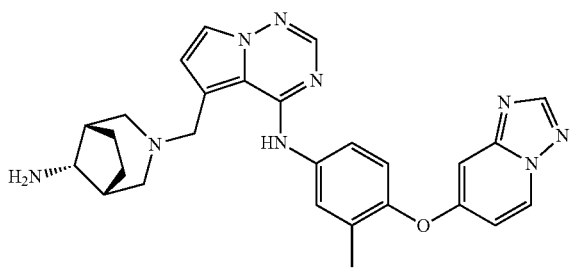

Example 7

The preparation of Example 7 referred to the synthesis method of Example 1. $^1$H NMR (400 MHz, DMSO-d$_6$) δ=10.74 (s, 1H), 8.97 (d, J=7.6 Hz, 1H), 7.92 (s, 1H), 7.86-7.85 (m, 1H), 7.79 (s, 2H), 7.72 (s, 1H), 7.67 (d, J=2.4 Hz, 1H), 7.61 (d, J=7.6 Hz, 1H), 7.27 (d, J=8.4 Hz, 1H), 7.06 (dd, J=2.8, 7.6 Hz, 1H), 6.75 (d, J=2.4 Hz, 1H), 6.64 (d, J=2.4 Hz, 1H), 3.91 (s, 2H), 3.27 (s, 1H), 3.02 (d, J=8.8 Hz, 2H), 2.33 (s, 1H), 2.29 (s, 2H), 2.21 (s, 3H), 1.66 (s, 2H), 1.49 (d, J=8.0 Hz, 2H). MS: m/z 496.1 [M+H]$^+$.

Example 8

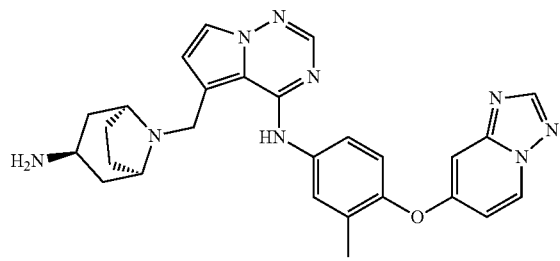 [SMILES: Cc1cc(Nc2ncnn3ccc(CN4[C@@H]5CC[C@H]4C[C@H](N)C5)c23)ccc1Oc1ccn2ncnc2c1]

Example 8

Example 9

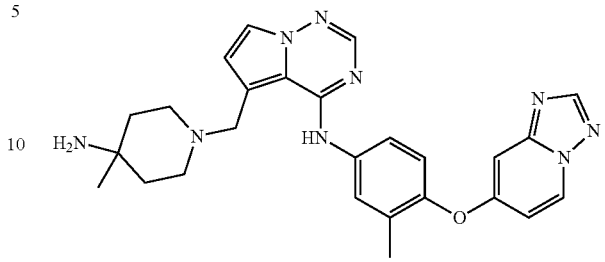

Example 9

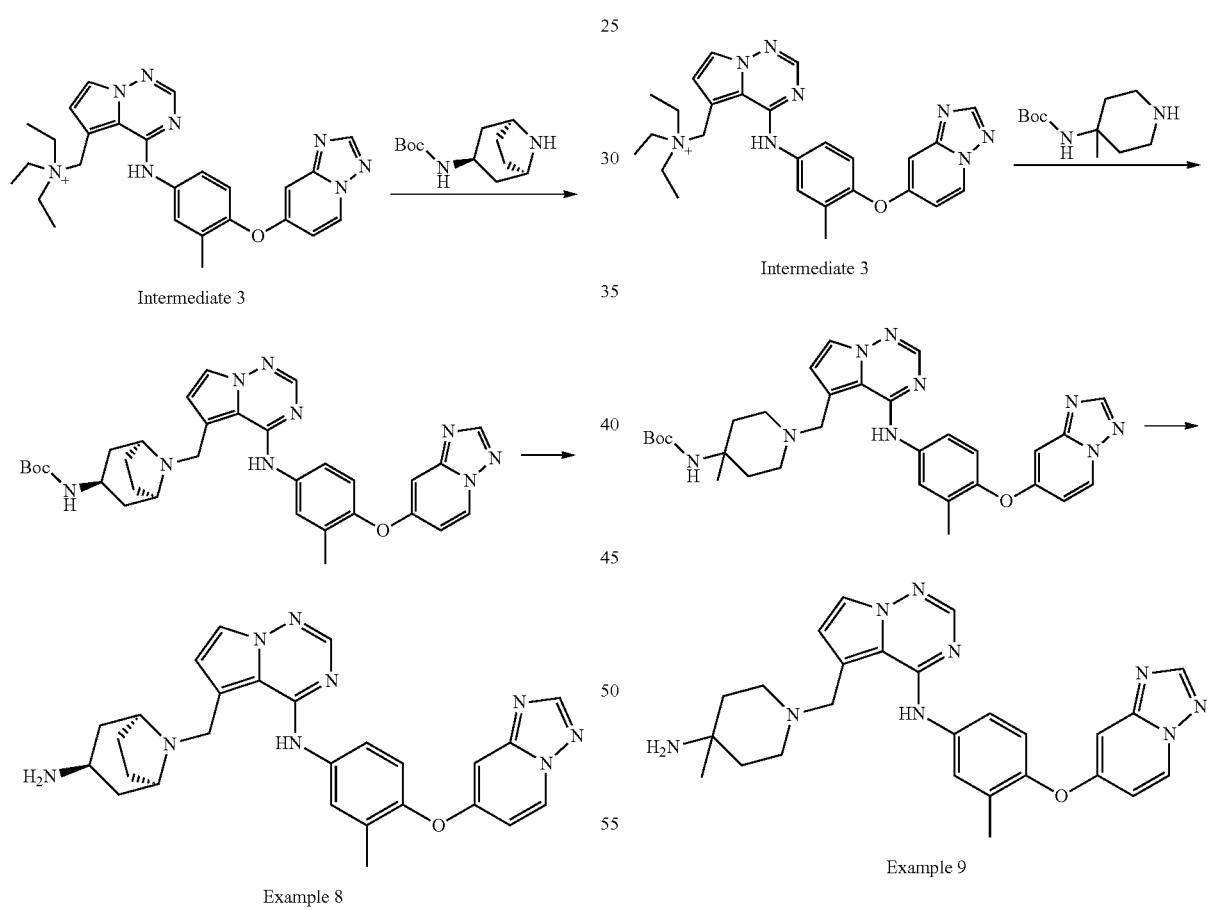

Example 8

Example 9

The preparation of Example 8 referred to the synthesis method of Example 1. $^1$H NMR (400 MHz, DMSO-d$_6$) δ=8.95 (d, J=7.6 Hz, 1H), 8.39 (s, 1H), 7.96 (m, J=14.4 Hz, 4H), 7.68 (m, 3H), 7.22 (d, J=8.4 Hz, 1H), 7.05 (dd, J=2.4, 7.6 Hz, 1H), 6.80 (s, 1H), 6.69 (s, 1H), 4.11 (s, 2H), 3.61-3.45 (m, 1H), 3.48 (m, 3H), 2.19 (s, 3H), 2.09-1.95 (m, 2H), 1.70 (m, J=7.2 Hz, 4H). MS: m/z 496.2 [M+H]$^+$.

The preparation of Example 9 referred to the synthesis method of Example 1. $^1$H NMR (400 MHz, DMSO-d$_6$) δ=11.83 (s, 1H), 8.95 (d, J=7.6 Hz, 1H), 8.39 (s, 1H), 7.98 (s, 1H), 7.82-7.63 (m, 3H), 7.23 (d, J=9.2 Hz, 1H), 7.04 (dd, J=2.8, 7.5 Hz, 1H), 6.79 (d, J=2.4 Hz, 1H), 6.67 (d, J=2.4 Hz, 1H), 3.87 (s, 2H), 2.86 (s, 2H), 2.52-2.51 (m, 2H), 2.20 (s, 3H), 1.86-1.62 (m, 4H), 1.27 (s, 3H). MS: m/z 484.2 [M+H]$^+$.

Example 10

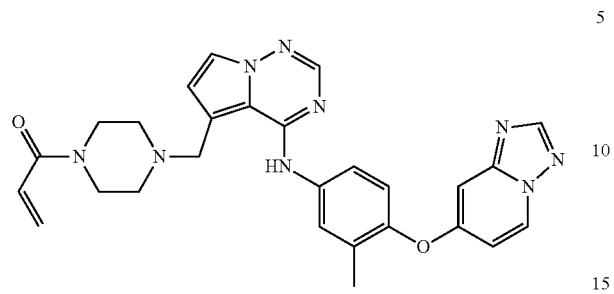

Example 10

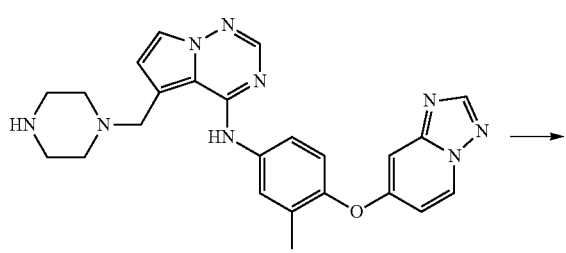

Example 1

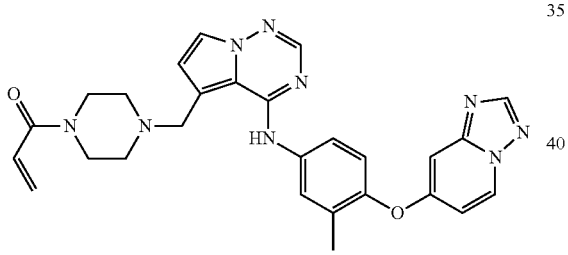

Example 10

Example 1 (0.05 g, 109.77 μmol, 1.00 eq) and sodium bicarbonate (28 mg, 329.30 μmol, 13 μL, 3.00 eq) were dissolved in tetrahydrofuran (0.5 mL) and water (0.5 mL), and a solution of acryloyl chloride (5 mg, 54.88 μmol, 5 μL, 0.50 eq) in tetrahydrofuran (0.5 mL) was added dropwise at 0° C. The reaction mixture was reacted at 0° C. for 1.5 hours. LCMS showed that the reaction was completed. The reaction mixture was diluted with water (50 mL), and then extracted with ethyl acetate (30 mL*3). The organic phases were combined, washed with saturated brine (50 mL), dried over anhydrous sodium sulfate and concentrated to obtain Example 10. $^1$H NMR (400 MHz, DMSO-$d_6$) δ=11.75 (s, 1H), 8.94 (d, J=7.6 Hz, 1H), 8.38 (s, 1H), 8.23 (s, 1H), 7.99 (s, 1H), 7.79 (s, 1H), 7.76 (d, J=8.8 Hz, 1H), 7.69 (d, J=2.4 Hz, 1H), 7.23 (d, J=8.4 Hz, 1H), 7.03 (dd, J=2.4, 7.5 Hz, 1H), 6.86-6.74 (m, 2H), 6.68 (d, J=2.0 Hz, 1H), 6.12 (dd, J=2.0, 16.8 Hz, 1H), 5.69 (dd, J=2.0, 10.4 Hz, 1H), 3.88 (s, 2H), 3.79-3.63 (m, 4H), 2.75-2.54 (m, 4H), 2.20 (s, 3H). MS: m/z 510.1 [M+H]$^+$.

Example 11

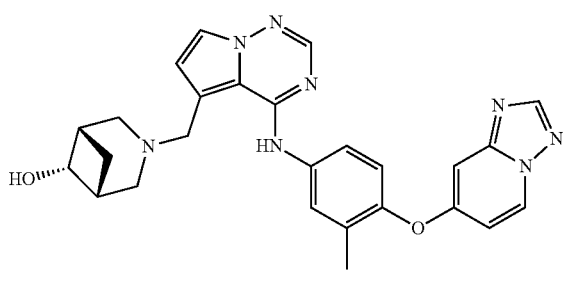 [SMILES: Cc1cc(Nc2ncnn3ccc(CN4C[C@H]5C[C@@H](C4)[C@H]5O)c23)ccc1Oc1ccn2ncnc2c1]

Example 11

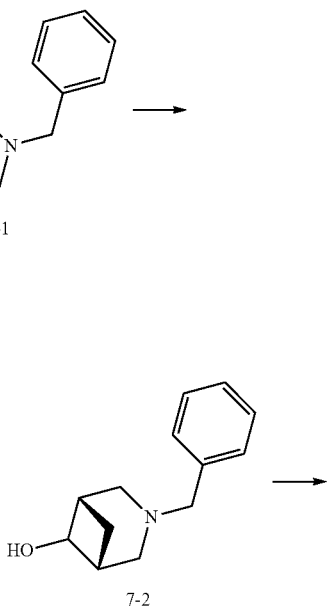

7-1

7-2

7-3

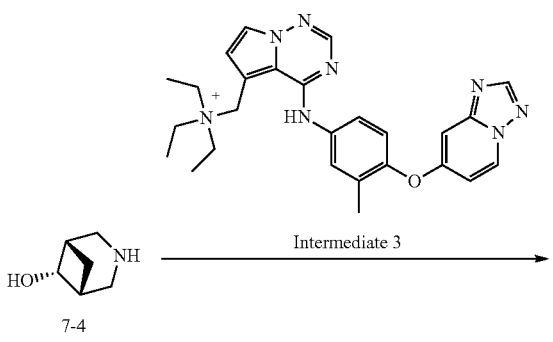

7-4 → Intermediate 3

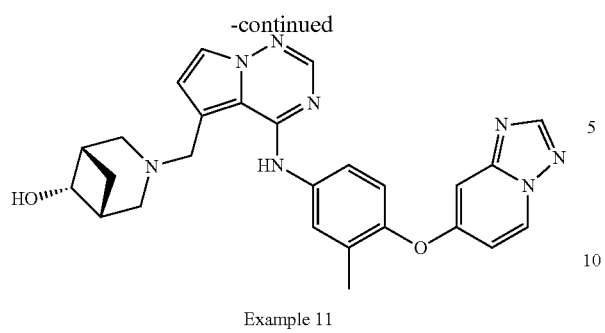

Example 11

Step 1

Compound 7-1 (0.24 g, 1.19 mmol, 1.00 eq) was dissolved in methanol (2 mL). The reaction mixture was cooled to −60° C., and sodium borohydride (50 mg, 1.31 mmol, 1.10 eq) was added. The reaction mixture was heated to 15° C. and stirred for 3 hours. TLC detected that the reaction was completed. The reaction mixture was concentrated, diluted with water (50 mL) and extracted with ethyl acetate (50 mL*3). The organic phases were combined, washed with saturated brine (50 mL), dried over anhydrous sodium sulfate and concentrated to obtain compound 7-2.

Step 2

Compound 7-2 (0.30 g, 1.48 mmol, 1.00 eq) was dissolved in ethyl acetate (5 mL), and palladium hydroxide on carbon (0.30 g, 20% purity) and di-tert-butyl dicarbonate (419 mg, 1.92 mmol, 441 μL, 1.30 eq) were added. The reaction mixture was stirred at 15° C. for 16 hours under hydrogen atmosphere (15 psi). TLC detected that the reaction was completed. The reaction mixture was filtered (diatomite filter aid), and the filtrate was concentrated to obtain compound 7-3. $^1$H NMR (400 MHz, CHCl$_3$-d) δ=4.03 (q, J=6.0 Hz, 1H), 3.61-3.41 (m, 4H), 2.58-2.35 (m, 2H), 1.90 (d, J=7.2 Hz, 1H), 1.54 (d, J=6.4 Hz, 1H), 1.41 (s, 9H), 1.31-1.24 (m, 1H).

Step 3

Compound 7-3 (0.10 g, 468.88 μmol, 1.00 eq) was dissolved in ethyl acetate hydrochloride (5 mL) and stirred at 15° C. for 16 hours. TLC detected that the reaction was completed. The reaction mixture was concentrated to obtain compound 7-4.

Step 4

Intermediate 3 (0.15 g, 318.08 μmol, 1.00 eq) was dissolved in acetonitrile (5 mL), and compound 7-4 (54 mg, 477.12 μmol, 1.50 eq) and DIPEA (206 mg, 1.59 mmol, 278 μL, 5.00 eq) were added. The reaction mixture was stirred at 70° C. for 0.5 hour. LCMS detected that the reaction was completed. The reaction mixture was concentrated, and separated and purified by preparative HPLC (under the condition of formic acid) to obtain Example 11. $^1$H NMR (400 MHz, DMSO-d$_6$) δ=12.28-12.08 (m, 1H), 8.94 (d, J=7.6 Hz, 1H), 8.38 (s, 1H), 7.98 (s, 1H), 7.89 (d, J=2.4 Hz, 1H), 7.82-7.76 (m, 1H), 7.66 (d, J=2.4 Hz, 1H), 7.22 (d, J=8.4 Hz, 1H), 7.02 (dd, J=2.8, 7.6 Hz, 1H), 6.81-6.69 (m, 2H), 5.30 (s, 1H), 3.94-3.87 (m, 3H), 3.07 (d, J=9.2 Hz, 2H), 2.85 (d, J=10.4 Hz, 2H), 2.36-2.33 (m, 1H), 2.36-2.33 (m, 1H), 2.18 (s, 3H), 1.57 (d, J=9.6 Hz, 1H), 1.35-1.27 (m, 1H). MS: m/z 483.1 [M+H]$^+$.

Example 12

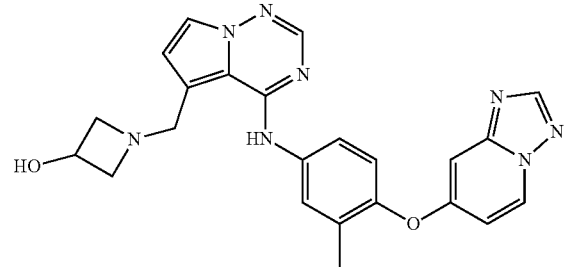 [SMILES: Cc1cc(Nc2ncnn3ccc(CN4CC(O)C4)c23)ccc1Oc1ccn2ncnc2c1]

Example 12

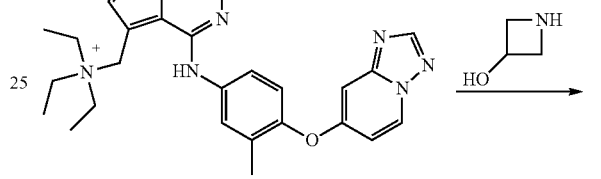

Intermediate 3

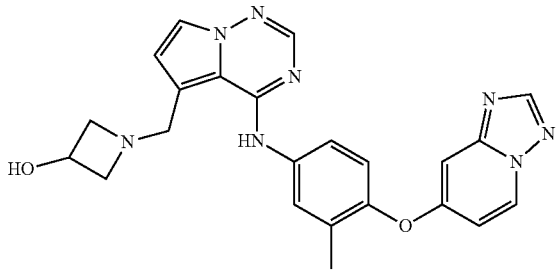

Example 12

The preparation of Example 12 referred to the synthesis method of Example 2. $^1$H NMR (400 MHz, MeOH-d$_4$) δ=8.76 (d, J=7.6 Hz, 1H), 8.31 (s, 1H), 7.84-7.74 (m, 2H), 7.64 (d, J=8.8 Hz, 1H), 7.50 (d, J=2.4 Hz, 1H), 7.20 (d, J=8.8 Hz, 1H), 7.10 (dd, J=2.4, 7.6 Hz, 1H), 6.82 (d, J=2.4 Hz, 1H), 6.66 (d, J=2.4 Hz, 1H), 4.94-4.91 (m, 2H), 4.57 (quin, J=5.6 Hz, 1H), 4.15 (s, 2H), 3.98-3.78 (m, 2H), 2.26 (s, 3H). MS: m/z 443.0 [M+H]$^+$.

Example 13

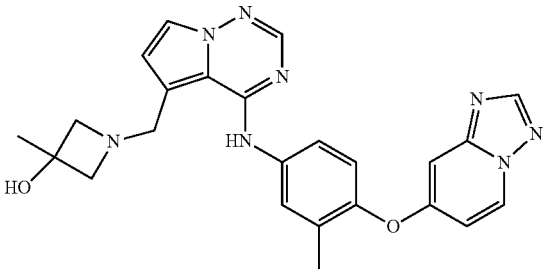 [SMILES: Cc1cc(Nc2ncnn3ccc(CN4CC(C)(O)C4)c23)ccc1Oc1ccn2ncnc2c1]

Example 13

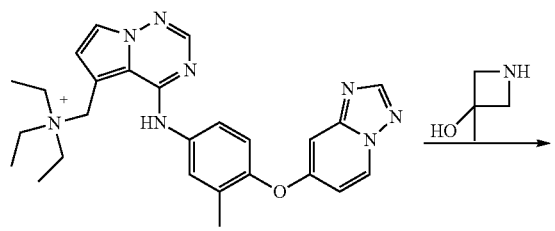

Intermediate 3

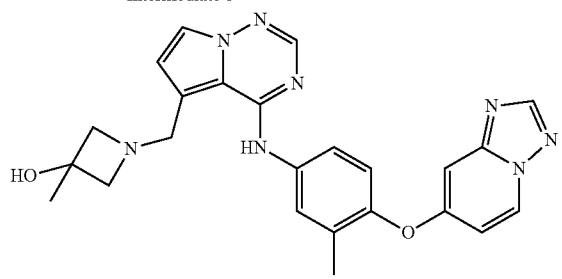

Example 13

The preparation of Example 13 referred to the synthesis method of Example 2. $^1$H NMR (400 MHz, MeOH-d$_4$) δ=8.76 (d, J=7.6 Hz, 1H), 8.30 (s, 1H), 7.93 (s, 1H), 7.90-7.80 (m, 2H), 7.51 (d, J=2.8 Hz, 1H), 7.18 (d, J=8.4 Hz, 1H), 7.09 (dd, J=2.4, 7.6 Hz, 1H), 6.81 (d, J=2.4 Hz, 1H), 6.65 (d, J=2.4 Hz, 1H), 4.92-4.91 (m, 2H), 4.03-3.97 (m, 2H), 3.43 (d, J=7.2 Hz, 2H), 2.26 (s, 3H), 1.48 (s, 3H). MS: m/z 457.1 [M+H]$^+$.

Example 14

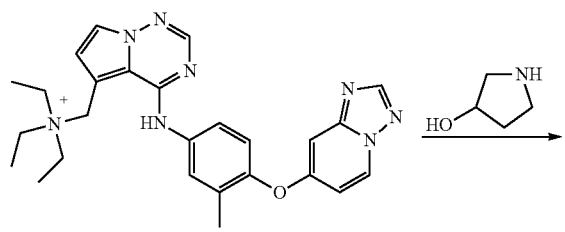

Intermediate 3

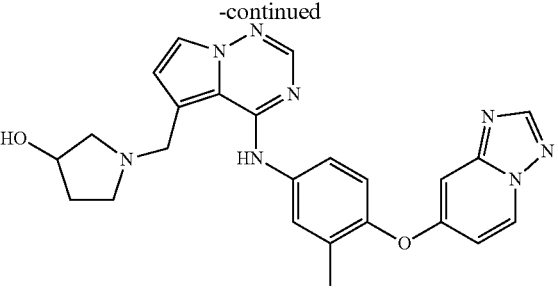

Example 14

The preparation of Example 14 referred to the synthesis method of Example 2. $^1$H NMR (400 MHz, DMSO-d$_6$) δ=12.80 (s, 1H), 8.93 (d, J=7.2 Hz, 1H), 8.38 (s, 1H), 8.00-7.82 (m, 3H), 7.65 (d, J=2.4 Hz, 1H), 7.18 (d, J=8.4 Hz, 1H), 7.02 (dd, J=2.4, 7.6 Hz, 1H), 6.78 (d, J=2.4 Hz, 1H), 6.65 (d, J=2.4 Hz, 1H), 4.38 (s, 1H), 3.95-3.84 (m, 2H), 2.97 (d, J=6.4 Hz, 1H), 2.82-2.63 (m, 2H), 2.26-2.11 (m, 4H), 1.84-1.64 (m, 1H). MS: m/z 457.1 [M+H]$^+$.

Example 15

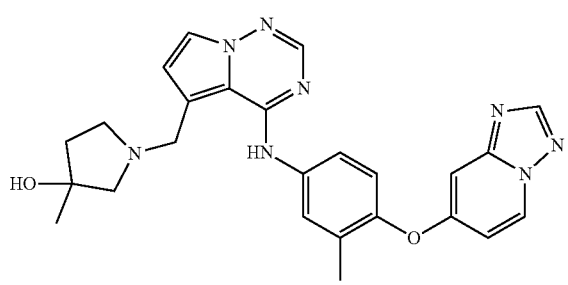 [SMILES: Cc1cc(Nc2ncnn3ccc(CN4CCC(C)(O)C4)c23)ccc1Oc1ccn2ncnc2c1]

Example 15

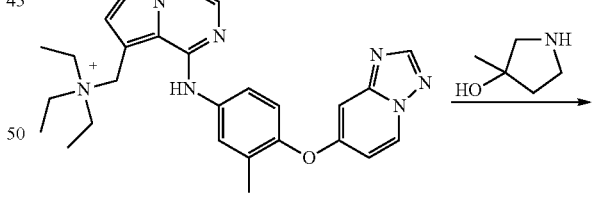

Intermediate 3

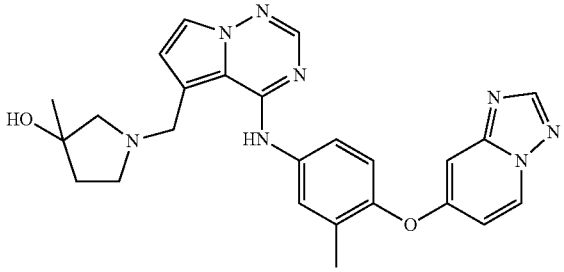

Example 15

The preparation of Example 15 referred to the synthesis method of Example 2. ¹H NMR (400 MHz, DMSO-d₆) δ=8.94 (d, J=7.6 Hz, 1H), 8.39 (s, 1H), 7.94 (s, 1H), 7.66 (d, J=2.4 Hz, 3H), 7.24 (d, J=8.4 Hz, 1H), 7.04 (dd, J=2.4, 7.6 Hz, 1H), 6.79 (d, J=2.4 Hz, 1H), 6.67 (d, J=2.4 Hz, 1H), 4.35 (s, 1H), 3.84 (s, 2H), 2.18 (s, 3H), 1.58 (s, 4H), 1.12 (s, 3H). MS: m/z 485.1 [M+H]⁺.

Example 16

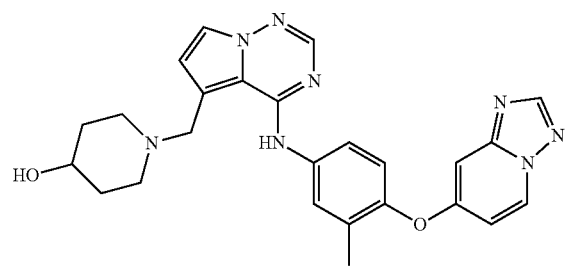 [SMILES: Cc1cc(Nc2ncnn3ccc(CN4CCC(O)CC4)c23)ccc1Oc1ccn2ncnc2c1]

Example 16

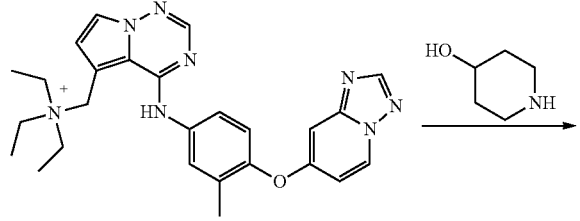

Intermediate 3

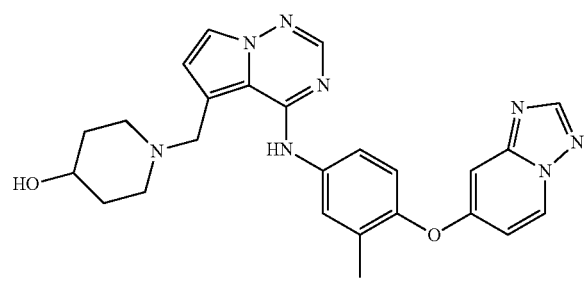

Example 16

The preparation of Example 16 referred to the synthesis method of Example 2. ¹H NMR (400 MHz, DMSO-d₆) δ=8.95 (d, J=7.6 Hz, 1H), 8.39 (s, 1H), 8.14 (s, 1H), 7.93 (s, 1H), 7.66 (s, 3H), 7.24 (d, J=8.4 Hz, 1H), 7.04 (dd, J=2.4, 7.6 Hz, 1H), 6.82 (s, 1H), 6.67 (s, 1H), 4.80 (s, 1H), 3.91 (s, 1H), 3.75-3.49 (m, 1H), 3.64 (d, J=11.6 Hz, 1H), 3.13-2.86 (m, 2H), 2.19 (s, 3H), 1.94-1.73 (m, 2H), 1.52 (s, 2H). MS: m/z 471.1 [M+H]⁺.

Example 17

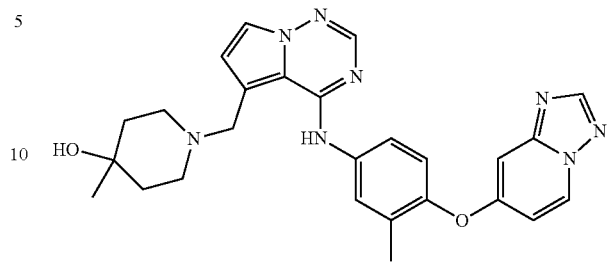

Example 17

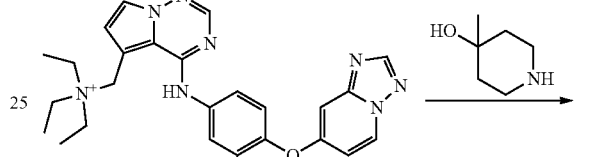

Intermediate 3

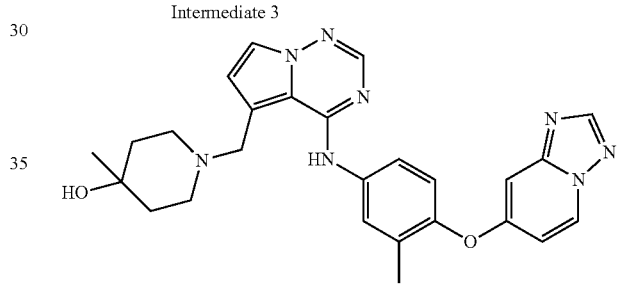

Example 17

The preparation of Example 17 referred to the synthesis method of Example 2. ¹H NMR (400 MHz, DMSO-d₆) δ=8.94 (d, J=7.6 Hz, 1H), 8.38 (s, 1H), 8.04-7.80 (m, 3H), 7.64 (d, J=2.4 Hz, 1H), 7.18 (d, J=8.8 Hz, 1H), 7.02 (dd, J=2.4, 7.6 Hz, 1H), 6.77 (d, J=2.4 Hz, 1H), 6.65 (d, J=2.4 Hz, 1H), 4.82 (s, 1H), 3.91 (s, 2H), 3.08 (s, 1H), 2.86 (s, 1H), 2.17 (s, 3H), 2.02-1.76 (m, 2H), 1.29 (s, 3H). MS: m/z 471.2 [M+H]⁺.

Example 18

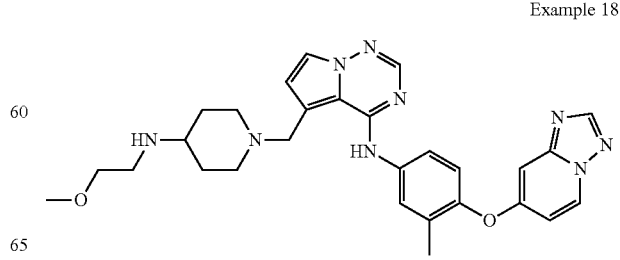

Example 18

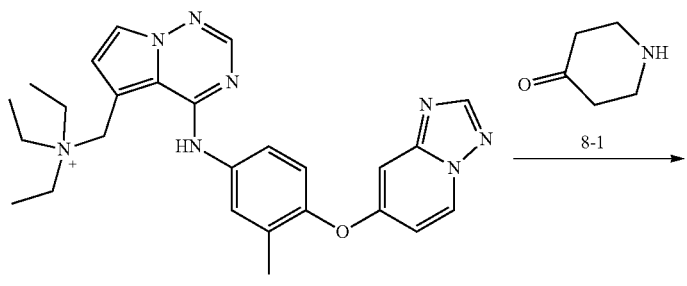

Intermediate 3

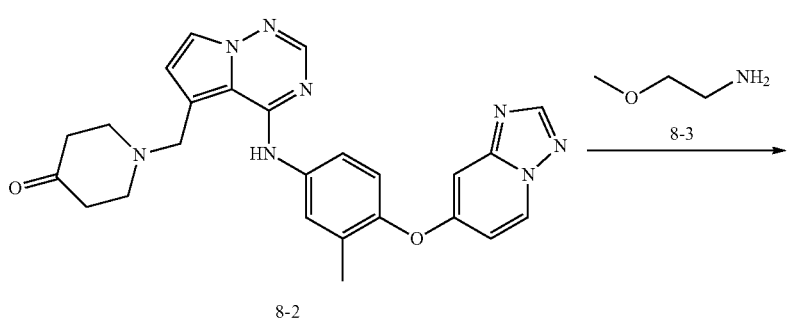

8-2

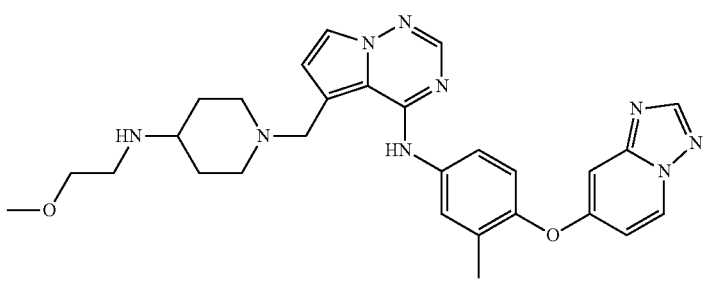

Example 18

Step 1

Intermediate 3 (1.00 g, 2.12 mmol, 1.00 eq) and compound 8-1 were dissolved in acetonitrile (10 mL), and DIPEA (1.37 g, 10.60 mmol, 1.85 mL, 5.00 eq) was added. The reaction mixture was stirred at 70° C. for 2 hours. After LCMS detected that the reaction was completed, the reaction mixture was concentrated, poured into water (50 mL), and then extracted with ethyl acetate (50 mL*3). The organic phases were combined, washed with saturated brine (50 mL), dried over anhydrous sodium sulfate and concentrated to obtain compound 8-2. MS: m/z 487.4 [M+H$_2$O+H]$^+$.

Step 2

Compound 8-2 (0.15 g, 263.77 μmol, 1.00 eq) and compound 8-3 (160.32 mg, 2.13 mmol, 185.55 μL, 10.00 eq) were dissolved in ethanol (5 mL) and stirred at 25° C. for 0.5 hour, and sodium borohydride (80.75 mg, 2.13 mmol, 10.00 eq) was added. The reaction mixture was continuously stirred at 25° C. for 16 hours. LCMS detected that the reaction was completed. The reaction mixture was quenched with water (50 mL) and then extracted with ethyl acetate (50 mL*3). The organic phases were combined, washed with saturated brine (50 mL), dried over anhydrous sodium sulfate and concentrated to obtain a crude product. The crude product was separated and purified by preparative HPLC (under the condition of formic acid) to obtain Example 18. $^1$H NMR (400 MHz, DMSO-d$_6$) δ 12.06 (s, 1H), 8.93 (d, J=7.6 Hz, 1H), 8.38 (s, 1H), 8.27 (s, 1H), 7.96 (s, 1H), 7.80-7.72 (m, 2H), 7.66 (d, J=2.4 Hz, 1H), 7.22 (d, J=9.2 Hz, 1H), 7.02 (dd, J=2.8, 7.6 Hz, 1H), 6.80 (d, J=2.4 Hz, 1H), 6.65 (d, J=2.8 Hz, 1H), 3.80 (s, 1H), 3.42 (t, J=5.6 Hz, 3H), 3.23 (s, 3H), 3.06 (d, J=9.6 Hz, 2H), 2.81-2.72 (m, 3H), 2.24-2.08 (m, 5H), 1.93 (d, J=11.6 Hz, 2H), 1.56-1.38 (m, 2H). MS: m/z 528.4 [M+H]$^+$.

Example 19

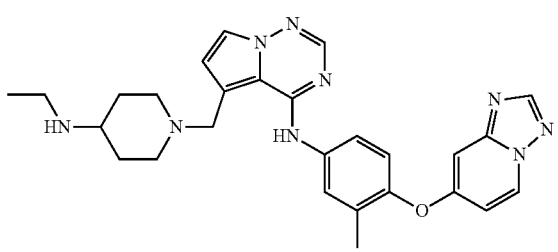

Example 19

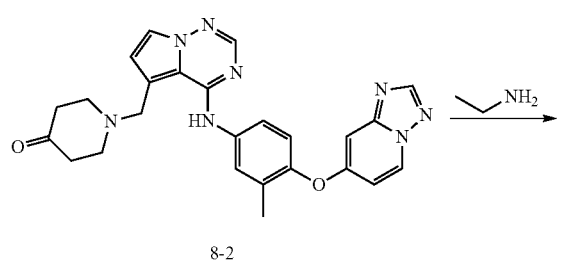

8-2

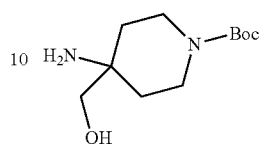

Example 20

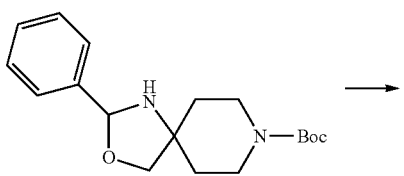

9-1

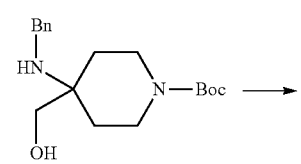

9-2

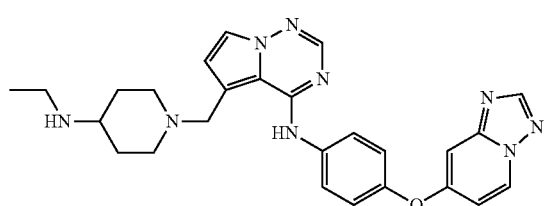

Example 19

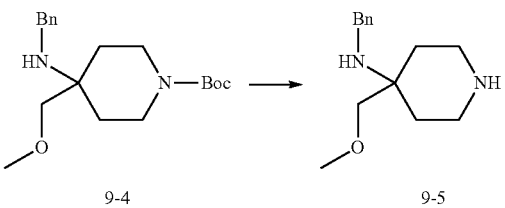

9-3

Compound 8-2 (70 mg, 149 μmol, 1 eq) and an ethylamine aqueous solution (10.1 mg, 224 μmol, 14.7 μL, 1.5 eq) were dissolved in 1,2-dichloroethane (10 mL), and then sodium acetate borohydride (63.3 mg, 298 μmol, 2 eq) and acetic acid (17.9 mg, 298 μmol, 17.1 μL, 2 eq) were added. The reaction mixture was reacted at 20° C. for 2 hours. After the reaction was completed, the reaction mixture was added with water (5 ml), and then concentrated under reduced pressure to obtain a crude product. The crude product was purified by preparative HPLC (neutral condition) to obtain Example 19. $^1$H NMR (400 MHz, DMSO-$d_6$) δ 8.94 (d, J=7.6 Hz, 1H), 8.39 (s, 1H), 7.96 (s, 1H), 7.78-7.73 (m, 2H), 7.67 (d, J=2.4 Hz, 1H), 7.24 (d, J=8.4 Hz, 1H), 7.03 (dd, J=2.4, 7.6 Hz, 1H), 6.81 (d, J=2.4 Hz, 1H), 6.66 (d, J=2.4 Hz, 1H), 3.80 (s, 2H), 3.65 (t, J=6.8 Hz, 1H), 3.02 (br s, 2H), 2.20 (s, 3H), 1.86 (br d, J=12.0 Hz, 2H), 1.76 (td, J=6.8, 14.4 Hz, 1H), 1.64-1.56 (m, 1H), 1.55-1.41 (m, 2H), 1.36 (br s, 2H), 0.98 (t, J=7.2 Hz, 3H). MS: m/z 498.2 [M+H]$^+$.

Example 20

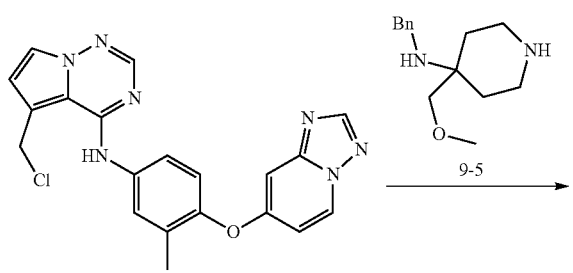

Intermediate 4

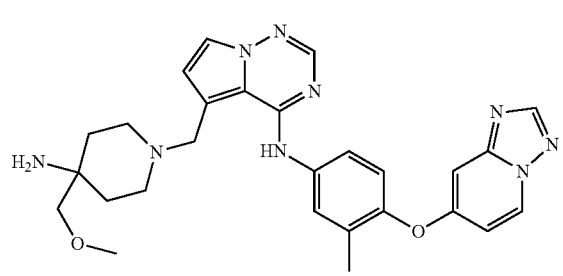 [SMILES: COCC1(N)CCN(Cc2ccn3ncnc(Nc4ccc(Oc5ccn6ncnc6c5)c(C)c4)c23)CC1]

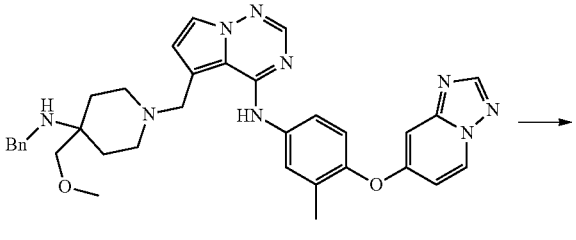

9-6

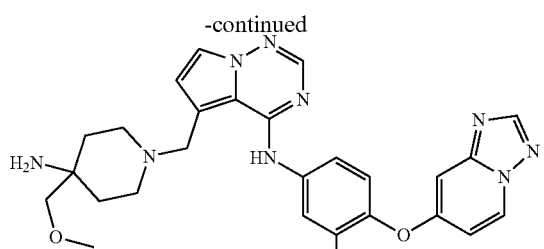

Example 20

Step 1

Compound 9-1 (50 mg, 217.10 μmol, 1.00 eq) was dissolved in anhydrous tetrahydrofuran (1 mL), and benzaldehyde (28 mg, 260.53 μmol, 26 μL, 1.20 eq) and anhydrous magnesium sulfate (78 mg, 651.31 μmol, 3.00 eq) were added. The reaction mixture was stirred at 25° C. for 16 hours under nitrogen protection. The reaction mixture was directly filtered, and the filtrate was concentrated under reduced pressure to obtain a crude product of compound 9-2.

Step 2

Compound 9-2 (50 mg, 157.03 μmol, 1.00 eq) was dissolved in anhydrous methanol (5 mL), and sodium borohydride (18 mg, 471.09 μmol, 3.00 eq) was added. The reaction mixture was stirred at 25° C. for 16 hours. TLC detected that the reaction was completed. The same reaction mixture was thrown into two pots, combined and processed. The reaction mixture was diluted with water (20 mL), and extracted with ethyl acetate (20 mL*2). The organic phase was washed with saturated brine (20 mL), dried over anhydrous sodium sulfate and filtered. The filtrate was concentrated under reduced pressure to obtain a crude product. The crude product was separated by column chromatography (ISCO®; 4 g SepaFlash® fast silica gel column, mobile phase: 0 to 10% MeOH/DCM, flow rate: 18 mL/min) to obtain compound 9-3. $^1$H NMR (400 MHz, CDCl$_3$-d) δ 7.35-7.27 (m, 5H), 3.67 (s, 2H), 3.59-3.56 (m, 2H), 3.48 (s, 2H), 3.39-3.33 (m, 2H), 1.67-1.61 (m, 2H), 1.59-1.54 (m, 2H), 1.46 (s, 8H).

Step 3

Compound 9-3 (120 mg, 374.50 μmol, 1.00 eq) was dissolved in anhydrous tetrahydrofuran (5 mL), and sodium hydrogen (45 mg, 1.12 mmol, 60% purity, 3.00 eq) was added in batches at 0° C. The reaction mixture was stirred at 0° C. for 0.5 hour, and then methyl iodide (64 mg, 449.40 μmol, 28 μL, 1.20 eq) was added at 0° C. The reaction mixture was stirred at 25° C. for 16 hours under nitrogen protection. TLC detected that the reaction was completed. The reaction mixture was quenched with a saturated aqueous ammonium chloride solution (1 mL) at 0° C., diluted with water (20 mL), and extracted with ethyl acetate (20 mL*2). The organic phase was washed with saturated brine organic phase (20 mL*2), dried with anhydrous sodium sulfate and filtered. The filtrate was concentrated under reduced pressure to obtain compound 9-4. $^1$H NMR (400 MHz, CDCl$_3$-d) δ 7.29-7.40 (m, 4H), 7.21-7.25 (m, 1H), 3.66 (s, 4H), 3.39-3.36 (m, 5H), 3.30 (br s, 2H), 1.67-1.61 (m, 2H), 1.46 (s, 9H), 1.26 (br s, 2H).

Step 4

Compound 9-4 (140 mg, 418.60 μmol, 1.00 eq) was dissolved in dichloromethane (5 mL), and trifluoroacetic acid (770.00 mg, 6.75 mmol, 0.5 mL, 16.13 eq) was added. The reaction mixture was stirred at 25° C. for 16 hours. TLC detected that the reaction was completed. The reaction mixture was directly concentrated under reduced pressure to obtain a crude product of compound 9-5.

Step 5

Intermediate 4 (140 mg, 316.53 μmol, 1.00 eq, HCl) and compound 9-5 (223 mg, 949.58 μmol, 3.00 eq) were added to acetonitrile (5 mL), and then N,N-diisopropylethylamine (205 mg, 1.58 mmol, 276 μL, 5.00 eq) was added at 0° C. The reaction mixture was stirred at 25° C. for 1 hour. LCMS showed that the reaction was completed. The reaction mixture was directly concentrated under reduced pressure to obtain a crude product. The crude product was separated by column chromatography separated (ISCO®; 4 g SepaFlash® fast silica gel column, mobile phase: 0 to 10% MeOH/DCM, flow rate: 18 mL/min) to obtain compound 9-6. MS: m/z 604.1 [M+H]$^+$.

Step 6

Compound 9-6 (50 mg, 82.82 μmol, 1.00 eq) was dissolved in methanol (10 mL), and wet palladium hydroxide/carbon (50 mg, 20% purity) was added under nitrogen protection. The reaction mixture was reacted at 25° C. for 16 hours under hydrogen pressure of 15 psi. LCMS showed that the reaction was completed. The reaction mixture was filtered through diatomite. The filter cake was rinsed with methanol, and the filtrate was concentrated under reduced pressure to obtain a crude product. The crude product was separated by preparative HPLC (under the condition of formic acid) to obtain Example 20. $^1$H NMR (400 MHz, DMSO-d$_6$) δ 11.91 (br s, 1H), 8.94 (d, J=7.2 Hz, 1H), 8.38 (s, 1H), 7.97 (m, 1H), 7.77-7.68 (m, 2H), 7.69-7.67 (m, 1H), 7.23 (d, J=8.4 Hz, 1H), 7.04 (dd, J=2.4, 7.6 Hz, 1H), 6.78 (d, J=2.4 Hz, 1H), 6.67 (d, J=2.4 Hz, 1H), 3.86 (s, 2H), 3.51-3.50 (m, 3H), 3.32 (s, 2H), 2.77 (br s, 2H), 2.57-2.52 (m, 2H), 2.20 (s, 3H), 1.82-1.76 (m, 2H), 1.76-1.69 (m, 2H). MS: m/z 514.1 [M+Na]$^+$.

Examples 21 and 22

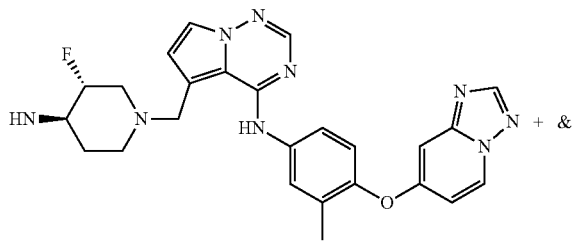

Example 21 or Example 22

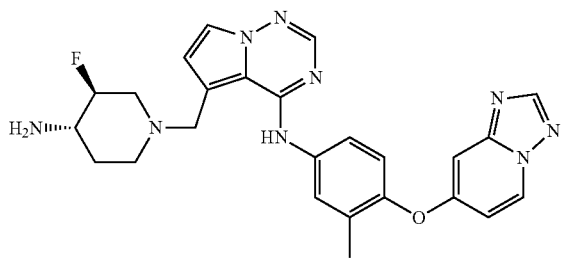

Example 22 or Example 21

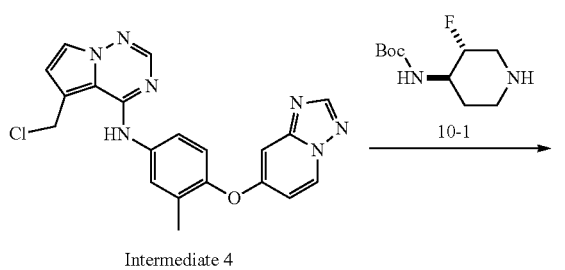

Intermediate 4

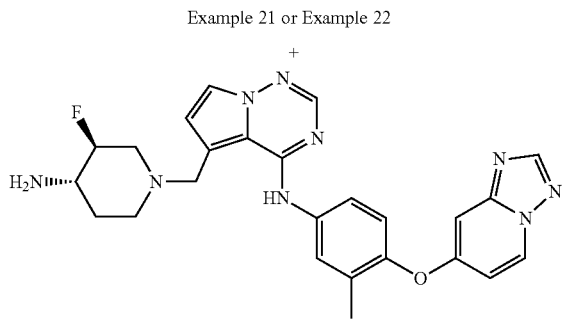

Example 21 or Example 22

+

Example 22 or Example 21

Step 1

Intermediate 4 (250 mg, 565.23 μmol, 1.00 eq, HCl) and compound 10-1 (123 mg, 565.23 μmol, 1.00 eq) were added to acetonitrile (5 mL), and then N,N-diisopropylethylamine (219 mg, 1.70 mmol, 295 μL, 3.00 eq) was added at 0° C. The reaction mixture was stirred at 25° C. for 1 hour. LCMS showed that the reaction was completed. The reaction mixture was directly concentrated under reduced pressure to obtain a crude product. The crude product was separated by column chromatography (ISCO®; 4 g SepaFlash® fast silica gel column, mobile phase: 0 to 10% MeOH/DCM, flow rate: 18 mL/min) to separated obtain compound 10-2. MS: m/z 610.1 [M+Na]$^+$.

Step 2

Compound 10-2 (220.00 mg, 374.37 μmol, 1 eq) was dissolved in dichloromethane (10 mL), and trifluoroacetic acid (1.54 g, 13.51 mmol, 1 mL, 36.08 eq) was added. The reaction mixture was stirred at 25° C. for 1 hour. LCMS showed that the reaction was completed. The reaction mixture was concentrated to remove dichloromethane, diluted with saturated sodium bicarbonate aqueous solution (20 mL), and then extracted with ethyl acetate (20 mL*2). The organic phase was washed with saturated brine (20 mL), dried over anhydrous sodium sulfate and filtered. The filtrate was concentrated to obtain a crude product (130 mg). The crude product was chirally separated by SFC to obtain Example 21 (SFC: $t_R$=1.379 min, SFC detection conditions: chromatographic column: Chiralpak AD-3 50×4.6 mm 3 m; mobile phase: A phase: carbon dioxide, B phase: ethanol (containing 0.05% ethanolamine); gradient: keeping 40%; flow rate: 4 ml per minute; column temperature: 35° C.) and Example 22 (SFC: $t_R$=2.614 min, the detection conditions were the same as in Example 21). Example 21: $^1$H NMR (400 MHz, DMSO-$d_6$) δ 11.59 (s, 1H), 8.94 (d, J=7.6 Hz, 1H), 8.39 (s, 1H), 7.98 (s, 1H), 7.76-7.72 (m, 2H), 7.69 (d, J=2.4 Hz, 1H), 7.23 (d, J=9.6 Hz, 1H), 7.03 (dd, J=2.4, 7.6 Hz, 1H), 6.81 (d, J=2.4 Hz, 1H), 6.68 (d, J=2.4 Hz, 1H), 4.41-4.26 (m, 1H), 3.88 (s, 2H), 3.13 (br s, 1H), 2.91 (br s, 2H), 2.35 (br s, 2H), 2.19 (s, 3H), 1.92 (br s, 1H), 1.45-1.43 (m, 1H). MS: m/z 488.1 [M+H]$^+$. Example 22: $^1$H NMR (400 MHz, DMSO-$d_6$) δ 11.60 (s, 1H), 8.94 (d, J=7.6 Hz, 1H), 8.39 (s, 1H), 7.98 (s, 1H), 7.80-7.71 (m, 2H), 7.69 (d, J=2.8 Hz, 1H), 7.23 (d, J=9.2 Hz, 1H), 7.03 (dd, J=2.8, 7.6 Hz, 1H), 6.81 (d, J=2.4 Hz, 1H), 6.68 (d, J=2.4 Hz, 1H), 4.43-4.23 (m, 1H), 3.87 (s, 2H), 3.13 (br s, 1H), 2.89 (br s, 2H), 2.36 (br s, 1H), 2.45-2.30 (m, 1H), 2.19 (s, 3H), 1.98-1.86 (m, 1H), 1.45-1.42 (m, 1H). MS: m/z 488.2 [M+H]$^+$.

Examples 23 and 24

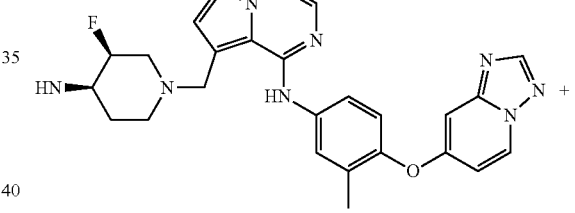

Example 23 or Example 24

+

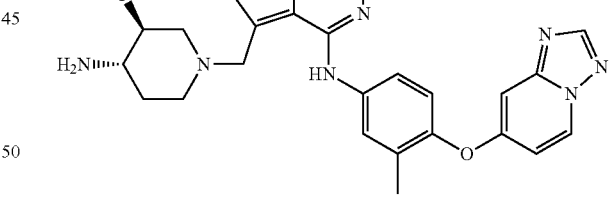

Example 24 or Example 23

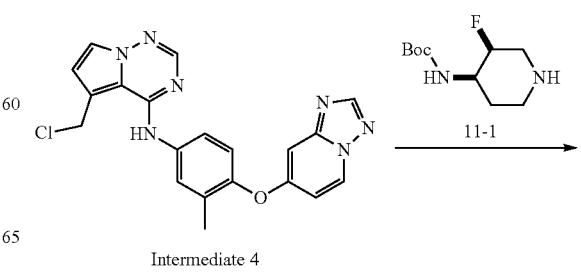

Intermediate 4

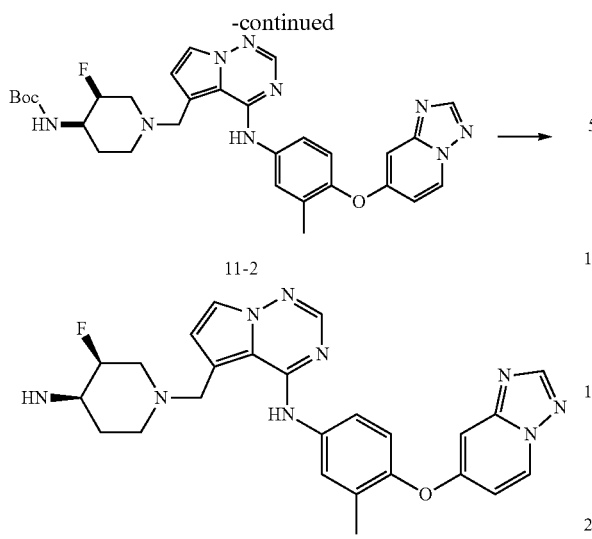

Example 23 or Example 24

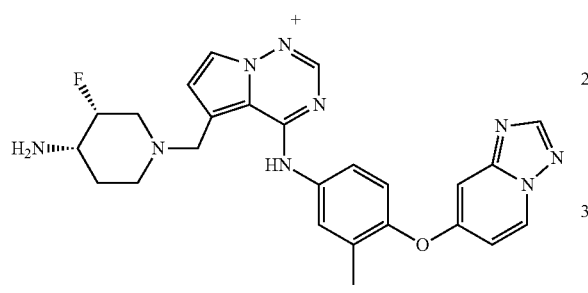

Example 24 or Example 23

Step 1

Intermediate 4 (250 mg, 565.23 μmol, 1.00 eq, HCl) and compound 11-1 (123 mg, 565.23 μmol, 1.00 eq) were added to acetonitrile (5 mL), and then N,N-diisopropylethylamine (219 mg, 1.70 mmol, 295 μL, 3.00 eq) was added at 0° C. The reaction mixture was stirred at 25° C. for 1 hour. LCMS showed that the reaction was completed. The reaction mixture was directly concentrated under reduced pressure to dryness to obtain a crude product, and the crude product was slurried with a mixed solvent (petroleum ether:ethyl acetate=1:1, 10 mL) to obtain compound 11-2. MS: m/z 610.1 [M+Na]$^+$.

Step 2

Compound 11-2 (450 mg, 765.77 μmol, 1.00 eq) was dissolved in dichloromethane (10 mL), and trifluoroacetic acid (1.54 g, 13.51 mmol, 1 mL, 17.64 eq) was added. The reaction mixture was stirred at 25° C. for 16 hours. LCMS showed that the reaction was completed. The reaction mixture was concentrated to remove dichloromethane, diluted with saturated sodium bicarbonate aqueous solution (20 mL), and then extracted with ethyl acetate (10 mL*2). The organic phase was washed with saturated brine (10 mL), dried over anhydrous sodium sulfate and filtered. The filtrate was concentrated to obtain a crude product (220 mg). The crude product was separated by SFC to obtain Example 23 (SFC: $t_R$=1.409 min, SFC detection conditions: chromatographic column: Chiralpak AD-3 50×4.6 mm 3 m; mobile phase: A phase: carbon dioxide, B phase: isopropanol (containing 0.05% ethanolamine); gradient: keeping 40%; flow rate: 4 ml per minute; column temperature: 35° C.) and Example 24 (SFC: $t_R$=1.888 min, the detection conditions were the same as in Example 23). Example 23: $^1$H NMR (400 MHz, DMSO-d$_6$) δ 11.65 (s, 1H), 8.93 (d, J=7.2 Hz, 1H), 8.38 (s, 1H), 7.96 (s, 1H), 7.80-7.71 (m, 2H), 7.67 (d, J=2.4 Hz, 1H), 7.20 (d, J=8.4 Hz, 1H), 7.10-6.94 (m, 1H), 6.86-6.73 (m, 1H), 6.72-6.60 (m, 1H), 4.76-4.54 (m, 1H), 3.92-3.71 (m, 2H), 3.05 (br d, J=11.2 Hz, 1H), 2.92-2.61 (m, 2H), 2.40-2.22 (m, 2H), 2.18 (s, 3H), 1.70 (br s, 2H). MS: m/z 488.1 [M+H]$^+$. Example 24: $^1$H NMR (400 MHz, DMSO-d$_6$) δ 11.64 (s, 1H), 8.94 (d, J=7.6 Hz, 1H), 8.39 (s, 1H), 7.96 (s, 1H), 7.80-7.72 (m, 2H), 7.68 (d, J=2.4 Hz, 1H), 7.20 (d, J=8.8 Hz, 1H), 7.03 (dd, J=2.4, 7.6 Hz, 1H), 6.79 (d, J=2.4 Hz, 1H), 6.67 (d, J=2.4 Hz, 1H), 4.74-4.59 (m, 1H), 3.90-3.74 (m, 2H), 3.06 (br d, J=10.8 Hz, 1H), 2.95-2.69 (m, 2H), 2.39-2.24 (m, 2H), 2.18 (s, 3H), 1.71 (br s, 2H). MS: m/z 488.2 [M+H]$^+$.

Examples 25 and 26

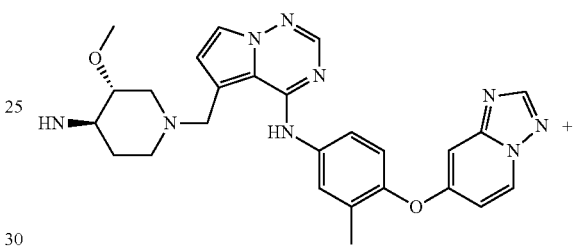

Example 25 or Example 26

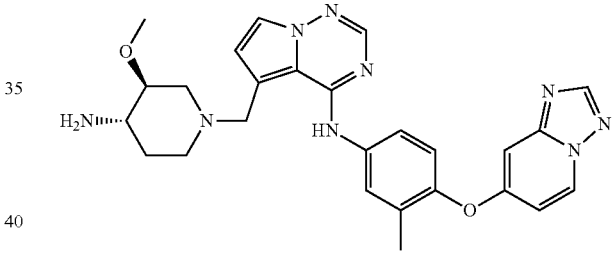

Example 26 or Example 25

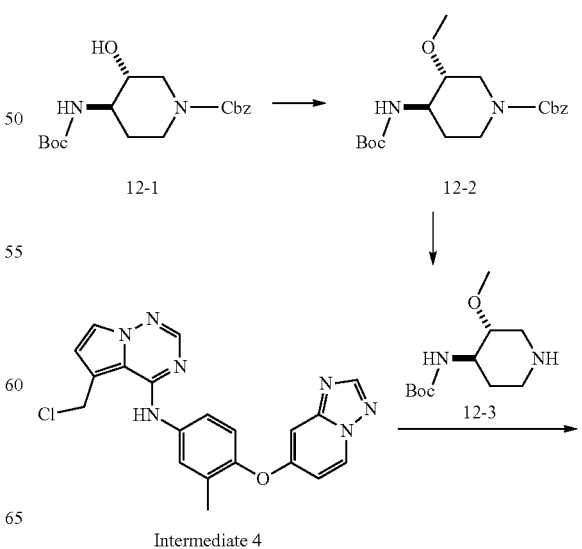

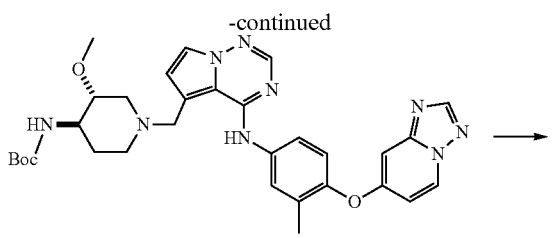

12-4

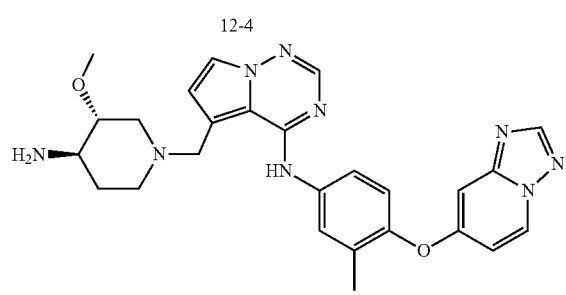

Example 25 or Example 26

+

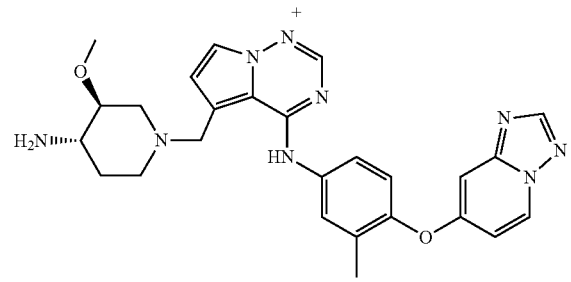

Example 26 or Example 25

Step 1

Compound 12-1 (100 mg, 285.38 μmol, 1.00 eq) was dissolved in tetrahydrofuran (1 mL), and sodium hydrogen (34 mg, 856.14 μmol, 60% purity, 3.00 eq) was added in batches at 0° C. Then a solution of methyl iodide (61 mg, 428.07 mol, 27 μL, 1.50 eq) in tetrahydrofuran (0.1 mL) was added slowly at 0° C., and the reaction mixture was stirred at 25° C. for 1 hour under nitrogen protection. TLC detected that the reaction was completed. The reaction mixture was quenched with a saturated aqueous ammonium chloride solution (1 mL) at 0° C., diluted with water (20 mL), and extracted with ethyl acetate (20 mL). The organic phase was washed with saturated brine organic phase (20 mL), dried with anhydrous sodium sulfate and filtered. The filtrate was concentrated under reduced pressure to obtain compound 12-2. $^1$H NMR (400 MHz, CDCl$_3$-d) δ 7.22-7.13 (m, 5H), 4.97 (br s, 2H), 4.41 (br s, 1H), 4.14-3.88 (m, 1H), 3.66-3.37 (m, 1H), 3.25-3.22 (m, 3H), 2.88 (br d, J=7.6 Hz, 1H), 2.58 (br s, 2H), 1.51 (br s, 2H), 1.30-1.28 (m, 9H).

Step 2

Compound 12-2 (120 mg, 329.28 μmol, 1.00 eq) was dissolved in anhydrous methanol (5 mL), and wet palladium hydroxide/carbon (50 mg, 20% purity) was added under nitrogen protection. The reaction mixture was hydrogenated at 25° C., 15 psi for 16 hours. TLC detected that the reaction was completed. The reaction mixture was filtered through diatomite. The filter cake was washed with methanol, and the filtrate was concentrated under reduced pressure to obtain compound 12-3. $^1$H NMR (400 MHz, CDCl$_3$-d) δ 4.45 (br s, 1H), 3.21 (s, 3H), 3.08 (br d, J=3.6 Hz, 2H), 2.91-2.82 (m, 2H), 2.55-2.40 (m, 2H), 2.06-1.91 (m, 1H), 1.31 (s, 9H).

Step 3

Intermediate 4 (80 mg, 180.87 μmol, 1.00 eq, HCl) and compound 12-3 (62 mg, 271.31 μmol, 1.50 eq) were added to acetonitrile (5 mL), and then N,N-diisopropylethylamine (70 mg, 542.61 μmol, 94 μL, 3.00 eq) was added at 0° C. The reaction mixture was stirred at 25° C. for 1 hour. LCMS showed that the reaction was completed. The reaction mixture was directly concentrated under reduced pressure to obtain a crude product. The crude product was separated by preparative HPLC (under the condition of formic acid) to obtain compound 12-4. MS: m/z 622.2 [M+Na]$^+$.

Step 4

Compound 12-4 (60 mg, 100.05 μmol, 1.00 eq) was dissolved in dichloromethane (5 mL), and trifluoroacetic acid (1.54 g, 13.51 mmol, 1 mL, 134.99 eq) was added. The reaction mixture was stirred at 25° C. for 1 hour. LCMS showed that the reaction was completed. The reaction mixture was concentrated to remove dichloromethane, diluted with saturated sodium bicarbonate aqueous solution (20 mL), and then extracted with ethyl acetate (20 mL*2). The organic phase was washed with saturated brine (20 mL), dried over anhydrous sodium sulfate and filtered. The filtrate was concentrated to obtain a crude product (30 mg). The crude product was separated by SFC to obtain Example 25 (SFC: t$_R$=7.745 min, SFC detection conditions: chromatographic column: Chiralpak IG-3 100×4.6 mm 3 m; mobile phase: A phase: carbon dioxide, B phase: ethanol (containing 0.05% ethanolamine); gradient: keeping 40%; flow rate: 3.2 ml per minute; column temperature: 35° C.) and Example 26 (SFC: t$_R$=9.120 min, the detection conditions were the same as in Example 25). Example 25: $^1$H NMR (400 MHz, DMSO-d$_6$) δ 11.69 (br s, 1H), 8.94 (d, J=7.6 Hz, 1H), 8.38 (s, 1H), 7.98 (s, 1H), 7.81 (br d, J=8.8 Hz, 1H), 7.74 (d, J=2.4 Hz, 1H), 7.68 (d, J=2.4 Hz, 1H), 7.24 (d, J=8.8 Hz, 1H), 7.04 (dd, J=2.4, 7.6 Hz, 1H), 6.80 (d, J=2.4 Hz, 1H), 6.68 (d, J=2.8 Hz, 1H), 3.97-3.92 (m, 1H), 3.79-3.74 (m, 1H), 3.29 (s, 3H), 3.14 (br s, 1H), 2.95-2.93 (m, 1H), 2.80 (br s, 1H), 2.20 (s, 3H), 2.10-2.04 (m, 1H), 1.94-1.84 (m, 1H), 1.48-1.36 (m, 1H). MS: m/z 500.1 [M+H]$^+$. Example 26: $^1$H NMR (400 MHz, DMSO-d$_6$) δ 11.70 (br s, 1H), 8.94 (d, J=7.6 Hz, 1H), 8.38 (s, 1H), 7.98 (s, 1H), 7.79-7.83 (m, 1H), 7.74 (s, 1H), 7.68 (d, J=2.4 Hz, 1H), 7.24 (d, J=8.8 Hz, 1H), 7.04 (dd, J=2.4, 7.6 Hz, 1H), 6.80 (d, J=2.4 Hz, 1H), 6.67 (d, J=2.4 Hz, 1H), 3.94 (br d, J=13.2 Hz, 1H), 3.76 (br d, J=13.6 Hz, 1H), 3.28 (s, 3H), 3.16 (br d, J=10.4 Hz, 1H), 2.90 (br s, 1H), 2.79 (br s, 1H), 2.20 (s, 3H), 2.08 (br s, 1H), 1.88-1.94 (m, 1H), 1.43 (br d, J=9.6 Hz, 1H). MS: m/z 500.1 [M+H]$^+$.

Examples 27 and 28

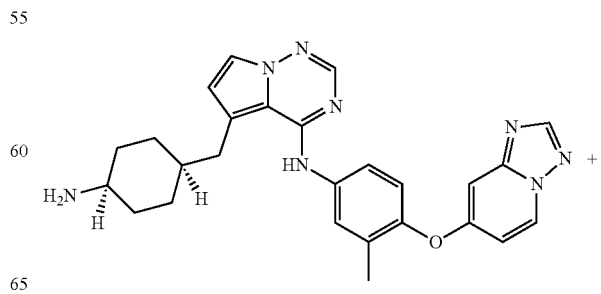

Example 27 or Example 28

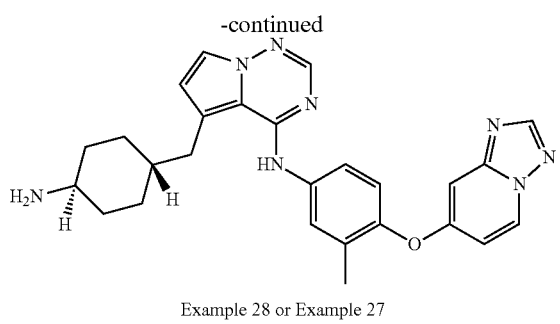

Example 28 or Example 27

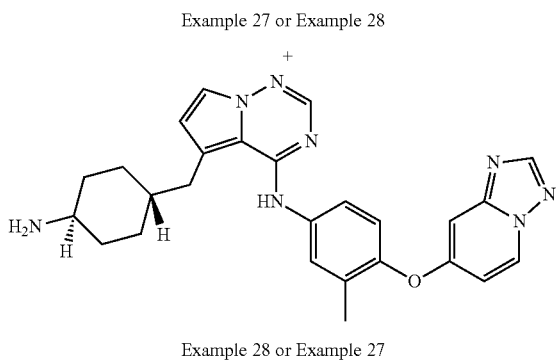

Example 28 or Example 27

Step 1

Compound 13-1 (0.30 g, 1.42 mmol, 1.00 eq) was dissolved in tetrahydrofuran (3 mL), and 9-boronbicyclo(3,3,1)-nonane (0.5 M, 12 mL, 4.23 eq) was added at 0° C. The reaction mixture was stirred at 25° C. for 1 hour. After TLC detected the disappearance of the raw materials, water (1 mL) was slowly added at 0° C. to quench the reaction mixture. Then intermediate 2 (0.10 g, 229.22 μmol, 1.61 eq), potassium phosphate (2.11 g, 9.94 mmol, 7 eq), 1,1-bis(tert-butylphosphorus)ferrocene palladium chloride (185.07 mg, 283.96 μmol, 0.20 eq) and N,N-dimethylformamide (3 mL) were added. All the reaction mixture was purged with nitrogen three times, and then heated to 100° C., and reacted for 15 hours. After LCMS and TLC detected that the reaction was completed, the reaction mixture was poured into water (50 mL), and then extracted with ethyl acetate (50 mL*3). The organic phases were combined, washed with saturated brine (50 mL), dried over anhydrous sodium sulfate, and concentrated to obtain a brown oily product. The product was further separated and purified by column chromatography (ISCO®; 4 g SepaFlash® fast silica gel column, mobile phase: 0 to 100% ethyl acetate/petroleum ether, flow rate: 18 mL/min) to obtain compound 13-2 (150.0 mg, crude product, brown oily product). MS: m/z 569.1 [M+H]$^+$.

Step 2

Compound 13-2 (0.15 g, 263.77 μmol, 1.00 eq) was dissolved in dichloromethane (3 mL), and trifluoroacetic acid (1.54 g, 13.51 mmol, 1.0 mL, 51.20 eq) was added. The reaction mixture was stirred at 25° C. for 1 hour. LCMS detected that the reaction was completed. The reaction mixture was quenched with saturated sodium bicarbonate (50 mL) and then extracted with ethyl acetate (50 mL*3). The organic phases were combined, washed with saturated brine (50 mL), dried over anhydrous sodium sulfate and concentrated to obtain a crude product. The crude product was separated by SFC to obtain Example 27 (SFC: $t_R$=1.293 min, SFC detection conditions: chromatographic column: Chiralpak AD-3 50×4.6 mm 3 m; mobile phase: A phase: carbon dioxide, B phase: ethanol (containing 0.05% ethanolamine); gradient: keeping 40%; flow rate: 4 ml per minute; column temperature: 35° C.) and Example 28 (SFC: $t_R$=2.314 min, the detection conditions were the same as in Example 27). Example 27: $^1$H NMR (400 MHz, METHANOL-d$_4$) δ 8.76 (d, J=6.8 Hz, 1H), 8.31 (s, 1H), 7.81 (s, 1H), 7.73-7.54 (m, 3H), 7.19 (d, J=8.8 Hz, 1H), 7.11 (dd, J=2.4, 7.2 Hz, 1H), 6.84 (d, J=3.2 Hz, 1H), 6.62 (s, 1H), 3.15 (s, 1H), 3.09 (d, J=7.2 Hz, 2H), 2.25 (s, 3H), 2.05 (d, J=6.4 Hz, 2H), 1.77-1.71 (m, 4H), 1.64-1.55 (m, 3H). Example 28: $^1$H NMR (400 MHz, METHANOL-d$_4$) δ 8.63 (d, J=7.6 Hz, 1H), 8.18 (s, 1H), 7.68 (s, 1H), 7.54 (br s, 1H), 7.46 (br d, J=2.4 Hz, 2H), 7.07 (d, J=8.4 Hz, 1H), 6.98 (dd, J=2.4, 7.6 Hz, 1H), 6.74 (d, J=2.4 Hz, 1H), 6.47 (d, J=2.8 Hz, 1H), 2.86 (d, J=7.2 Hz, 2H), 2.57 (s, 1H), 2.13 (s, 3H), 1.85-1.69 (m, 4H), 1.52 (s, 1H), 1.11-1.00 (m, 4H). MS: m/z 469.1 [M+H]$^+$.

Example 29

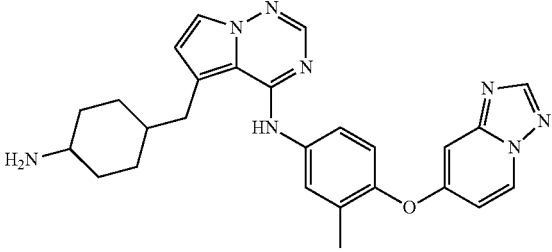

Example 29

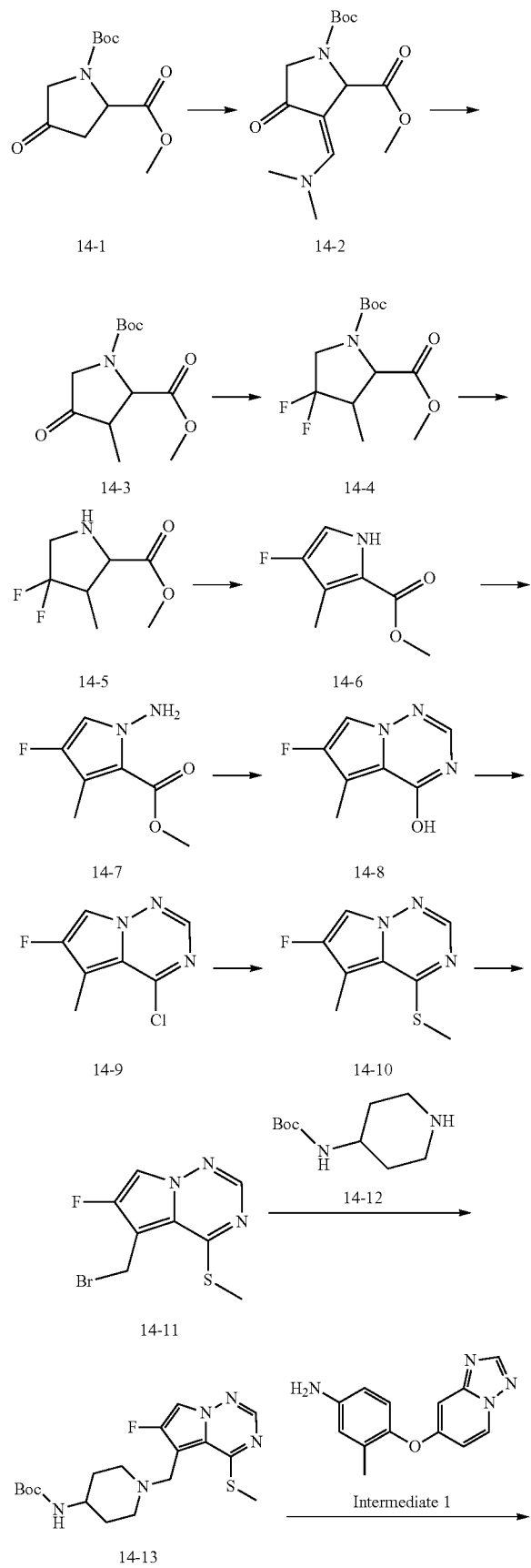

14-1
14-2
14-3
14-4
14-5
14-6
14-7
14-8
14-9
14-10
14-11
14-12
14-13

Intermediate 1

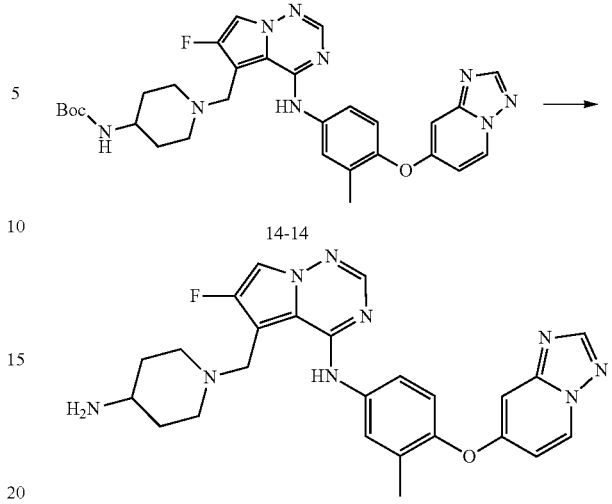

14-14

Example 29

Step 1

A solution of compound 14-1 (10 g, 41.11 mmol, 1 eq) in DMF-DMA (30 mL) was stirred at 100° C. for 1.5 hours. After LCMS detected that the reaction was completed, the reaction mixture was concentrated under reduced pressure and evaporated to dryness to obtain a crude product. The crude product was purified by column chromatography (ISCO®; 40 g SepaFlash® fast silica gel column, mobile phase: 0 to 60% ethyl acetate/petroleum ether, flow rate: 35 mL/min) to obtain compound 14-2. $^1$H NMR (400 MHz, CDCl$_3$-d) δ 7.23-7.18 (m, 1H), 3.64 (s, 3H), 3.63 (s, 3H), 2.89 (s, 1H), 2.82 (s, 1H), 1.38 (s, 9H). MS: m/z 298.9 [M+H]$^+$.

Step 2

Dry palladium-carbon (3 g, 33.39 mmol, 10% purity, 1 eq) was added to a solution of compound 14-2 (9.96 g, 33.39 mmol, 1 eq) in anhydrous tetrahydrofuran (100 mL). The reaction mixture was purged three times and then reacted at 20° C. for 18 hours under hydrogen atmosphere. After TLC detected that the reaction was completed, the reaction mixture was filtered through diatomite, and the filtrate was concentrated under reduced pressure and evaporated to dryness to obtain a crude product. The crude product was purified by column chromatography (ISCO®; 40 g Sepa-Flash® fast silica gel column, mobile phase: 0 to 50% ethyl acetate/petroleum ether, flow rate: 40 mL/min) to obtain compound 14-3. $^1$H NMR (400 MHz, DMSO-d$_6$) δ 4.14 (br d, J=7.0 Hz, 1H), 4.00-3.88 (m, 2H), 3.33 (s, 3H), 3.29-3.11 (m, 2H), 2.83-2.62 (m, 1H), 1.42 (br s, 9H), 0.90 (br d, J=7.0 Hz, 4H).

Step 3

Diethylaminosulfur trifluoride (24.25 g, 150.42 mmol, 19.87 mL, 9 eq) was added dropwise slowly to a solution of compound 14-3 (4.30 g, 16.71 mmol, 1 eq) in 1,2-dichloroethane (50 mL) at −78° C., the reaction mixture was heated to 20° C. slowly and reacted for 48 hours. After TLC detected that the reaction was completed, the reaction mixture was added with a saturated sodium bicarbonate solution (100 mL) to quench the reaction, and extracted with 1,2-dichloroethane (40 mL*3). The combined organic phase was washed with saturated brine (50 mL), dried over anhydrous sodium sulfate and filtered. The filtrate was concentrated under reduced pressure to obtain a crude product. The crude product was purified by column chromatography (ISCO®;

40 g SepaFlash® fast silica gel column, mobile phase: 0 to 10% ethyl acetate/petroleum ether, flow rate: 40 mL/min) to obtain compound 14-4.

Step 4

A solution of compound 14-4 (3.92 g, 14.04 mmol, 1 eq) in hydrochloric acid/ethyl acetate (40 mL) was stirred and reacted at 20° C. for 18 hours. After LCMS detected that the reaction was completed, the reaction mixture was concentrated under reduced pressure, and evaporated to dryness to obtain compound 14-5. MS: m/z 215.8 [M+H]$^+$.

Step 5

Triethylamine (1.60 g, 15.81 mmol, 2.20 mL, 1.1 eq) was added to a solution of compound 14-5 (3.1 g, 14.38 mmol, 1 eq, HCl) in anhydrous tetrahydrofuran (100 mL). The reaction mixture was reacted at 20° C. for 0.5 hour, and then manganese dioxide (11.25 g, 129.39 mmol, 9 eq) was added. The reaction mixture was reacted continuously at 80° C. for 4 hours. After LCMS detected that the reaction was completed, the reaction mixture was filtered through diatomite, and the filtrate was diluted with water (40 mL), and extracted with ethyl acetate (50 mL*3). The combined organic phase was washed with saturated brine (80 mL), dried over anhydrous sodium sulfate and filtered. The filtrate was concentrated under reduced pressure and evaporated to dryness to obtain compound 14-6. $^1$H NMR (400 MHz, CDCl$_3$-d) δ 8.71 (br s, 1H), 6.58 (t, J=3.6 Hz, 1H), 3.82-3.76 (m, 3H), 2.18 (s, 3H). MS: m/z 158.0 [M+H]$^+$.

Step 6

Sodium hydrogen (330.91 mg, 8.27 mmol, 60% purity, 1.3 eq) was added to anhydrous DMF (10 mL) 0° C., and then compound 14-6 (1.00 g, 6.36 mmol, 1 eq) was added in batches. The reaction mixture was reacted at 20° C. for 1 hour. Finally, 2,4-dinitrophenylhydroxylamine (1.52 g, 7.64 mmol, 1.2 eq) was added slowly to the above-mentioned reaction mixture at 0° C. and stirred at 20° C. for 20 hours. LCMS detected that the reaction was completed. The reaction was quenched by adding saturated aqueous ammonium chloride solution (10 mL) at 0° C. The reaction mixture was filtered, and the filtrate was diluted with water (15 mL) and ethyl acetate (25 mL*2), filtered, and extracted with ethyl acetate (20 mL*2). The combined organic phase was washed with water (20 mL) and saturated brine (20 mL), dried over anhydrous sodium sulfate and filtered. The filtrate was concentrated under reduced pressure and evaporated to dryness to obtain a crude product of compound 14-7. $^1$H NMR (400 MHz, DMSO-d$_6$) δ 6.99 (br s, 1H), 3.77 (s, 3H), 2.12 (s, 3H). MS: m/z 172.0 [M+H]$^+$.

Step 7

Formamidine acetate (1.39 g, 13.36 mmol, 2 eq) was added to a solution of compound 14-7 (1.15 g, 6.68 mmol, 1 eq) in isopropanol (10 mL), and the reaction mixture was reacted at 90° C. for 14 hours. After LCMS detected that the reaction was completed, the reaction mixture was cooled to room temperature, and water was slowly added, and a solid was precipitated. The mixture was filtered, and the filter residue was washed with petroleum ether, concentrated and dried under reduced pressure to obtain compound 14-8. $^1$H NMR (400 MHz, DMSO-d$_6$) δ 11.63 (br s, 1H), 7.80 (s, 1H), 7.60 (d, J=3.2 Hz, 1H), 2.32 (s, 3H). MS: m/z 167.9 [M+H]$^+$.

Step 8

N,N-diisopropylethylamine (445.39 mg, 3.45 mmol, 600.25 µL, 0.8 eq) and phosphorus oxychloride (1.14 g, 7.43 mmol, 690.91 µL, 1.73 eq) were sequentially added to a solution of compound 14-8 (0.72 g, 4.31 mmol, 1 eq) in anhydrous toluene (10 mL), and the reaction mixture was reacted at 115° C. for 17 hours. After LCMS detected that the reaction was completed, the reaction mixture was concentrated under reduced pressure to remove most of phosphorus oxychloride, then added with ice-cold sodium bicarbonate solution (6 mL), diluted with water (6 mL), and extracted with ethyl acetate (15 mL*2). The combined organic phase was washed with saturated brine (20 mL), dried over anhydrous sodium sulfate and filtered. The filtrate was concentrated under reduced pressure to obtain compound 14-9. MS: m/z 185.9 [M+H]$^+$.

Step 9

Sodium thiomethoxide (778.50 mg, 4.74 mmol, 1.1 eq) was added to a solution of compound 14-9 (0.8 g, 4.31 mmol, 1 eq) in anhydrous tetrahydrofuran (20 mL) at 0° C., and the reaction mixture was reacted at 0° C. to 20° C. for 15 hours. After LCMS detected that the reaction was completed, the reaction mixture was diluted with water (20 mL), and extract with ethyl acetate (20 mL*4). The combined organic phase was washed with saturated brine (30 mL), dried over anhydrous sodium sulfate and filtered. The filtrate was concentrated under reduced pressure to obtain a crude product. The crude product was purified by column chromatography (ISCO®; 12 g SepaFlash® fast silica gel column, mobile phase: 0 to 30% ethyl acetate/petroleum ether, flow rate: 30 mL/min) to obtain compound 14-10. $^1$H NMR (400 MHz, CDCl$_3$-d) δ 8.04 (s, 1H), 7.38 (d, J=3.2 Hz, 1H), 2.56 (s, 3H), 2.41 (s, 3H). MS: m/z 197.8 [M+H]$^+$.

Step 10

Azobisisobutyronitrile (12.49 mg, 76.05 µmol, 0.1 eq) and N-bromosuccinimide (148.89 mg, 836.58 µmol, 1.1 eq) were added to a solution of compound 14-10 (0.15 g, 760.52 µmol, 1 eq) in carbon tetrachloride (3 mL) under N$_2$ protection, and the reaction mixture was reacted at 100° C. for 1 hour. After LCMS detected that the reaction was completed, the reaction mixture was concentrated under reduced pressure, and evaporated to dryness to obtain compound 14-11. $^1$H NMR (400 MHz, CDCl$_3$-d) δ 8.17 (s, 1H), 7.40 (d, J=3.0 Hz, 1H), 4.84 (s, 2H), 2.64 (s, 3H). MS: m/z 278.8 [M+H]$^+$.

Step 11

N,N-diisopropylethylamine (78.63 mg, 608.41 µmol, 105.97 µL, 1.2 eq) was added to a solution of compound 14-12 (121.85 mg, 608.41 µmol, 1.2 eq) in acetonitrile (5 mL), and then compound 14-11 (0.14 g, 507.01 µmol, 1.0 eq) was added slowly. The reaction mixture was stirred at 20° C. for 1 hour. After LCMS detected that the reaction was completed, the reaction mixture was concentrated under reduced pressure to remove the solvent to obtain compound 14-13. MS: m/z 396.0 [M+H]$^+$.

Step 12

Compound 14-13 (0.21 g, 530.98 µmol, 1 eq), intermediate 1 (153.09 mg, 637.18 µmol, 1.2 eq), and a solution of mercury chloride (0.32 g, 1.18 mmol, 58.82 µL, 2.22 eq) in anhydrous toluene (6 mL) were reacted at 120° C. for 18 hours under N$_2$ protection. After LCMS detected that the reaction was completed, the reaction mixture was concentrated under reduced pressure, and evaporated to dryness to obtain compound 14-14. MS: m/z 588.1 [M+H]$^+$.

Step 13

A solution of compound 14-14 (0.32 g, 544.54 µmol, 1 eq) in hydrochloric acid/ethyl acetate (10 mL) was reacted at 20° C. for 2 hours. After LCMS detected that the reaction was completed, the reaction mixture was concentrated under reduced pressure, and evaporated to dryness to obtain a crude. The crude was prepared by preparative HPLC (under the condition of formic acid) to obtain Example 29. $^1$H NMR (400 MHz, DMSO-d$_6$) δ 11.77 (br s, 1H), 8.95 (d, J=7.6 Hz, 1H), 8.39 (s, 2H), 8.09 (s, 1H), 7.89 (d, J=3.0 Hz, 1H), 7.79-7.68 (m, 2H), 7.23 (d, J=9.6 Hz, 1H), 7.04 (dd, J=2.4, 7.4 Hz, 1H), 6.81 (d, J=2.4 Hz, 1H), 3.78 (s, 2H), 3.11 (br d, J=11.0 Hz, 2H), 3.01 (br s, 1H), 2.24 (br s, 2H), 2.21 (s, 3H), 1.93 (br d, J=11.0 Hz, 2H), 1.57 (br d, J=11.0 Hz, 2H). MS: m/z 488.1 [M+H]⁺.

Example 30

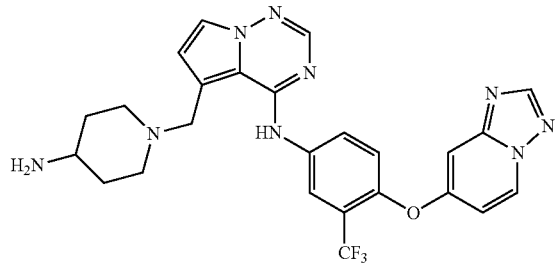 [SMILES: NC1CCN(Cc2ccn3ncnc(Nc4ccc(Oc5ccn6ncnc6c5)c(C(F)(F)F)c4)c23)CC1]

Example 30

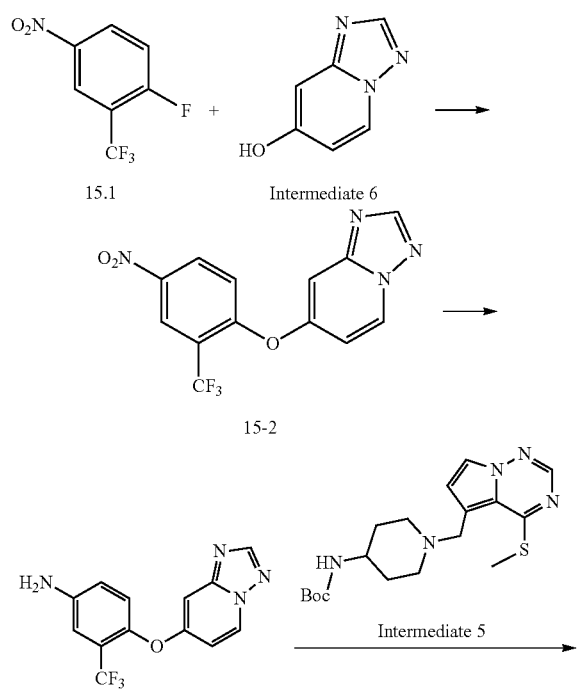

Example 30

Step 1

Compound 15-1 (0.08 g, 382.60 μmol, 52.63 μL, 1.00 eq) and intermediate 6 (51.70 mg, 382.60 μmol, 1.00 eq) were dissolved in N,N-dimethylformamide (4 mL), and potassium carbonate (158.63 mg, 1.15 mmol, 3.00 eq) was added. The reaction mixture was stirred and reacted at 25° C. for 2 hours. TLC (petroleum ether:ethyl acetate=2:1) detected that the reaction was completed, and the reaction mixture was poured into water (100 mL), and then extracted with ethyl acetate (50 mL*3). The organic phases were combined, washed with saturated brine (50 mL), dried over anhydrous sodium sulfate and concentrated to obtain a crude product. The crude product was and purified by column chromatography (ISCO®; 4 g SepaFlash® fast silica gel column, mobile phase: 0 to 30% ethyl acetate/petroleum ether, flow rate: 18 mL/min) to obtain a crude product of compound 15-2.

Step 2

Compound 15-2 (0.1 g, 308.44 μmol, 1.00 eq) was dissolved in ethanol (3 mL) and water (3 mL), and iron powder (86.12 mg, 1.54 mmol, 5.00 eq) and ammonium chloride (82.49 mg, 1.54 mmol, 5.00 eq) were added. The reaction mixture was reacted at 50° C. for 1 hours. LCMS detected that the reaction completed, and the reaction mixture was filtered. The filtrate was concentrated, poured into water (50 mL), and then extracted with ethyl acetate (50 mL*3). The organic phases were combined, washed with saturated brine (50 mL), dried over anhydrous sodium sulfate and concentrated to obtain compound 15-3. MS: m/z 295.1 [M+H]⁺.

Step 3

Compound 15-3 (15.59 mg, 52.98 μmol, 1.00 eq) and intermediate 5 (0.02 g, 52.98 μmol, 1 eq) were dissolved in toluene (2 mL), and mercury chloride (25 mg, 92.08 μmol, 4.60 μL, 1.74 eq) was added. The reaction mixture was stirred at 120° C. for 16 hours. LCMS detected that the reaction was completed. The reaction mixture was filtered, and the filtrate was concentrated, and separated and purified by preparative HPLC (under the condition of formic acid) to obtain Example 30. ¹H NMR (400 MHz, DMSO-d₆) δ 12.34 (br s, 1H), 8.99 (d, J=7.6 Hz, 1H), 8.45 (s, 1H), 8.38 (d, J=2.4 Hz, 1H), 8.35 (s, 1H), 8.14-8.07 (m, 1H), 8.04 (s, 1H), 7.73 (d, J=2.8 Hz, 1H), 7.52 (d, J=8.8 Hz, 1H), 7.15 (d, J=2.8 Hz, 1H), 7.08 (dd, J=2.4, 7.6 Hz, 1H), 6.70 (d, J=2.4 Hz, 1H), 3.84 (s, 3H), 3.17 (s, 2H), 3.10 (d, J=10.8 Hz, 2H), 2.94 (br s, 1H), 2.20 (br s, 2H), 1.88 (br d, J=12.0 Hz, 2H), 1.47 (br d, J=10.4 Hz, 2H). MS: m/z 524.1 [M+H]⁺.

Example 31

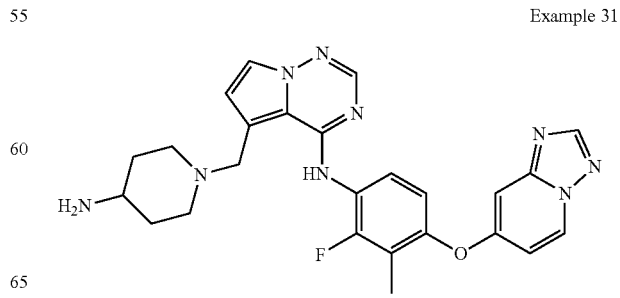

Example 31

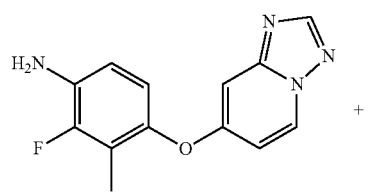

Intermediate 7

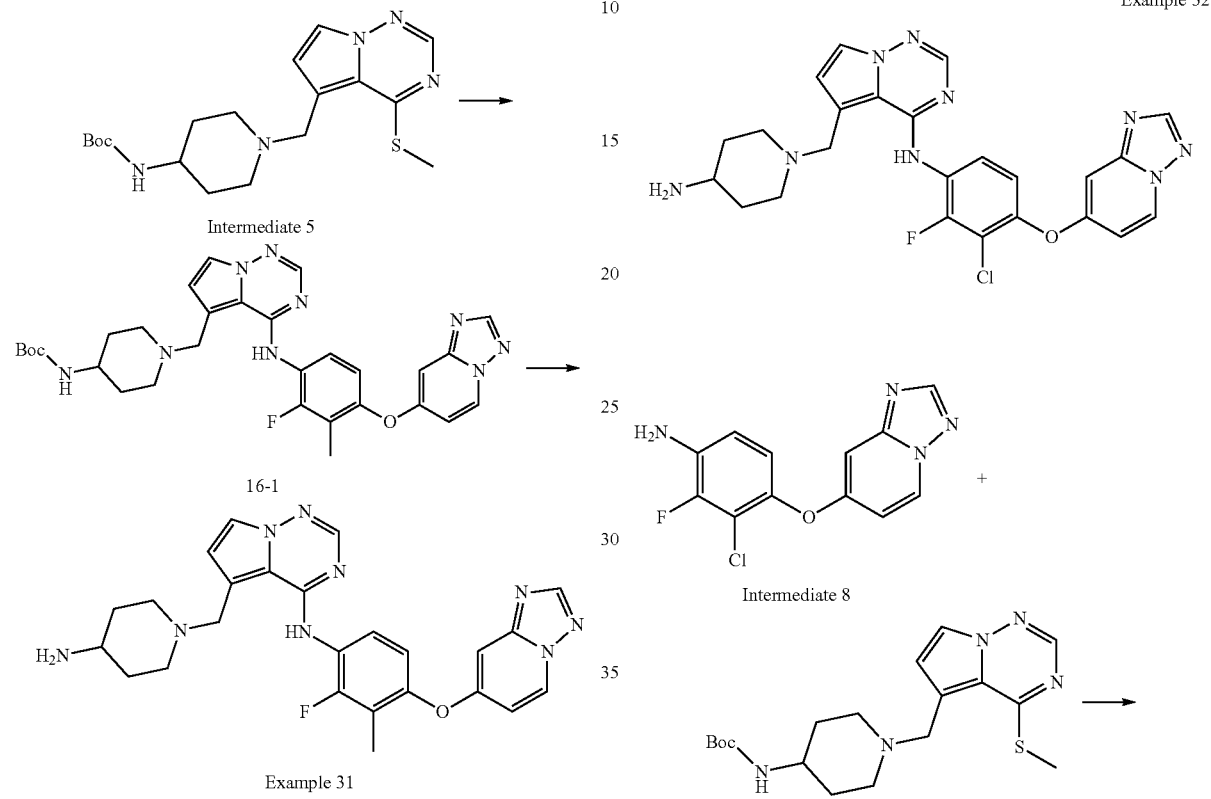

7.12-7.06 (m, 2H), 6.97 (d, J=2.8 Hz, 1H), 6.69 (d, J=2.4 Hz, 1H), 3.81 (s, 2H), 3.08-2.91 (m, 3H), 2.19-2.13 (m, 5H), 1.86 (d, J=11.6 Hz, 2H), 1.58-1.37 (m, 3H). MS: m/z 488.1 [M+H]$^+$.

Example 32

Step 1

Intermediate 7 (0.62 g, 2.40 mmol, 1.00 eq) and potassium tert-butoxide (808.2 mg, 7.20 mmol, 3.00 eq) were dissolved in N,N-dimethylformamide (8 mL), and intermediate 5 was added (1.09 g, 2.88 mmol, 1.20 eq). The reaction mixture was stirred at 25° C. for 1 hour. LCMS and TLC (petroleum ether:ethyl acetate=0:1) detected that the reaction was completed. The reaction mixture was diluted with water (200 mL), and then extracted with ethyl acetate (100 mL*3). The organic phases were combined, washed with saturated brine (50 mL), dried over anhydrous sodium sulfate and concentrated to obtain a crude product. The crude product was purified by column chromatography (ISCO®; 40 g SepaFlash® fast silica gel column, mobile phase: 0 to 70% ethyl acetate/petroleum ether, flow rate: 40 mL/min) to obtain compound 16-1. MS: m/z 588.3 [M+H]$^+$.

Step 2

Compound 16-1 (0.40 g, 680.68 μmol, 1.00 eq) was added to hydrogen chloride/ethyl acetate (4 M, 20.00 mL, 117.53 eq), and stirred at 25° C. for 10 hours. LCMS detected that the reaction was completed. The reaction mixture was concentrated, and then separated and purified by preparative HPLC (under the condition of formic acid) to obtain Example 31. $^1$H NMR (400 MHz, DMSO-d$_6$) δ 11.95 (s, 1H), 8.97 (d, J=7.2 Hz, 1H), 8.42 (s, 1H), 8.37 (s, 1H), 8.09 (t, J=8.8 Hz, 1H), 7.95 (s, 1H), 7.70 (d, J=2.4 Hz, 1H), Example 32

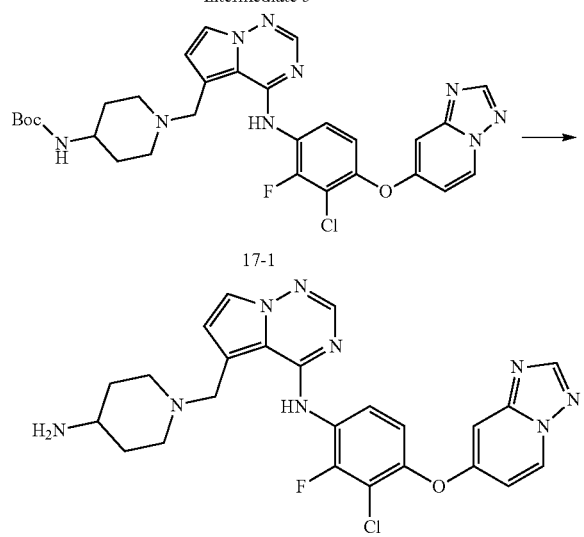

Step 1

Intermediate 8 (258.37 mg, 927.14 μmol, 1.00 eq) dissolved in N,N-dimethylformamide (10 mL), and sodium hydrogen (185.41 mg, 4.64 mmol, 60% purity 5.00 eq) was slowly added. The mixture was stirred at 25° C. for 1 hour, and then intermediate 5 (0.35 g, 927.14 μmol, 1.00 eq) was added. The reaction mixture was continuously stirred at 25° C. for 15 hours. LCMS detected that the reaction was completed. The reaction mixture was diluted with water (200 mL), and then extracted with ethyl acetate (50 mL*3). The organic phases were combined, washed with saturated brine (50 mL), dried over anhydrous sodium sulfate and concentrated to obtain a crude product of compound 17-1. MS: m/z 608.1 [M+H]$^+$.

Step 2

Compound 17-1 (0.7 g, 1.15 mmol, 1.00 eq) was dissolved in dichloromethane (10 mL), and trifluoroacetic acid (3.08 g, 27.01 mmol, 2 mL, 23.46 eq) was added. The reaction mixture was stirred at 25° C. for 12 hours. LCMS detected that the reaction was completed. The reaction mixture was concentrated and purified by column chromatography (ISCO®; 40 g SepaFlash® fast silica gel column, mobile phase: 0 to 10% methanol/dichloromethane, flow rate: 30 mL/min) to obtain Example 32. $^1$H NMR (400 MHz, DMSO-$d_6$) δ 12.38 (s, 1H), 9.01 (d, J=8.4 Hz, 1H), 8.45 (s, 1H), 8.19 (t, J=8.8 Hz, 1H), 7.97 (s, 1H), 7.73 (d, J=2.4 Hz, 1H), 7.34 (dd, J=1.6, 9.2 Hz, 1H), 7.18-7.10 (m, 2H), 6.71 (d, J=2.8 Hz, 1H), 3.82 (s, 2H), 3.00 (d, J=12.0 Hz, 2H), 2.86 (s, 1H), 2.22-2.14 (m, 2H), 1.81 (d, J=11.6 Hz, 2H), 1.42-1.32 (m, 2H). MS: m/z 508.0 [M+H]$^+$.

Biological Activity Detection: In Vitro Evaluation

Experimental Example 1 Evaluation of Enzyme Activity

The object of this test is to detect the in vitro inhibitory activity of the compound against HER1 (ErbB1), HER2 (ErbB2) and HER4 (ErbB4). The enzymes used in this test were human ErbB1, ErbB2 and ErbB4. Eurofins Pharma Discovery Service provided the activity detection method, and the results of the inhibitory activity of the tested compound against HER1, HER2 and HER4 were shown in Table 1.

Experimental Steps and Methods (96-Well Plate):

5-fold diluted tested compound buffer (5 μL), peptide substrate poly(Glu, Tyr) (4:1) (2.5 μL), ErbB (4-20 ng, 2.5 μL), MnCl$_2$ (50 mM, 1.25 μL), dH$_2$O (3.75 μL) and [γ-$^{33}$P] ATP (10 μL) were added, and incubated at 30° C. for 10 min. 3% phosphoric acid was added to terminate the reaction, and 10 μL of the specimen was transferred to Filtermate A. The filter was washed with 75 mM phosphoric acid for three times and methanol once, and transferred to a sealed plastic bag, and a scintillation fluid mixture (4 mL) was added, The intensity of the emitted photons was detected on the scintillation luminescence counter. The photon intensity of the enzyme sample was compared with the photon intensity of the internal control sample, and the level of photon intensity reflected the strength of the tyrosine kinase activity.

TABLE 1

Results of in vitro enzyme activity screening test of the compound of the present disclosure

| Compounds | HER1 IC$_{50}$ (nM) | HER2 IC$_{50}$ (nM) | HER4 IC$_{50}$ (nM) |
|---|---|---|---|
| Example 1 | >1000 | 24 | >1000 |
| Example 4 | 161 | 12 | 156 |
| Example 5 | >1000 | 16 | >1000 |
| Example 6 | 743 | 18 | 150 |
| Example 7 | >1000 | 10 | >1000 |
| Example 8 | 385 | 10 | 184 |
| Example 9 | 325 | 11 | 201 |
| Example 16 | 861 | 7 | 535 |
| Example 18 | 509 | 4 | >1000 |
| Example 20 | 167 | 7 | 230 |
| Example 21 | 909 | 4 | >1000 |
| Example 22 | 438 | 6 | 306 |
| Example 23 | 61 | 2 | 41 |
| Example 24 | 109 | 3 | 139 |
| Example 25 | 207 | 2 | 369 |
| Example 30 | 663 | 14 | >1000 |
| Example 31 | 667 | 3 | >1000 |
| Example 32 | 284 | 2 | 356 |

Conclusion: In vitro kinase activity test showed that the compound of the present disclosure could selectively inhibit HER2, but had weak inhibitory activity on HER1 and HER4.

Experimental Example 2 Evaluation of Cell Proliferation Inhibitory Activity

Experiment object: to detect the inhibitory activity of the tested compound on cell proliferation.

Experimental principle: the luciferase in the Cell-Titer-Glo reagent uses luciferin, oxygen and ATP as reaction substrates to produce oxyluciferin and release energy in the form of light. Since the luciferase reaction requires ATP, the total amount of light produced by the reaction is proportional to the total amount of ATP that reflects cell viability.

Experimental Materials:
cell lines: NCI-N87 cell line (ATCC-CRL-5822); BT-474 cell line (ATCC-HTB-20)
Cell culture medium: RPMI 1640 medium (Invitrogen #22400-105; 10% serum Invitrogen #10090148; L-glutamine 1x, Gibco #25030-081; double antibody Hyclone #SV30010)
CellTiter-Glo® luminescence cell viability detection kit (Promega #G7573)
384-well cell culture plate (Greiner #781090)
Compound plate (LABCYTE #LP-0200)
CO$_2$ incubator (Thermo #371)
Vi-cell cell counter (Beckman Coulter)
Pipette (Eppendorf)
Pipette (Greiner)
Pipetting gun (Eppendorf)
Multifunctional microplate reader (Envision Reader)
ECHO Liquid-handling workstation (Labcyte-ECHO555)

Experimental Steps and Methods:

2.1 Day 0:

The cells were inoculated in a 384-well plate with a density of 1000 cells per well and 25 μL per well. The edge wells were not inoculated with cells, and was supplemented with 25 μL of phosphate buffer.

2.2 Day 1:

(1) The compound had a concentration of 10 mM, which was diluted with DMSO to an initial concentration of 4 mM. The compound was added to the plate with 9 μL per well.

(2) The compound was diluted with ECHO liquid-handling workstation, and each well of the cell plate was added with 125 nL of compound. Each well of the cell wells of columns 2 and 23 was added with 125 nL of DMSO, and each well of the Media wells of columns 1 and 24 was added with 125 nL of DMSO.

(3) Each well of the cell plate was supplemented with 25 μL of culture medium, and the final volume in each well of the cell plate was 50 μL. The concentration of the compound was 10 μM, which was subjected to 3 fold dilution to obtain 10 concentrations. Each concentration was duplicated in left and right wells, and the final DMSO concentration was 0.25%.

2.3 After adding the compound, it was centrifuged at 1000 rpm for 1 min. The cell plate was placed in a 37° C., 5% $CO_2$ incubator for 3 days.

2.4 Day 4:

The cell plate was taken from the incubator and equilibrated at room temperature for 30 min. 25 μL of Cell-Titer-Glo reagent was added to each well, shaken for 1 min to make it thoroughly mixed, and centrifuged at 1000 rpm for 1 min. After 10 min, the plate was read on PerkinElmer Envision, and the fluorescence reading time was set to 0.2 seconds.

Test Results: The Test Results were Shown in Table 2:

TABLE 2

Results of screening test for in vitro cell proliferation inhibitory activity of the compound of the present disclosure

| Compounds | NCI-N87 cell $IC_{50}$ (nM) | BT-474 $IC_{50}$ (nM) |
|---|---|---|
| Example 4 | 7 | 23 |
| Example 5 | 59 | 97 |
| Example 6 | 4 | ND |
| Example 7 | 27 | ND |
| Example 8 | 20 | ND |
| Example 9 | 8 | ND |
| Example 12 | 52 | ND |
| Example 15 | 66 | ND |
| Example 16 | 38 | ND |
| Example 18 | 65 | ND |
| Example 19 | 23 | ND |
| Example 20 | 9 | 88 |
| Example 21 | 19 | ND |
| Example 22 | 13 | ND |
| Example 23 | 3 | ND |
| Example 24 | 7 | ND |
| Example 25 | 14 | ND |
| Example 29 | 27 | ND |
| Example 31 | 31 | ND |
| Example 32 | 11 | 87 |

Note:
ND represented: not tested.

Conclusion: The compound of the present disclosure had a significant proliferation inhibitory activity on NCI-N87 cells and BT-474 cells.

Experimental Example 3: Evaluation of Pharmacokinetic Properties in Mice

Experimental Method

The tested compound was dissolved in 10% DMSO/45% PEG400/45% water, vortexed and sonicated to prepare a clear solution with the corresponding concentration, which was filtered through a millipore filter for use. 18 to 20 grams of Balb/c female mice were selected, and the candidate compound solution was administered intravenously at a dose of 1 or 2 mg/kg. The tested compound was dissolved in 10% NMP/10% polyethylene glycol-15-hydroxystearate/80% water, vortexed and sonicated to prepare a clear solution with the corresponding concentration, which was filtered through a millipore filter for use. 18 to 20 grams of Balb/c female mice were selected, and the candidate compound solution was administered orally at a dose of 2 or 10 mg/kg. The whole-blood for a certain period of time was collected to prepare plasma. The drug concentration was analyzed by the LC-MS/MS method, and the pharmacokinetic parameters were calculated by the Phoenix WinNonlin software (Pharsight, USA).

The test results were shown in Table 3 below:

TABLE 3

Pharmacokinetic (PK) parameters in mouse plasma of Example 4
PK parameters in mouse plasma of Example 4

| PK parameter [a] | IV (1 mg/kg) | IV (2 mg/kg) | PO (2 mg/kg) | PO (10 mg/kg) |
|---|---|---|---|---|
| $C_{max}$ (nM) | — | — | 306 | 1250 |
| $T_{1/2}$ (h) | 1.65 | 1.34 | 1.37 | 1.08 |
| $V_{dss}$ (L/kg) | 2.30 | 2.81 | — | — |
| Cl (mL/min/kg) | 19.2 | 33.0 | — | — |
| $AUC_{0\text{-}last}$ (nM · h) | 1523 | 2127 | 928 | 4277 |
| $AUC_{0\text{-}inf}$ (nM · h) | 1568 | 2152 | 950 | 4331 |
| F (%) | — | — | 22.7 | 40.2 |

Note:
[a] Cmax, the maximum drug concentration; $T_{1/2}$, half-life; $V_{dss}$, apparent volume of distribution; Cl, drug clearance rate; $AUC_{0\text{-}last}$ & $AUC_{0\text{-}inf}$, area under the time curve; F, bioavailability.
b. "—" represented not tested or no data obtained.

Experiment conclusion: The tested compound had good pharmacokinetic properties in mice.

Experimental Example 4: Evaluation of Pharmacokinetic Properties in Rats

Experimental Method:

The tested compound was dissolved in 10% NMP/10% polyethylene glycol-15-hydroxystearate/80% water, vortexed and sonicated to prepare a 2.5 mg/mL clear solution, which was filtered through a millipore filter for use. Three male SD rats were administered intravenously with the candidate compound solution at a dose of 5 mg/kg. The tested compound was dissolved in 10% polyethylene glycol-15-hydroxystearate/90% water (50 mM citrate buffer, pH 3.0), adjusted to pH of about 3.5, vortexed and sonicated to prepare a 5 mg/ml clear solution, which was filtered through a millipore filter for use. Three male SD rats were administered orally with the candidate compound solution at a dose of 50 mg/kg. The whole-blood for a certain period of time was collected to prepare plasma. The drug concentration was analyzed by the LC-MS/MS method, and the pharmacokinetic parameters were calculated by the Phoenix WinNonlin software (Pharsight, USA).

The test results were shown in Table 4 below:

TABLE 4

Pharmacokinetic (PK) parameters in rat plasma of Example 4

| PK parameter | IV (5 mg/kg) | PO (50 mg/kg) |
|---|---|---|
| $C_{max}$ (nM) | — | 3633 |
| $T_{max}$ (h) | — | 3.33 |
| $T_{1/2}$ (h) | 3.34 | 3.90 |
| $V_{dss}$ (L/kg) | 5.86 | — |
| Cl (mL/min/kg) | 25.4 | — |
| $AUC_{0\text{-}last}$ (nM · h) | 6909 | 34251 |
| $AUC_{0\text{-}inf}$ (nM · h) | 6951 | 34925 |
| F (%) | — | 49.6 |

Note:
"—" represented not tested or no data obtained.

Experiment conclusion: The tested compound had good pharmacokinetic properties in rats, and the oral bioavailability was 49.6%.

Experimental Example 5: The Inhibitory Effect of the Compound on the Activity of Human Liver Microsomal Cytochrome P450 Isoenzymes (CYP1A2, CYP2C9, CYP2C19, CYP2D6 and CYP3A4)

The object of this study was to evaluate the effect of Example 4 on the activities of five isoenzymes (CYP1A2, CYP2C9, CYP2C19, CYP2D6 and CYP3A4) of human liver microsomal cytochrome P450 (CYP) using an in vitro test system. The specific probe substrates of CYP450 isozymes were incubated with human liver microsomes and different concentrations of Example 4, and reduced nicotinamide adenine dinucleotide phosphate (NADPH) was added to initiate the reaction. After the reaction was completed, the samples were treated, and liquid chromatography tandem mass spectrometry (LC/MS/MS) was used to detect the metabolites produced by specific substrates.

The test results were shown in Table 5 below:

TABLE 5

Inhibition of Example 4 on five P450 (CYP) isoenzyme subtypes

| P450 (CYP) isoenzyme Subtype | IC50 (µM) |
|---|---|
| CYP1A2 | >50 |
| CYP2C9 | >50 |
| CYP2C19 | 36.1 |
| CYP2D6 | 25.4 |
| CYP3A4 | 32.4 |

Experiment conclusion: Example 4 had no or weak inhibitory effect on five isozymes (CYP1A2, CYP2C9, CYP2C19, CYP2D6 and CYP3A4) of human liver microsomal cytochrome P450 (CYP).

Experimental Example 6: In Vivo Efficacy Study of Human Gastric Cancer NCI-N87 Cell BALB/c Nude Mice Subcutaneous Xenograft Tumor Model Experiment object: to study the efficacy of the tested compound on human gastric cancer NCI-N87 cell subcutaneous xenograft tumor in the BALB/c nude mouse model.

Experimental animals: female BALB/c nude mice, 6 to 8 weeks old, weight: 18 to 22 grams; Supplier: Shanghai Xipuer-Bikai Laboratory Animal Co., Ltd.

Experimental Methods and Steps:

6.1 Cell Culture

Human gastric cancer NCI-N87 cells were cultured in a monolayer in vitro, and the culture conditions were: RPMI-1640 medium with 10% fetal bovine serum, 100 U/mL penicillin, 100 µg/mL streptomycin and 2 mM glutamine, and 37° C., 5% $CO_2$. Conventional digestion treatment with pancreatin-EDTA for passage was carried out twice a week. When the cell saturation was 80% to 90%, the cells were collected, counted and inoculated.

6.2 Tumor Cell Inoculation (Tumor Inoculation)

0.2 mL of ($10 \times 10^6$) NCI-N87 cells were subcutaneously inoculated into the right back of each nude mouse (PBS: Matrigel=1:1). The grouping and administration were started when the average tumor volume reached 130 $mm^3$.

6.3 Preparation of Tested Samples:

The tested compound was prepared as a 10 mg/mL solution, and the solvent was 10% NMP+10% ethylene glycol stearate+80% water.

6.4 Tumor Measurement and Experimental Index

The experimental index was to investigate whether the tumor growth was inhibited, delayed or cured. Tumor diameter was measured twice a week with a vernier caliper. the calculation formula of tumor volume: $V=0.5 \times a \times b^2$, wherein a and b represented the long and short diameters of the tumor, respectively.

The anti-tumor efficacy of the compound was evaluated by TGI (%) or relative tumor proliferation rate T/C (%). TGI (%) reflected the tumor growth inhibition rate. Calculation of TGI (%): TGI (%)=[1−(average tumor volume at the end of administration in a treatment group−average tumor volume at the beginning of administration in this treatment group)/(average tumor volume at the end of administration in the solvent control group−average tumor volume at the beginning of administration in the solvent control group)]×100%.

relative tumor growth rate T/C (%): calculation formula was as follows: T/C %=TRTV/CRTV (TRTV: RTV of the treatment group; CRTV: RTV of the solvent control group). The relative tumor volume (RTV) was calculated according to the results of the tumor measurement. The calculation equation was $RTV=V_t/V_0$, where $V_0$ was the average tumor volume measured at beginning of the grouping and administration (i.e., $d_0$), and $V_t$ was the average tumor volume at the time of a certain measurement. TRTV and CRTV were obtained from the data on the same day.

6.5 Statistical Analysis

Statistical analysis included mean value and standard error (SEM) of the tumor volume of each group at each time point. The treatment group showed the best treatment effect on day 21 after the administration at the end of the test, so the statistical analysis was performed based on this data to evaluate the differences between the groups. The comparison between two groups was analyzed by T-test, and the comparison between three or more groups was analyzed by one-way ANOVA. If the F value was significantly different, the Games-Howell test was applied. If the F value was not significantly different, the Dunnet (2-sided) test was used for analysis. All data analysis was performed with SPSS 17.0. $p<0.05$ was considered significantly different.

6.6 Test Results

In this experiment, we evaluated the in vivo efficacy of the compound on human gastric cancer NCI-N87 cell subcutaneous xenograft tumor model. On the 21st day after administration, the tumor volume of the tumor-bearing mice in the solvent control group reached 971 $mm^3$. Compared with the solvent control group, Example 4 (T/C=2.92%, TGI=112.13%, p=0.012) had a significant anti-tumor effect, with an average tumor size of 29 $mm^3$. The body weight of the mice in the treatment group of Example 4 decreased slightly, and gradually recovered in the later period without other morbidity or death.

6.7 Test Conclusion and Discussion

Compared with the solvent group, Example 4 of the present disclosure all showed excellent tumor growth inhibition effects, with TGI of 112.13%. Therefore, the compound of the present disclosure had an excellent effect of inhibiting tumor growth.

TABLE 6

Evaluation of antitumor efficacy of the compound of the present
disclosure on human gastric cancer NCI-N87 xenograft tumor model
(calculated based on tumor volume on day 21 after administration)

| Groups | Tumor volume $(mm^3)^a$ (Day 21) | T/C$^b$ (%) | TGI$^b$ (%) | p value$^c$ |
|---|---|---|---|---|
| Solvent group | 971 ± 136 | — | — | — |
| Example 4 (100 mg/kg) | 29 ± 7 | 2.92 | 112.13 | 0.012 |

Note:
"—" no calculation
$^a$Mean ± SEM.
$^b$Tumor growth inhibition was calculated by T/C and TGI (TGI (%) = [1 − ($T_{21}$ − $T_0$)/($V_{21}$ − $V_0$)] × 100).
$^c$The p value was calculated based on the tumor volume.

6.8 Pharmacodynamic Experiment Accompanied by Concentration Analysis of Example 4 in Plasma, Tumor Tissue and Brain Tissue On day 21, the whole blood, tumor tissue, and brain tissue of two mice were collected 0.5 hour, 1 hour, and 2 hours after the last administration. The whole blood was centrifuged to prepare plasma, and the tumor tissue and brain tissue were homogenized to prepare tissue homogenate, and the drug concentration in plasma and tissue homogenate was analyzed by the LC-MS/MS method.

The results were shown in Table 7:

TABLE 7

Concentration of Example 4 in plasma and
tissue on day 21 after administration

| Plasma/tissue | Drug concentration (nM) | | |
|---|---|---|---|
| | 0.5 h | 1 h | 2 h |
| Plasma | 8600 | 7575 | 12800 |
| Tumor tissue | 9445 | 11195 | 21450 |
| Brain tissue | 538 | 631 | 1009 |

Experiment conclusion: After the administration of Example 4, a very high drug concentration could be achieved in the tumor tissue; Example 4 also had a higher distribution in the brain tissue.

Experimental Example 7: In Vivo Efficacy Study of Human Breast Cancer BT-474 Cell BALB/c Nude Mice Subcutaneous Xenograft Tumor Model Experiment object: to study the in vivo efficacy of the tested compound in human breast cancer BT-474 cell BALB/c nude mouse subcutaneous xenograft tumor model.

Experimental animals: female BALB/c nude mice, 6 to 8 weeks old, weight: 18 to 22 grams; Supplier Beijing Weitonglihua Laboratory Animal Technology Co., Ltd.

Experimental Methods and Steps:
7.1 Cell Culture

Human breast cancer BT474 cells were cultured in a monolayer in vitro. The culture conditions were: ATCC Hybri-Care Medium with 1.5 g/L sodium bicarbonate, 10% fetal bovine serum, 100 U/mL penicillin and 100 μg/mL streptomycin, and 37° C., 5% $CO_2$ incubator. Conventional digestion treatment with pancreatin-EDTA for passage was carried out twice a week. When the cell saturation was 80% to 90%, and the number reached the requirement, the cells were collected, counted and inoculated.

7.2 Tumor Cell Inoculation and Grouping 0.2 mL (1×10$^7$ cells) of BT474 cells (with matrigel in a volume ratio of 1:1) were subcutaneously inoculated on the right back of each mouse. The grouping and administration were started when the average tumor volume reached about 168 mm$^3$. (Estrogen tablets were inoculated three days before cell inoculation).

7.3 the Preparation of the Tested Samples, Tumor Measurement, Experimental Index and Statistical Analysis were the Same as in Experimental Example 6.

7.4 Test Results

In this experiment, we evaluated the in vivo efficacy of Example 4 and Example 32 in human breast cancer BT-474 cell BALB/c nude mice subcutaneous xenograft tumor model. The results were shown in Table 8. On the 20th day after administration, the tumor volume of the tumor-bearing mice in the Solvent control group reached 1207 mm$^3$. Compared with the solvent control group, Example 4 (T/C=2.62%, TGI=112.93%, p<0.05) had a significant antitumor effect, with an average tumor size of 33 mm$^3$. Compared with the solvent control group, Example 32 (T/C=7.84%, TGI=106.44%, p<0.05) had a significant antitumor effect, with an average tumor size of 101 mm$^3$.

7.5 Test Conclusion and Discussion

Compared with the solvent group, both Example 4 and Example 32 of the present disclosure showed excellent tumor growth inhibition effects with TGI of 112.93% and 106.44%, respectively. Therefore, the compound of the present disclosure had excellent antitumor effects.

TABLE 8

Evaluation of antitumor efficacy of the compound of the present
disclosure on human breast cancer BT-474 xenograft tumor model
(calculated based on tumor volume on day 20 after administration)

| Groups | Tumor volume $(mm^3)^a$ (Day 21) | RTV | T/C$^b$ (%) | TGI$^b$ (%) | p value$^c$ |
|---|---|---|---|---|---|
| Solvent group | 1,207 ± 91 | 7.77 ± 1.11 | — | — | — |
| Example 4 (100 mg/kg) | 33 ± 3 | 0.20 ± 0.02 | 2.62 | 112.93 | <0.001 |
| Example 32 (100 mg/kg) | 101 ± 12 | 0.61 ± 0.06 | 7.84 | 106.44 | <0.001 |

Note:
"—" no calculation
$^a$Mean ± SEM.
$^b$Tumor growth inhibition was calculated by T/C and TGI (TGI (%) = [1 − ($T_{21}$ − $T_0$)/($V_{21}$ − $V_0$)] × 100).
$^c$The p value was calculated based on RTV.

What is claimed is:

1. A compound represented by formula (I), a tautomer or stereoisomer thereof or a pharmaceutically acceptable salt thereof, (I)

wherein
m is 0, 1 or 2;
n is 0, 1 or 2;
$T_1$ is selected from N and CH;
$D_1$ is selected from O, $N(R_6)$ and $C(R_7)(R_8)$;
$R_1$ is independently selected from H, F, Cl, Br, I, OH, $NH_2$, $C_{1-6}$ alkyl and $C_{1-6}$ alkoxy, wherein the $C_{1-6}$ alkyl and $C_{1-6}$ alkoxy are optionally substituted with 1, 2 or 3 $R_a$;
$R_2$ is each independently selected from H, F, Cl, Br, I, OH, $NH_2$ and $C_{1-6}$ alkyl, wherein the $C_{1-6}$ alkyl is optionally substituted with 1, 2 or 3 $R_b$;
or $R_1$ and $R_2$ are attached to each other to form —$(CH_2)_p$—, where both m and n are 1;
$R_3$ and $R_4$ are each independently selected from H, F, Cl, Br, I, OH, $NH_2$ and $C_{1-6}$ alkyl, wherein the $C_{1-6}$ alkyl is optionally substituted with 1, 2 or 3 $R_c$;
or $R_3$ and $R_4$ are attached to each other to form —$(CH_2)_q$—;
p is 1 or 2;
q is 1 or 2;
$R_{51}$, $R_{52}$, $R_{53}$ and $R_{54}$ are each independently selected from H, F, Cl, Br, I, OH, $NH_2$, $C_{1-6}$ alkyl and $C_{1-3}$ alkoxy, wherein the $C_{1-6}$ alkyl and $C_{1-3}$ alkoxy are optionally substituted with 1, 2 or 3 $R_d$;
$R_6$ is selected from H, F, Cl, Br, I, OH, $NH_2$, $C_{1-6}$ alkyl and —C(=O)—$C_{2-6}$ alkenyl, wherein the $C_{1-6}$ alkyl and —C(=O)—$C_{2-6}$ alkenyl are optionally substituted with 1, 2 or 3 $R_e$;
$R_7$ is selected from H, F, Cl, Br, I, OH, $NH_2$ and $C_{1-6}$ alkyl, wherein the $NH_2$ and $C_{1-6}$ alkyl are optionally substituted with 1, 2 or 3 $R_f$;
$R_8$ is selected from H, F, Cl, Br, I and $C_{1-6}$ alkyl, wherein the $C_{1-6}$ alkyl is optionally substituted with 1, 2 or 3 $R_g$;
$R_9$ and $R_{10}$ are each independently selected from H, F, Cl, Br, I, OH, $NH_2$, $C_{1-6}$ alkyl and $C_{1-3}$ alkoxy, wherein the $C_{1-6}$ alkyl and $C_{1-3}$ alkoxy are optionally substituted with 1, 2 or 3 $R_h$;
$R_a$, $R_b$ and $R_c$ are each independently selected from F, Cl, Br, I, OH and $NH_2$;
$R_d$ is each independently selected from F, Cl, Br, I, OH, $NH_2$ and $C_{1-3}$ alkyl, wherein the $C_{1-3}$ alkyl is optionally substituted with 1, 2 or 3 R;
$R_e$, $R_f$, $R_g$ and $R_h$ are each independently selected from F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted with 1, 2 or 3 R;

R is each independently selected from F, Cl, Br, I, OH, $NH_2$, $CH_3$, Et and —$OCH_3$.

2. The compound, tautomer or stereoisomer thereof or pharmaceutically acceptable salt thereof as defined in claim 1, wherein $R_d$ is each independently selected from F, Cl, Br, I, OH and $NH_2$;
or, $R_e$, $R_f$, $R_g$ and Rh are each independently selected from F, Cl, Br, I, OH, $NH_2$, $CH_3$, Et, and —$OCH_3$.

3. The compound, tautomer or stereoisomer thereof or pharmaceutically acceptable salt thereof as defined in claim 1, wherein $R_1$ is each independently selected from H, F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted with 1, 2 or 3 $R_a$;
or, $R_2$ is each independently selected from H, F, Cl, Br, I, OH, $NH_2$ and $C_{1-3}$ alkyl, wherein the $C_{1-3}$ alkyl is optionally substituted with 1, 2 or 3 $R_b$;
or, $R_3$ and $R_4$ are each independently selected from H, F, Cl, Br, I, OH, $NH_2$ and $C_{1-3}$ alkyl, wherein the $C_{1-3}$ alkyl is optionally substituted with 1, 2 or 3 $R_c$;
or, $R_{51}$, $R_{52}$, $R_{53}$ and $R_{54}$ are each independently selected from H, F, Cl, Br, I, OH, $NH_2$ and $C_{1-3}$ alkyl, wherein the $C_{1-3}$ alkyl is optionally substituted with 1, 2 or 3 $R_d$;
or, $R_6$ is selected from H, F, Cl, Br, I, OH, $NH_2$, $C_{1-3}$ alkyl and —C(=O)—$C_{2-4}$ alkenyl, wherein the $C_{1-3}$ alkyl and —C(=O)—$C_{2-4}$ alkenyl are optionally substituted with 1, 2 or 3 $R_e$;
or, $R_7$ is selected from H, F, Cl, Br, I, OH, $NH_2$ and $C_{1-3}$ alkyl, wherein the $NH_2$ and $C_{1-3}$ alkyl are optionally substituted with 1, 2 or 3 $R_f$;
or, $R_8$ is selected from H, F, Cl, Br, I and $C_{1-3}$ alkyl, wherein the $C_{1-3}$ alkyl is optionally substituted with 1, 2 or 3 $R_g$;
or, $R_9$ and $R_{10}$ are each independently selected from H, F, Cl, Br, I, OH, $NH_2$ and $C_{1-3}$ alkyl, wherein the $C_{1-3}$ alkyl is optionally substituted with 1, 2 or 3 $R_h$.

4. The compound, tautomer or stereoisomer thereof or pharmaceutically acceptable salt thereof as defined in claim 3, wherein $R_1$ is each independently selected from H, F, Cl, Br, I, OH, $NH_2$, $CH_3$, Et and —$OCH_3$;
or, $R_2$ is each independently selected from H, F, Cl, Br, I, OH, $NH_2$, $CH_3$ and Et;
or, $R_3$ and $R_4$ are each independently selected from H, F, Cl, Br, I, OH, $NH_2$, $CH_3$ and Et;
or, $R_{51}$ $R_{52}$, $R_{53}$ and $R_{54}$ are each independently selected from H, F, Cl, Br, I, OH, $NH_2$, $CH_3$, Et and $CF_3$;
or, $R_6$ is selected from H, F, Cl, Br, I, OH, $NH_2$, $CH_3$, Et and —C(=O)—CH=$CH_2$;
or, $R_7$ is selected from H, F, Cl, Br, I, OH, $NH_2$, $CH_3$, Et, and or, $R_8$ is selected from H, F, Cl, Br, I, $CH_3$, Et and

or, $R_9$ and $R_{10}$ are each independently selected from H, F, Cl, Br, I, OH, $NH_2$, $CH_3$ and Et.

5. The compound, tautomer or stereoisomer thereof or pharmaceutically acceptable salt thereof as defined in claim 1, wherein structural unit

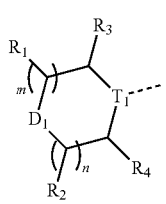

is selected from

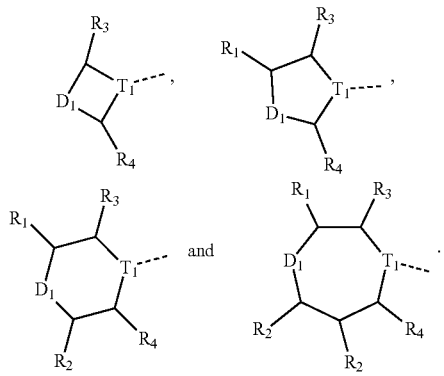

6. The compound, tautomer or stereoisomer thereof or pharmaceutically acceptable salt thereof as defined in claim 5, wherein structural unit

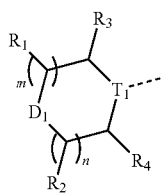

is selected from

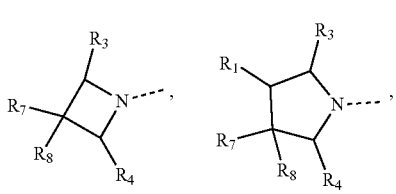

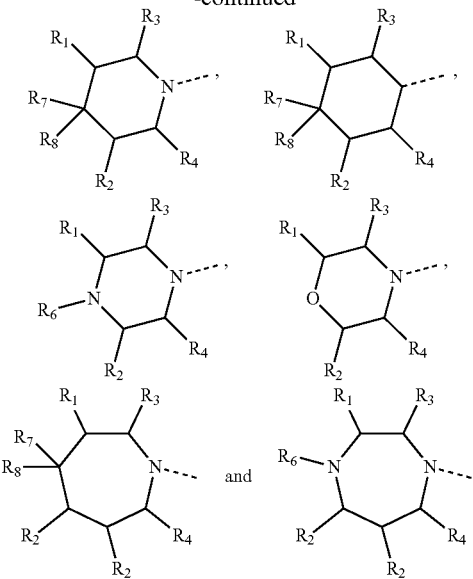

7. The compound, tautomer or stereoisomer thereof or pharmaceutically acceptable salt thereof as defined in claim 6, wherein structural unit

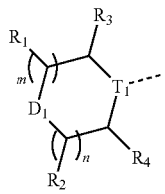

is selected from

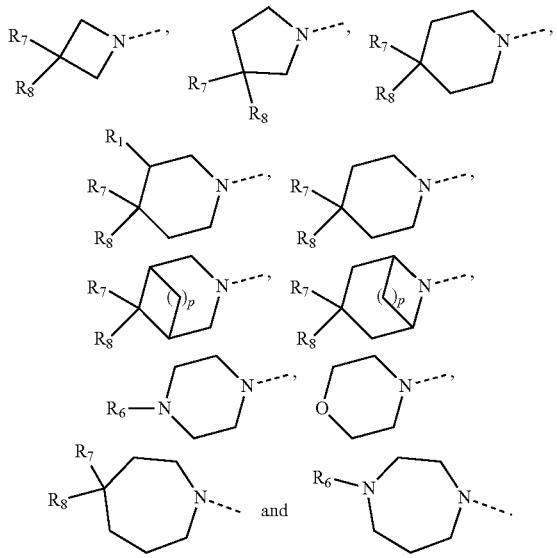

8. The compound, tautomer or stereoisomer thereof or pharmaceutically acceptable salt thereof as defined in claim 7, wherein structural unit

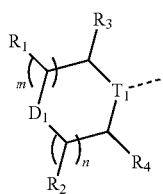
is selected from
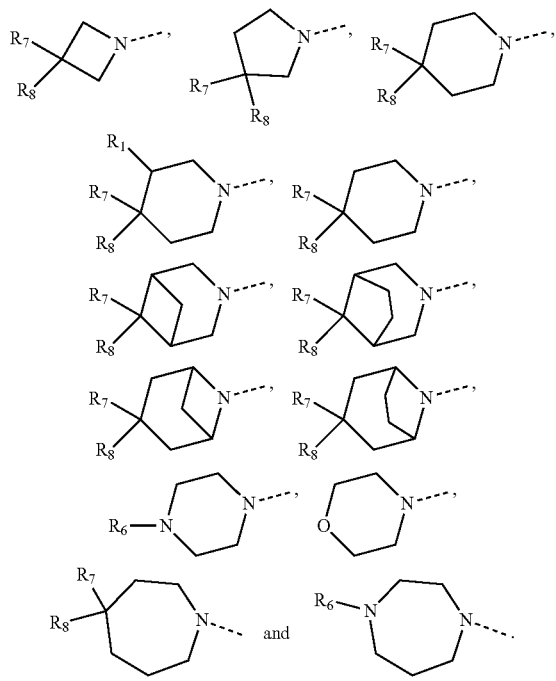
9. The compound, tautomer or stereoisomer thereof or pharmaceutically acceptable salt thereof as defined in claim 8, wherein structural unit
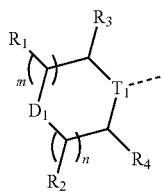
is selected from
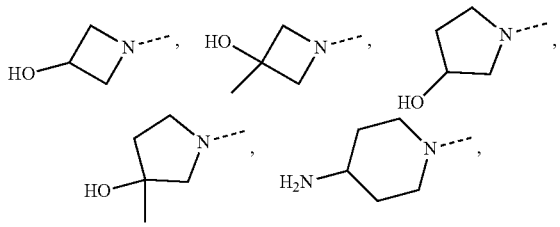
-continued
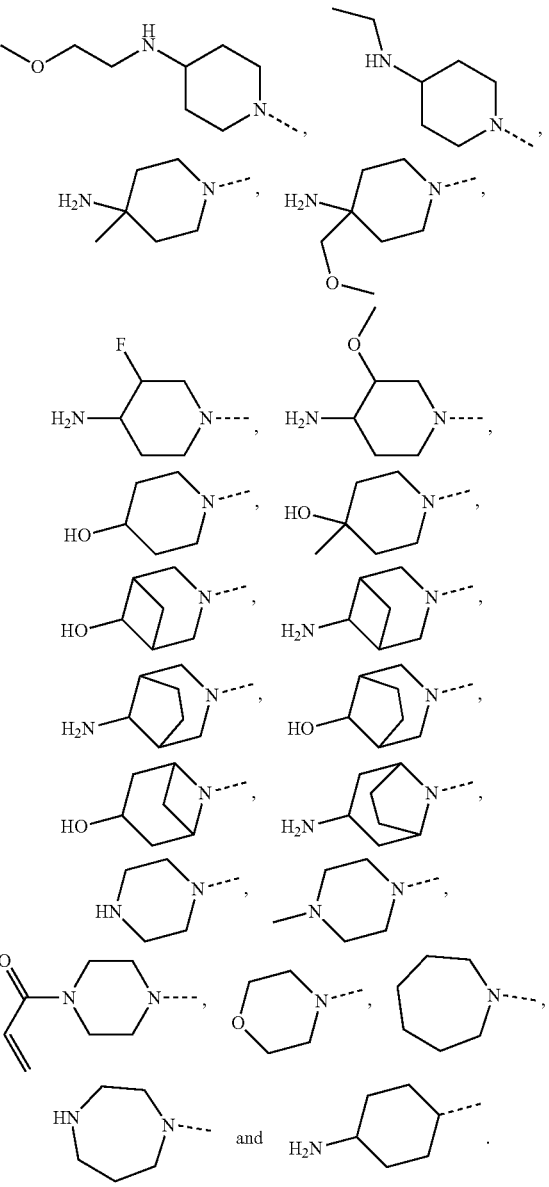
10. The compound, tautomer or stereoisomer thereof or pharmaceutically acceptable salt thereof as defined in claim 1, wherein the compound is selected from
(I-1)
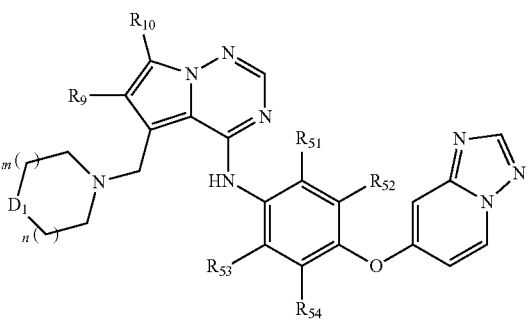

(I-2)
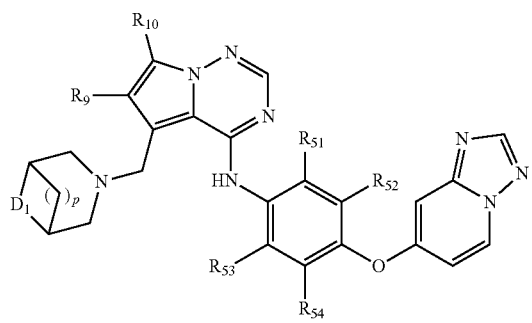
(I-3)
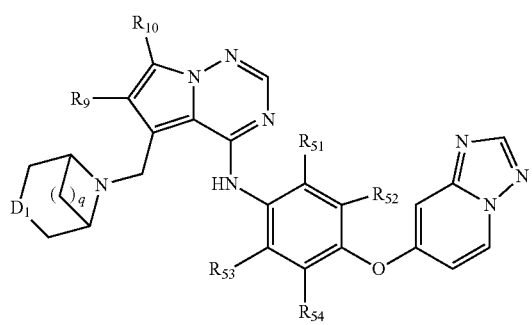
(II-1)
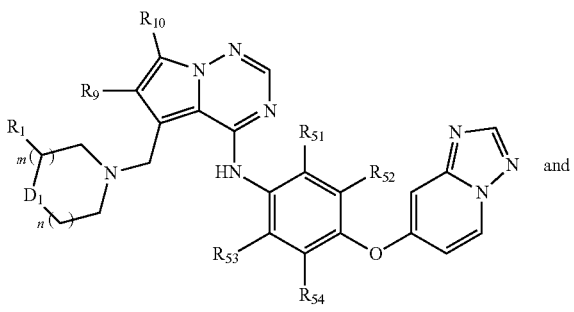
(II-2)
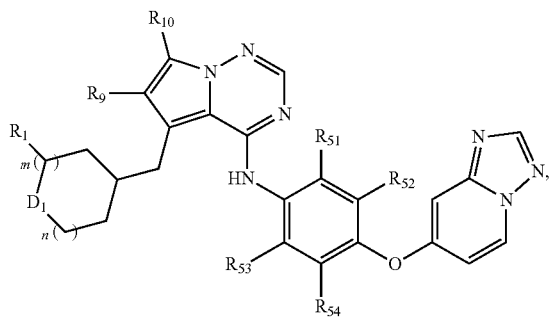
11. The compound, tautomer or stereoisomer thereof or pharmaceutically acceptable salt thereof as defined in claim 1, wherein the compound is selected from
(I-1A)
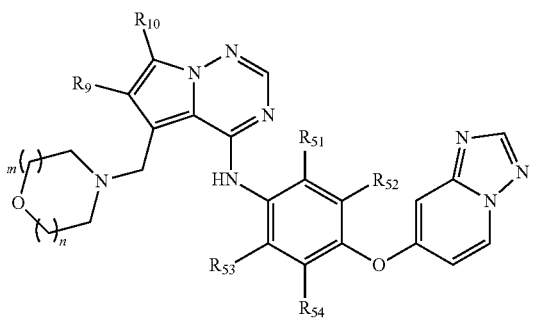
(I-1B)
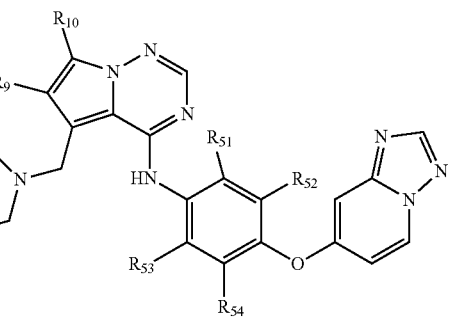
(I-1C)
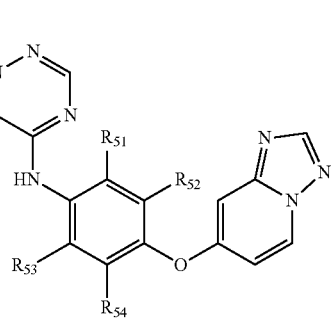
(I-2A)
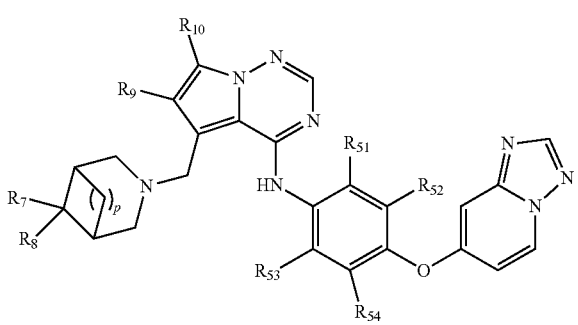

-continued
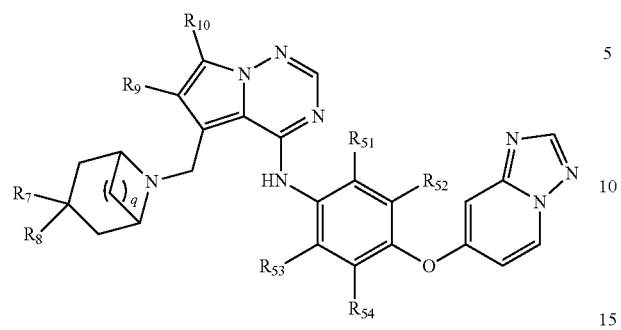
(I-3A)
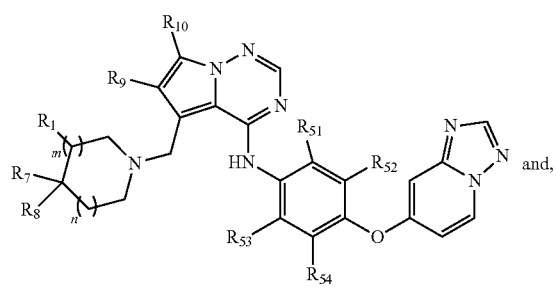
(II-1A)
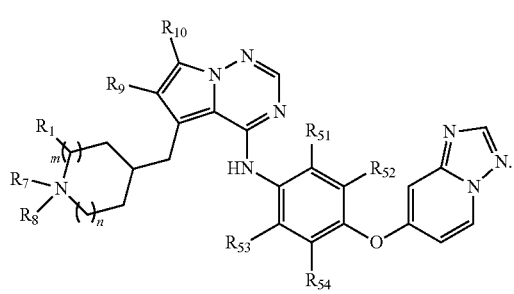
(II-1B)
12. The compound, tautomer or stereoisomer thereof or pharmaceutically acceptable salt thereof as defined in claim 1, wherein the compound is selected from
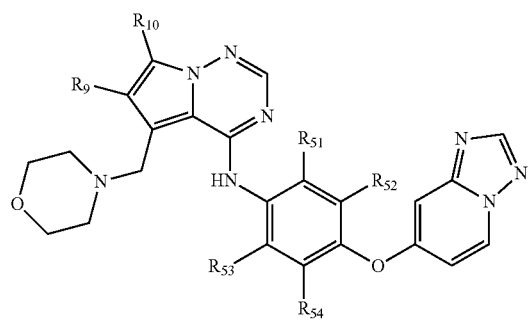
(I-1A1)
-continued
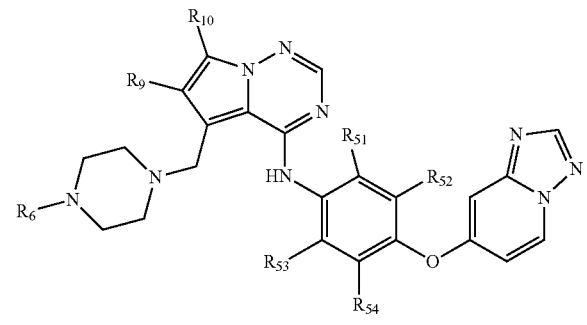
(I-1B1)
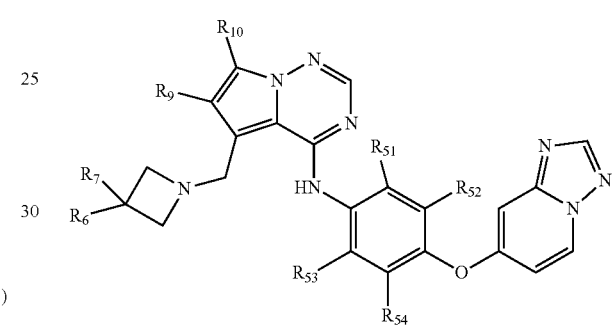
(I-1C1)
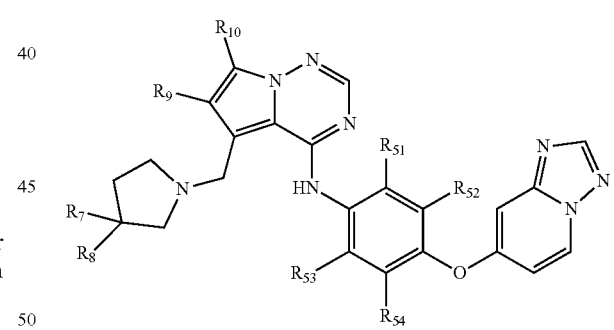
(I-1C2)
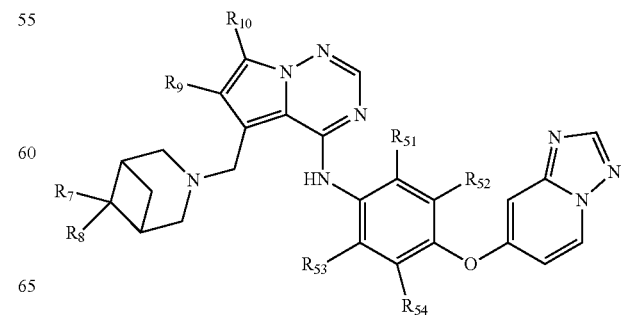
(I-2A1)

13. A compound, a tautomer or stereoisomer thereof or a pharmaceutically acceptable salt thereof, wherein the compound is selected from 105
-continued
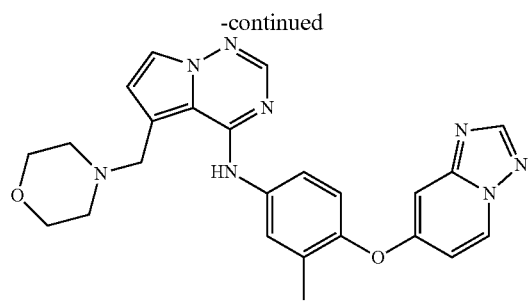
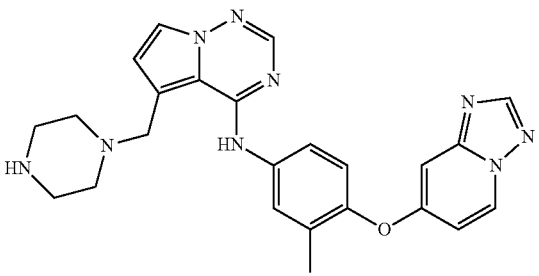
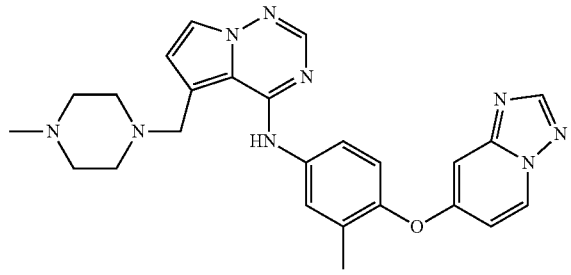
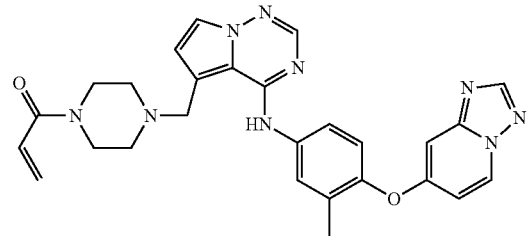
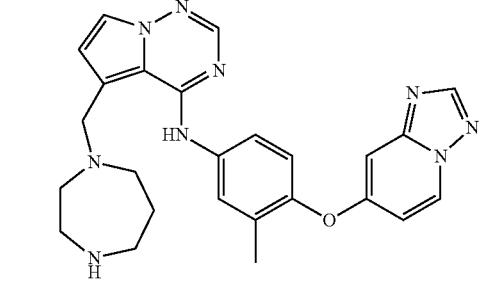
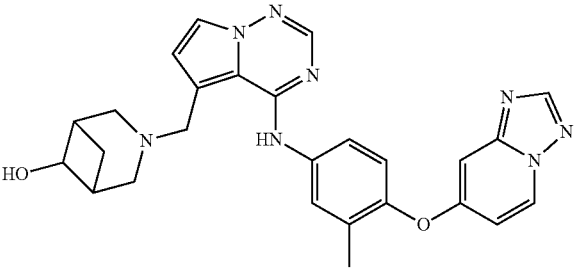
106
-continued
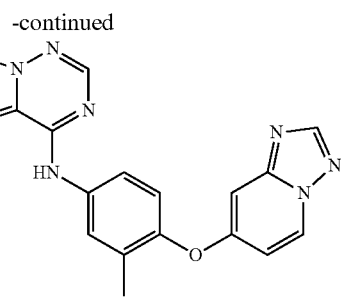
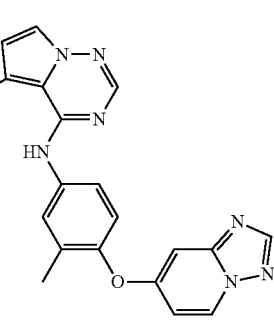

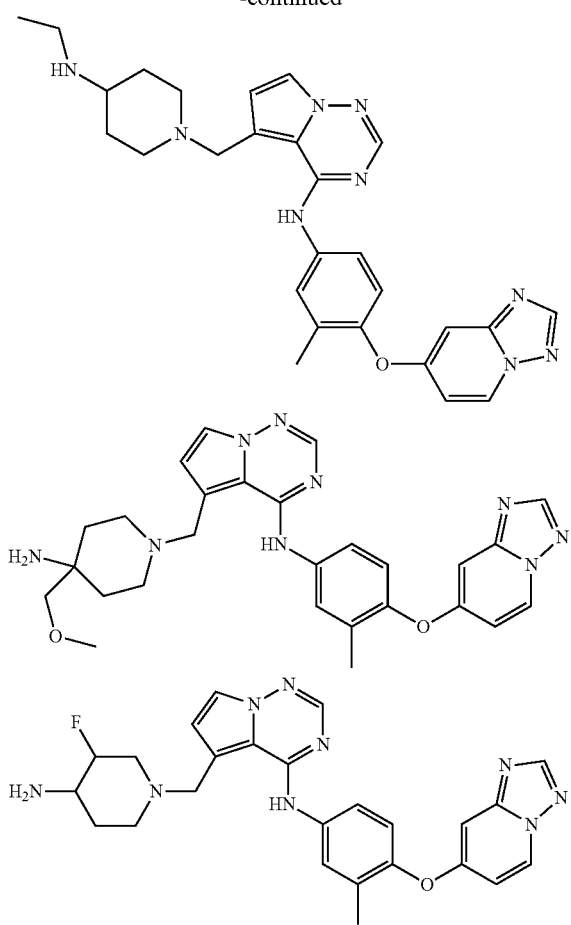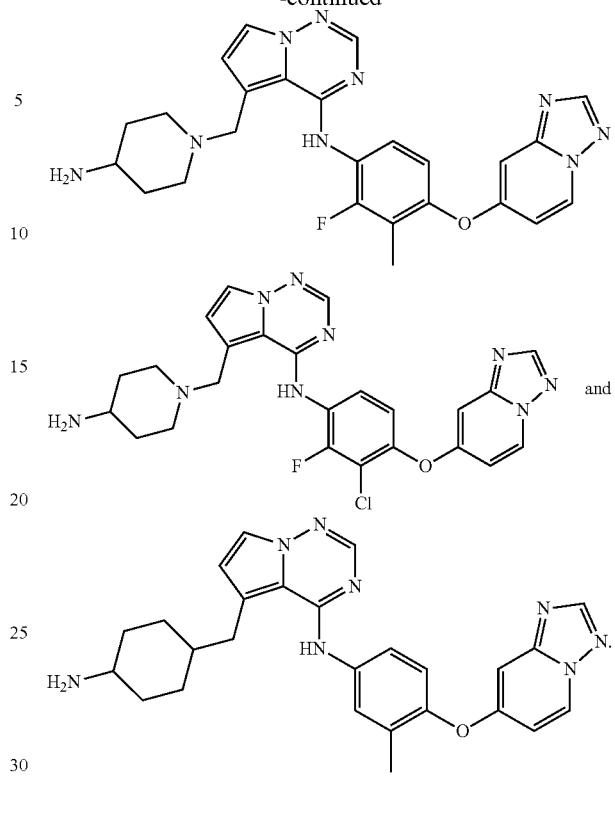
14. The compound, tautomer or stereoisomer thereof or pharmaceutically acceptable salt thereof as defined in claim 13, wherein the compound is selected from
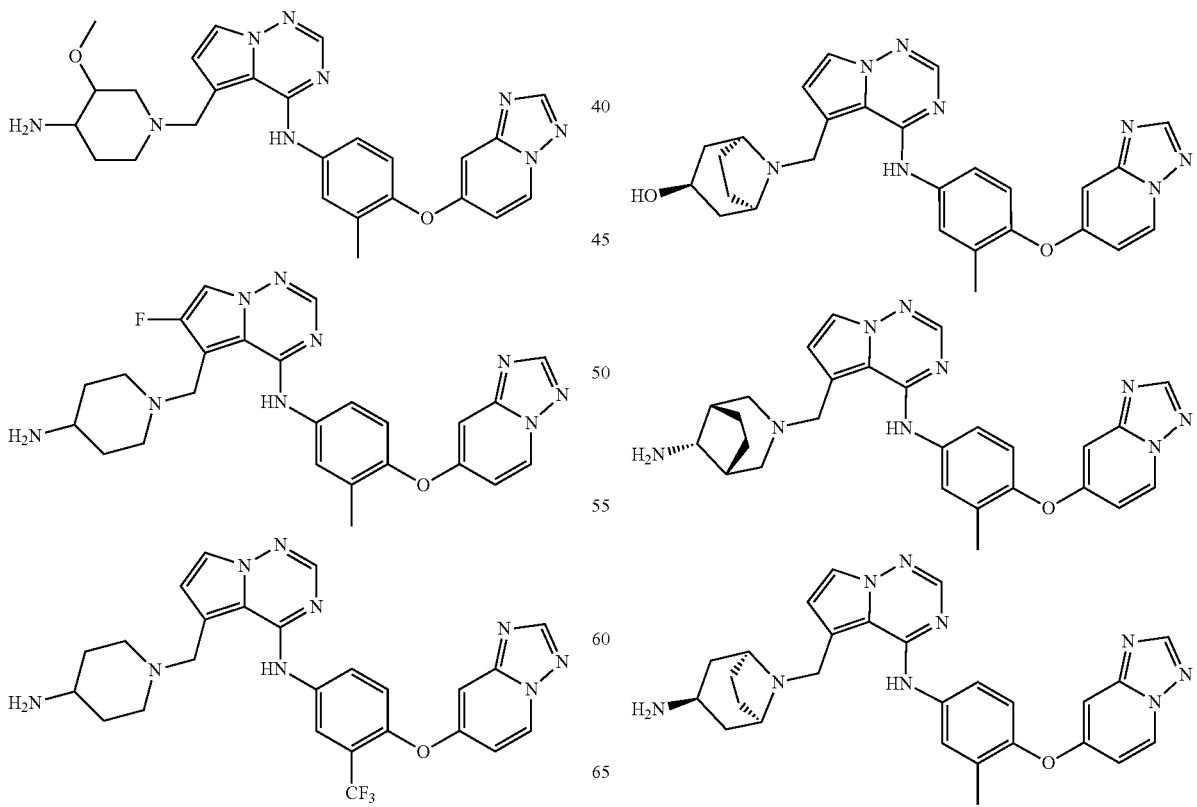

109
-continued
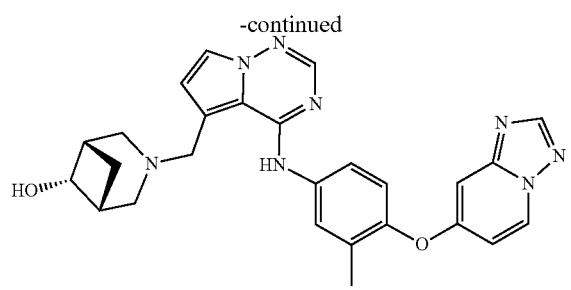
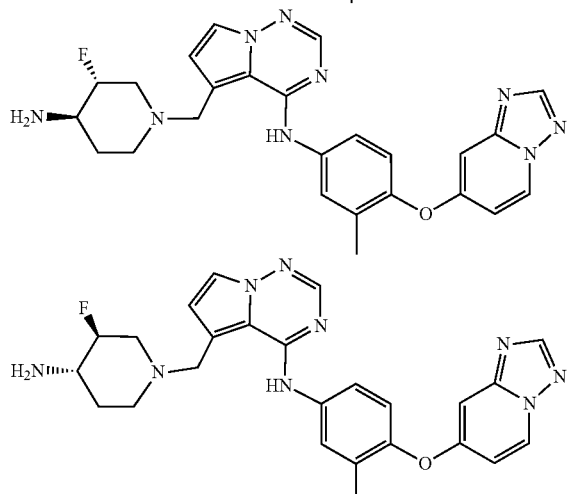
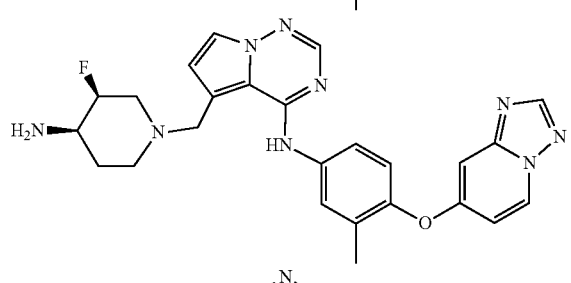
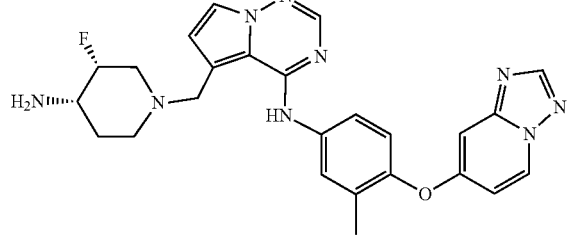
110
-continued
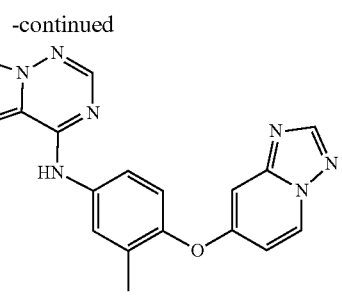
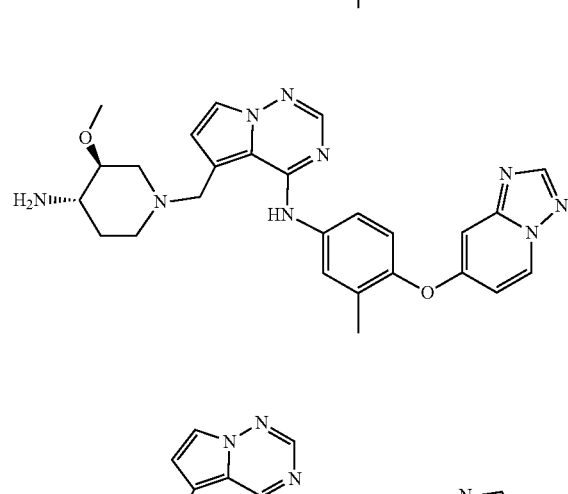
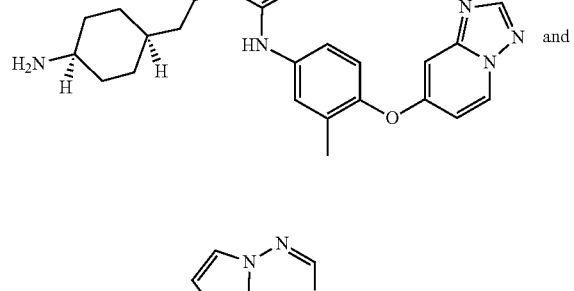 and
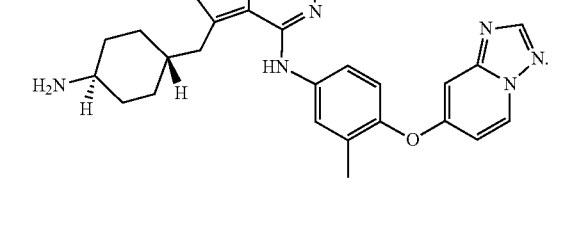
* * * * *